(12) United States Patent
Wu et al.

(10) Patent No.: US 10,617,690 B2
(45) Date of Patent: Apr. 14, 2020

(54) JAK INHIBITOR

(71) Applicant: WUXI FORTUNE PHARMACEUTICAL CO., LTD, Jiangsu (CN)

(72) Inventors: Hao Wu, Shanghai (CN); Weiwei Mao, Shanghai (CN); Lili Fan, Shanghai (CN); Charles Z. Ding, Shanghai (CN); Shuhui Chen, Shanghai (CN); Fei Wang, Shanghai (CN); Guoping Hu, Shanghai (CN); Jian Li, Shanghai (CN)

(73) Assignee: WUXI FORTUNE PHARMACEUTICAL CO., LTD, Jiangsu (CN)

( * ) Notice: Subject to any disclaimer, the term of this patent is extended or adjusted under 35 U.S.C. 154(b) by 149 days.

(21) Appl. No.: 15/545,245

(22) PCT Filed: Jan. 19, 2016

(86) PCT No.: PCT/CN2016/071313
§ 371 (c)(1),
(2) Date: Jul. 20, 2017

(87) PCT Pub. No.: WO2016/116025
PCT Pub. Date: Jul. 28, 2016

(65) Prior Publication Data
US 2017/0360794 A1   Dec. 21, 2017

(30) Foreign Application Priority Data

Jan. 20, 2015 (CN) .......................... 2015 1 0029259
Jan. 11, 2016 (CN) .......................... 2016 1 0016564

(51) Int. Cl.
| | | |
|---|---|---|
| C07D 487/04 | (2006.01) | |
| C07D 519/00 | (2006.01) | |
| A61K 31/519 | (2006.01) | |
| A61K 31/551 | (2006.01) | |
| A61K 31/5377 | (2006.01) | |
| A61P 19/02 | (2006.01) | |
| A61P 37/06 | (2006.01) | |
| A61P 1/00 | (2006.01) | |
| A61P 17/00 | (2006.01) | |
| A61P 29/00 | (2006.01) | |
| A61K 31/165 | (2006.01) | |
| A61K 31/4523 | (2006.01) | |

(52) U.S. Cl.
CPC .......... A61K 31/519 (2013.01); A61K 31/165 (2013.01); A61K 31/4523 (2013.01); A61K 31/5377 (2013.01); A61K 31/551 (2013.01); A61P 1/00 (2018.01); A61P 17/00 (2018.01); A61P 19/02 (2018.01); A61P 29/00 (2018.01); A61P 37/06 (2018.01); C07D 487/04 (2013.01); C07D 519/00 (2013.01)

(58) Field of Classification Search
CPC .. C07D 487/04; C07D 519/00; A61K 31/519; A61K 31/551; A61K 31/5377; A61P 19/92; A61P 19/02
USPC ................ 544/281; 540/575; 514/265.1, 218
See application file for complete search history.

(56) References Cited

U.S. PATENT DOCUMENTS

| | | | |
|---|---|---|---|
| 7,301,023 | B2 | 11/2007 | Flanagan et al. |
| 8,808,764 | B2 | 8/2014 | Heaton et al. |
| 2002/0094974 | A1 | 7/2002 | Castelhano et al. |
| 2013/0131039 | A1 | 5/2013 | Burgess et al. |
| 2014/0228349 | A1 | 8/2014 | Boys et al. |

FOREIGN PATENT DOCUMENTS

| | | |
|---|---|---|
| CN | 1489590 A | 4/2004 |
| CN | 1729192 A | 2/2006 |
| CN | 102985424 A | 3/2013 |
| CN | 103987713 A | 8/2014 |
| WO | 2002096909 A1 | 12/2002 |
| WO | 2009047514 A1 | 4/2009 |
| WO | 2010020905 A1 | 2/2010 |
| WO | 2015087201 A1 | 6/2015 |

OTHER PUBLICATIONS

Verstovsek S., American Society of Hematology, 636-642, 2009.*
Cornejo et al., Int J Biochem Cell Biol. 41 (12): 2376-2379, 2009.*
Meyer et al., Clin Cancer Res; 20(8); 2051-9, 2014.*
Cohen et al., Current Opinion in Chemical Biology, 3,459-465, 1999.*
Freshney et al.,Culture of Animal Cells, A Manual of Basic Technique, Alan R. Liss, Inc., 1983, New York, pz.*

(Continued)

*Primary Examiner* — Venkataraman Balasubramanian
(74) *Attorney, Agent, or Firm* — Innovation Capital Law Group, LLP; Vic Lin

(57) ABSTRACT

The present invention discloses a series of JAK inhibitors, and particularly discloses a compound of formula (I) or a pharmaceutically acceptable salt thereof and the use thereof in preparation of drugs for treating diseases related to JAK.

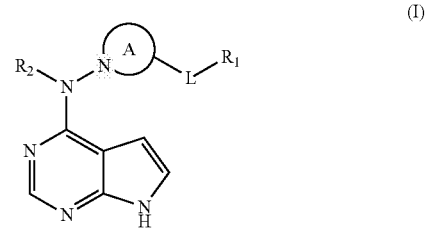

(I)

27 Claims, No Drawings

(56) References Cited

OTHER PUBLICATIONS

Dermeret al., Bio/Technology, 1994, 12:320.*
Golub et al., Science, 286, 531-537, 1999.*
Cecil Textbook of Medicine, edited by Bennet, J.C., and Plum F., 20th edition,vol. 1, 1004-101 O, 1996.*
Baxter EJ, et al., "Acquired mutation of the tyrosine kinase JAK2 in human myeloproliferative disorders", Lancet. 2005; 365 (9464): 1054-61.
Berge et al., "Pharmaceutical Salts", Journal of Pharmaceutical Science 66: 1-19 (1977).
European Search Report dated Jun. 28, 2018 from European Application No. 16739772.8.
Flanagan et al., "Discovery of CP-690,550: A Potent and Selective Janus Kinase (JAK) Inhibitor for the Treatment of Autoimmune diseases and Organ Transplant Rejection", Journal of Medicinal Chemistry, vol. 53, No. 24, Dec. 23, 2010, pp. 8468-8484.
Hubert Maehr, "A Proposed New Convention for Graphic Presentation of Molecular Geometry and Topography", J. Chem. Ed. 1985, 62: 114-120.
International Search Report & Written Opinion dated Jun. 30, 2016 from PCT Application No. PCT/CN2016/080208.
International Search Report & Written Opinion from corresponding International PCT Application No. PCT/CN2016/071313.
Japan Office Action dated Jun. 19, 2018 from Japanese Application No. 2017-539364.
Levy et al., "STAT3 Signaling and the Hyper-IgE Syndrome", N Engl J Med 2007; 357:1655-1658 Oct. 18, 2007 DOI: 10.1056/NEJMe078197.
Linda M. Scott et al., "JAK2 Exon 12 Mutations in Polycythemia Vera and Idiopathic Erythrocytosis", NEngl J Med 2007;356:459-68.

O Kilpivaara et al., "JAK2 and MPL mutations in myeloproliferative neoplasms: discovery and science", Leukemia (2008) 22, 1813-1817.
O'Shea, "Targeting the Jak/STAT pathway for immonusuppression", Ann Rheum Dis 2004;63(Suppl II):ii67-ii71. doi: 10.1136/ard.2004.028290.
Remington, "The Science and Practice of Pharmacy", 21st Ed., Lippincott, Williams & Wilkins (2005).
Vainchenker W, et al., "Constantinescu SNJAKs in pathology: role of Janus kinases in hematopoietic malignancies and immunodeficiencies", Semin Cell Dev Biol 19:385-393 (http://www.sciencedirect.com/science/journal/10849521/19/4?sdc=1).
Office Action dated Jul. 27, 2018 from U.S. Appl. No. 15/577,674.
Gionata Fiorino, et al., "JAK inhibitors: Novel developments in management of ulcerative colitis", 2018, Best Practice & Research Clinical Gastroenterology.
Jie Li, et al., "Activation of JAK-STAT1 signal transduction pathway in lesional skin and monocytes from patients with systemic lupus erythematosus", J Cent South Univ (Med Sci), 2011, 36(2), pp. 109-115.
Leeyen Hsu et al, "JAK Inhibitors: Treatment Efficacy and Safety Profile in Patients with Psoriasis", J Immunol Res. 2014; 2014: 283617, 15 pages.
Maria Alexandra Rodrigues & Tiago Torres, "JAK/STAT inhibitors for the treatment of atopic dermatitis", (2019), Journal of Dermatological Treatment, 5 pages.
Wenyu Jin, et al., "Effects of Topical JAK1 /JAK2 Inhibitor on Atopic Dermatitis Mice Model", Chin J Derm Venereol, Jan. 2019, vol. 33, No. 1, China Academic Journal Electronic Publishing House, abstract, pp. 23-24.

* cited by examiner

JAK INHIBITOR

TECHNICAL FIELD

The present invention relates to a series of JAK inhibitors, and particularly, relates to a compound of formula (I) or a pharmaceutically acceptable salt thereof.

BACKGROUND

JAK belongs to tyrosine kinase family participating in inflammation, autoimmune diseases, proliferative diseases, transplant rejection, diseases relating to cartilage turnover impairment, achondrogenesis and/or diseases related to hypersecretion of IL6.

The present invention also provides a compound, a method for preparing the compound and a composition comprising the same, and a method for preventing and/or treating inflammation, autoimmune diseases, proliferative diseases, transplant rejection, diseases relating to cartilage turnover impairment, achondrogenesis and/or diseases related to hypersecretion of IL6 by administrating the compound of the present invention.

Janus kinase (JAK) is a cytoplasm tyrosine kinase transducing cytokine signal from a membrane receptor to STAT transcription factor. There are four JAK family members including JAK1, JAK2, JAK3 and TYK2 in prior art. When a cytokine combine with its receptor, the JAK family members get autophosphorylated and/or transphosphorylated with each other, then STATs are phosphorylated and move into nucleus to regulate transcription. The JAK-STAT cellular signal pathway goes for interferon, most interleukins, multiple cytokines and endocrine factors, such as EPO, TPO, GH, OSM, LIF, CNTF, GM-CSF and PRL (Vain chenker W. etc. (2008)).

Combination research of genetic models and micro molecule JAK inhibitor discloses the therapeutic potency of several JAKs. It is confirmed through genetic studies of mouse and human that JAK3 is an immunosuppression target (O'SheaJ. etc. (2004)). JAK3 inhibitor has been successfully used in clinical development, and was used in organ transplantation rejection initially, and afterwards also was used in other immune inflammation indications, such as rheumatoid arthritis (RA), psoriasis and crohn disease (http://clinicaltrials.gov/). TYK2 is a potential target of immunoinflammatory disease, which has been confirmed through human genetic study and knockout research of mouse (Levy D. and Loomis C. (2007)). JAK1 is a new target of the field of immunoinflammatory disease. JAK1 is heterodimerized with other JAKs to transduce pro-inflammatory signal actuated by cytokines. Therefore, it is expected that JAK1 and/or other JAKs have therapeutic benefit to a series of inflammatory diseases and other diseases driven by signal transduction mediated by JAK.

Tofacitinib was developed by Pfizer, related patents are WO02/096909, U.S. Pat. No. 7,301,023 and WO2015087201, and it was successfully launched in America on Nov. 7, 2012 for the treatment of rheumatoid arthritis and Crohn's disease with the proprietaryname of Xeljanz®.

The patents for Filgotinib include U.S. Pat. No. 8,808,764 and WO2009047514A1, and Filgotinib is selective Jk1 inhibitor developed by Galapagos Company and used for the rheumatoid arthritis and Crohn's disease, and it is now in phase II clinical trials. It was reported that the active Jak1 IC50=10 nM Jak2 IC50=28 nM.

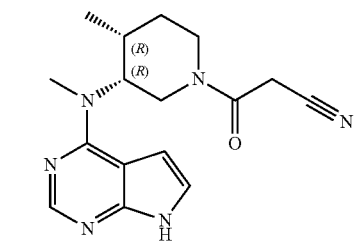

Tofacitinib

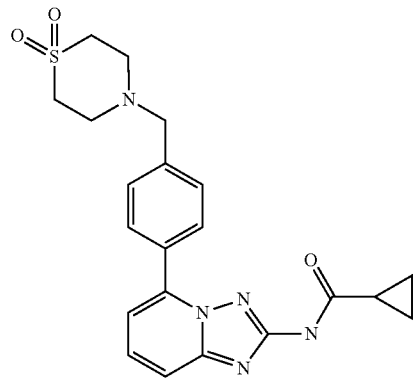

Filgotinib (GLPG0634)

SUMMARY

The present invention provides a compound of formula (I) or a pharmaceutically acceptable salt thereof,

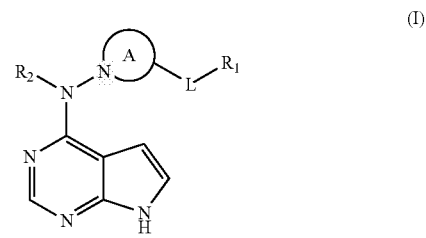

wherein, ring A is selected from optionally substituted: 5~12 membered heterocycloalkyl or 5~6 membered heteroaryl;

$R_1$ is selected from H or optionally substituted $C_{1-6}$ alkyl, $C_{1-6}$ heteroalkyl, $C_{3-6}$ cycloalkyl, 3~6 membered heterocycloalkyl, 5~6 membered aryl, or 5~6 membered heteroaryl;

L is selected from single bond, —C(=O)O—, acyl or optionally substituted: amino, aminoacyl, acyl amino methylene and aminoacyl methylene; optionally, $R_1$ and the N in L form a optionally substituted 3~6 membered ring;

$R_2$ is selected from H, or optionally substituted $C_{1-3}$ alkyl and 3~6 membered cycloalkyl; optionally, the structural unit

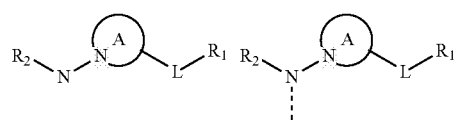

can be replaced by

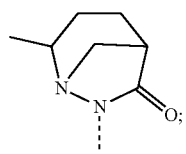

"hetero" represents O, S or N, and the number thereof is selected from 1, 2 or 3.

In an embodiment of the present invention, substituents of the said 5~10 membered heterocycloalkyl, 5~6 membered heteroaryl, $C_{1-6}$ alkyl, $C_{1-6}$ heteroalkyl, $C_{3-6}$ cycloalkyl, 3~6 membered heterocycloalkyl, 5~6 membered aryl, 5–6 membered heteroaryl, amino, aminoacyl, acylamino methylene, aminoacyl methylene, $C_{1-3}$ alkyl, and 3~6 membered ring are selected from halogen, cyano, hydroxy, amino or optionally selected from halogenated, hydroxylated and/or ammoniated: $C_{1-3}$ alkyl and $C_{1-3}$ heteroalkyl.

In an embodiment of the present invention, the number of the substituent is selected from 0, 1, 2, 3, 4 or 5.

In an embodiment of the present invention, the substituent is selected from F, Cl, Br, I, OH, $NH_2$, CN, Me, ethyl, n-propyl, isopropyl, cyclopropyl and trifluoromethyl.

In an embodiment of the present invention, ring A is selected from optionally substituted: piperidyl, piperazinyl, morpholinyl, pyrrolidinyl, oxazolyl and 7-12 membered heterocyclyl with 1~2 heteroatoms.

In an embodiment of the present invention, ring A is selected from optionally substituted:

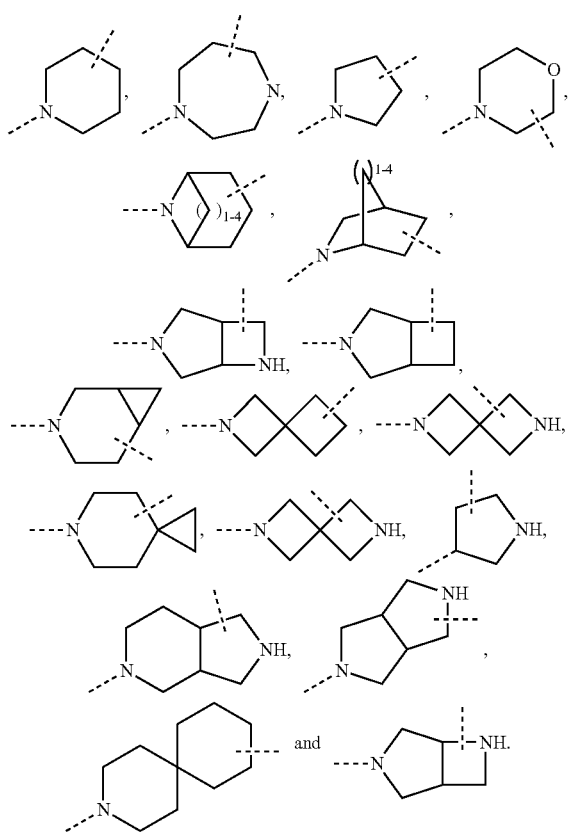

In an embodiment of the present invention, ring A is selected from:

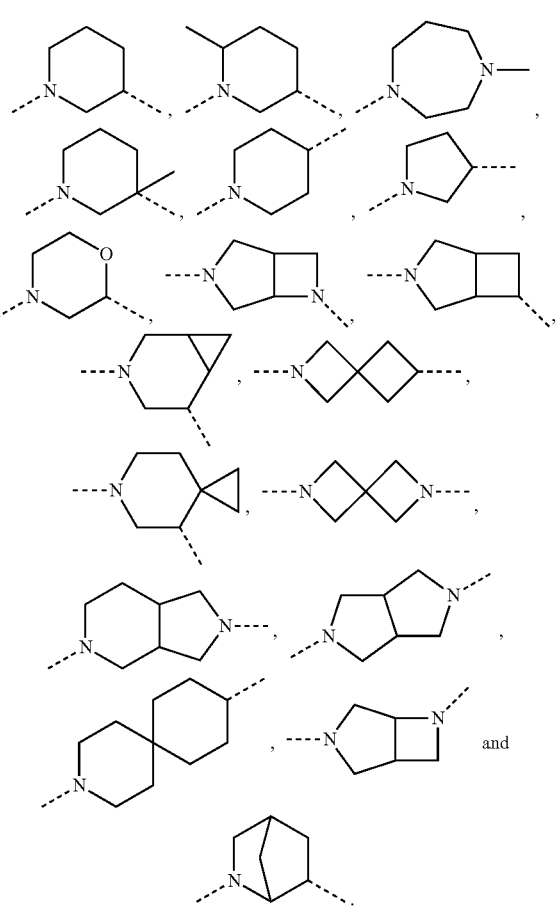

In an embodiment of the present invention, R1 is selected from H, or optionally substituted: $C_{1-4}$ alkyl, $C_{1-2}$ alkyl-O—$C_{1-2}$ alkyl-, $C_{1-2}$ alkyl-S—$C_{1-2}$ alkyl-, $C_{4-5}$ cycloalkyl, 6 membered aryl, or 5 membered heteroaryl.

In an embodiment of the present invention, R1 is selected from H, or optionally substituted: Me,

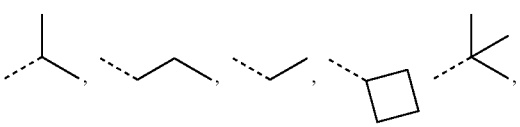

$C_{1-2}$ alkyl-O—$C_{1-2}$alkyl-, $C_{1-2}$alkyl-S—$C_{1-2}$alkyl-, imidazolyl and phenyl.

In an embodiment of the present invention, R1 is selected from H,

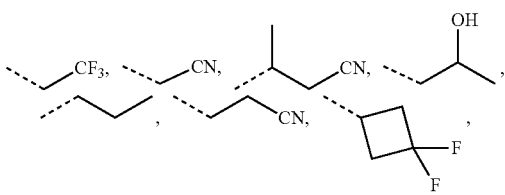

-continued

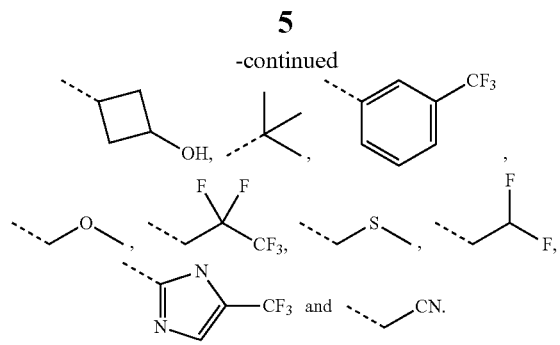

In an embodiment of the present invention, R1 and the N in L form an optionally substituted 4-5 membered ring.

In an embodiment of the present invention, the ring formed by $R_1$ and the N in L is selected from

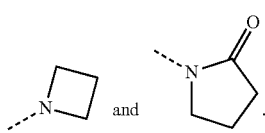

In an embodiment of the present invention, $R_1$-L- is selected from optionally substituted: Me,

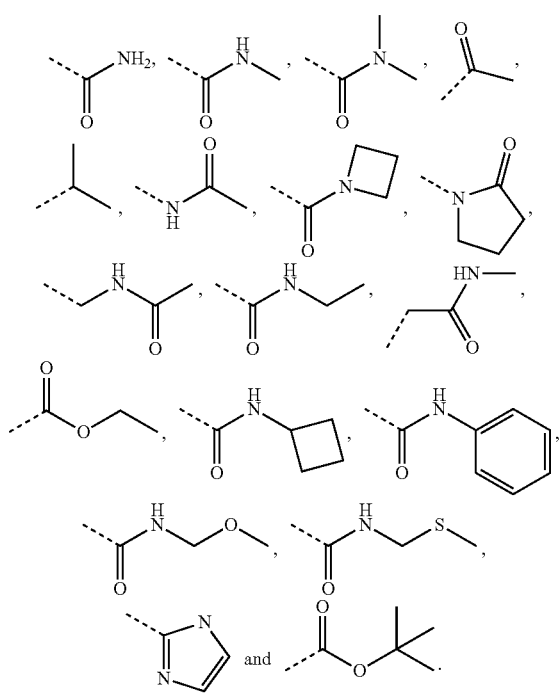

In an embodiment of the present invention, $R_1$-L- is selected from

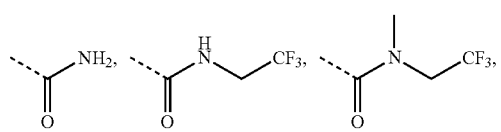

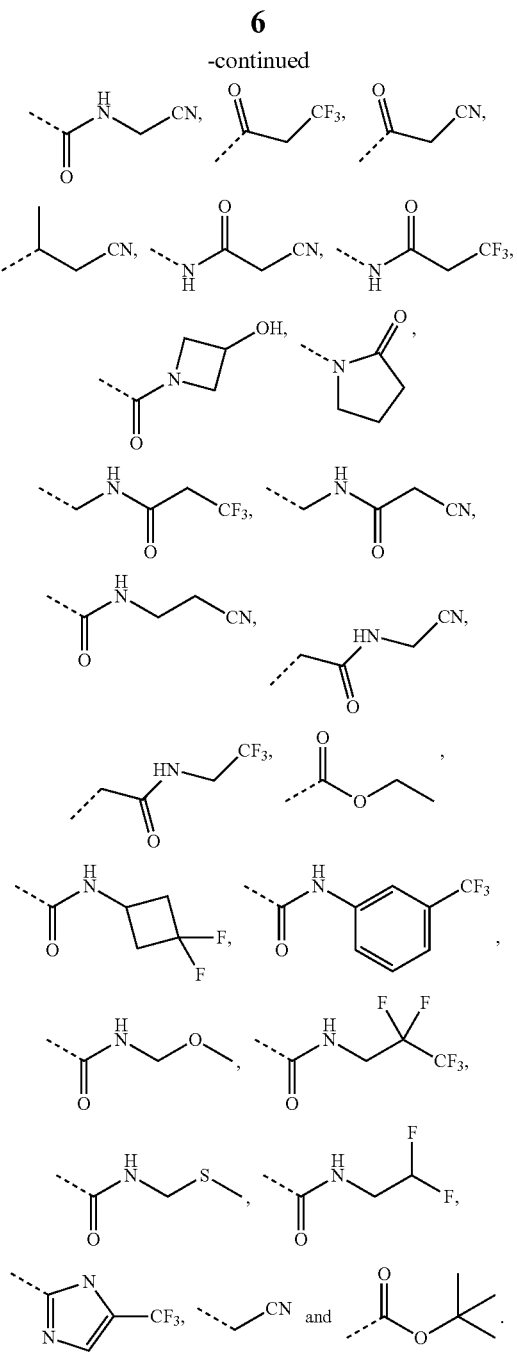

In an embodiment of the present invention, $R_2$ is selected from H, methyl, ethyl or cyclopropyl.

A compound of the present invention is selected from:

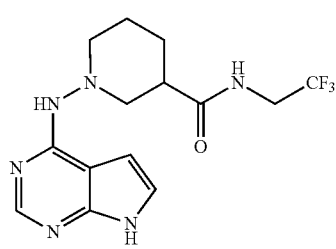

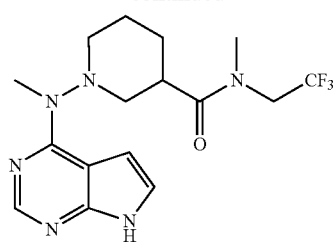
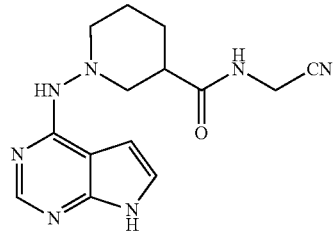
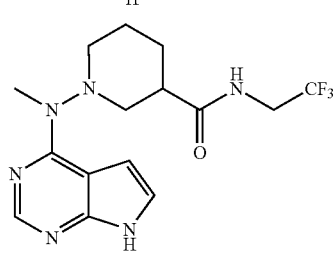
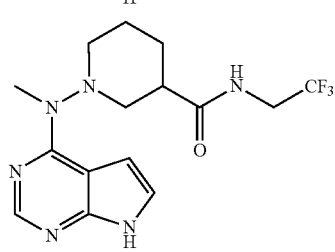
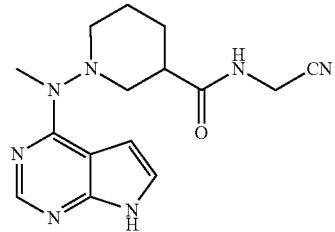
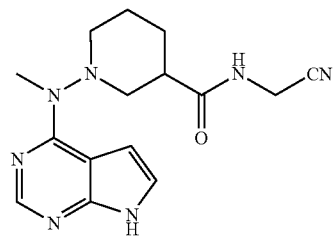
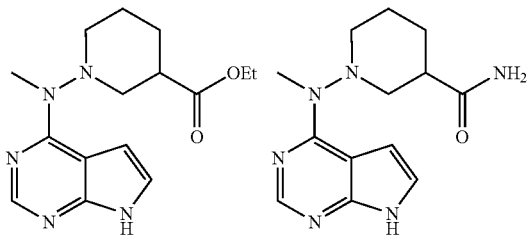
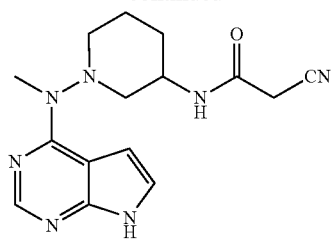
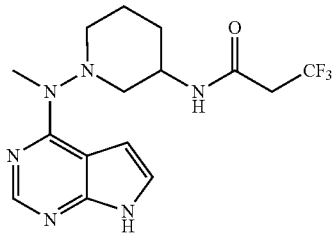
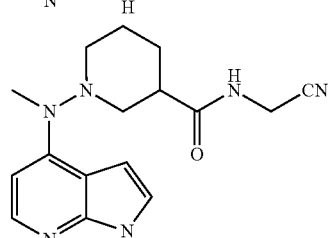
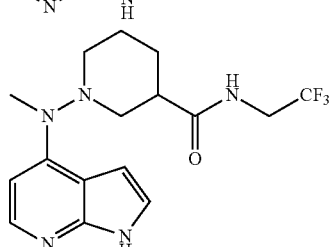
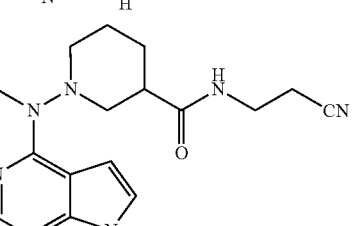
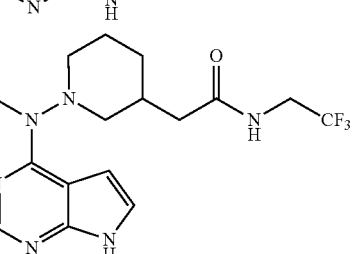
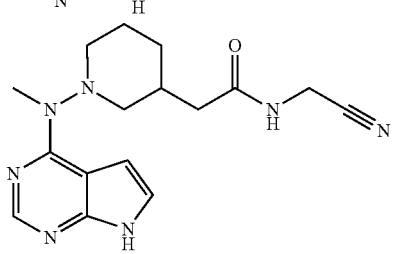

-continued
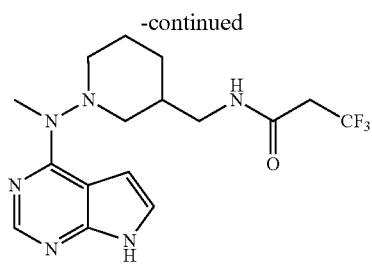
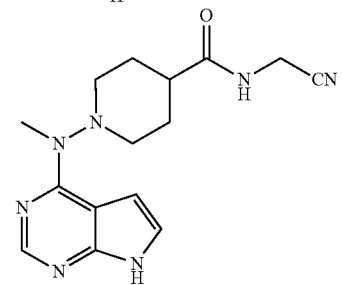
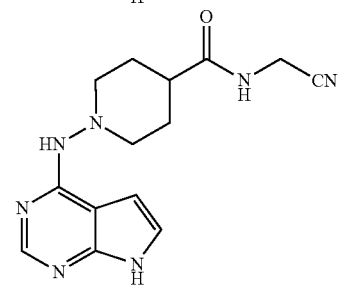
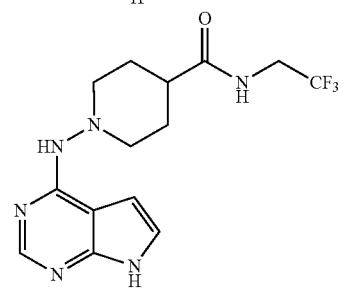
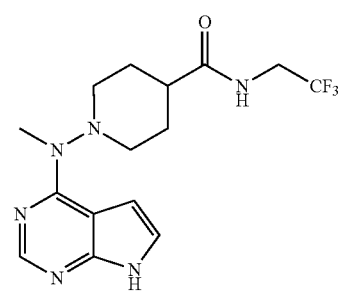
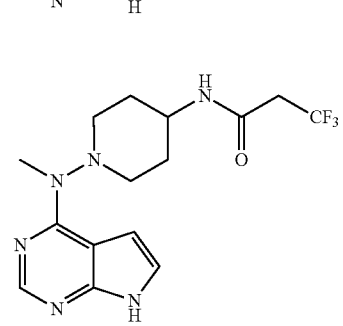
-continued
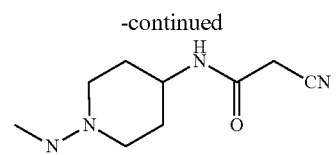
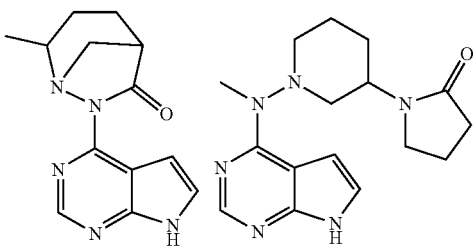
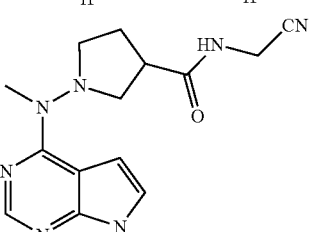
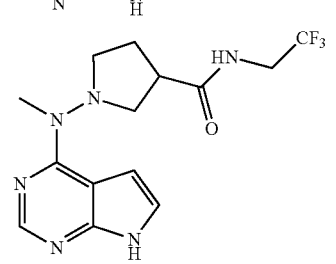
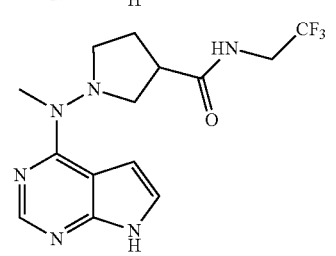

11
-continued
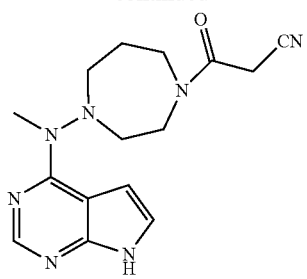
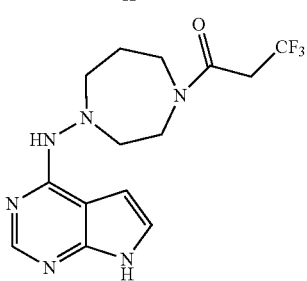
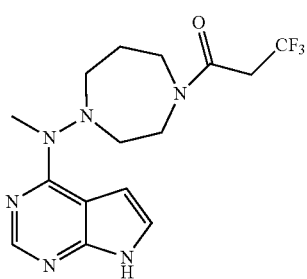
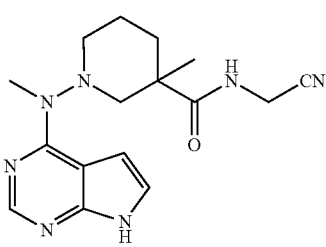
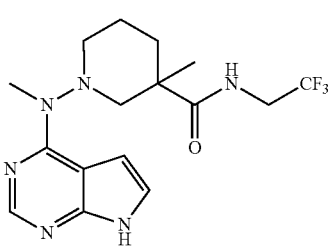
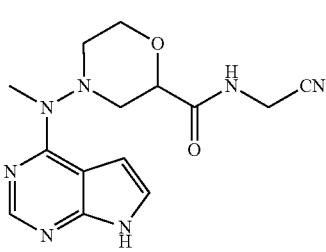
12
-continued
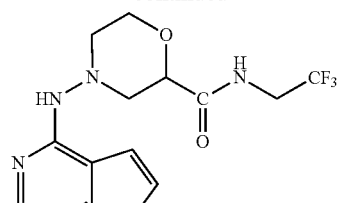
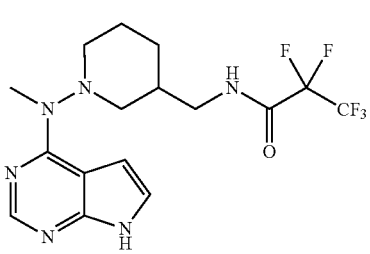

-continued

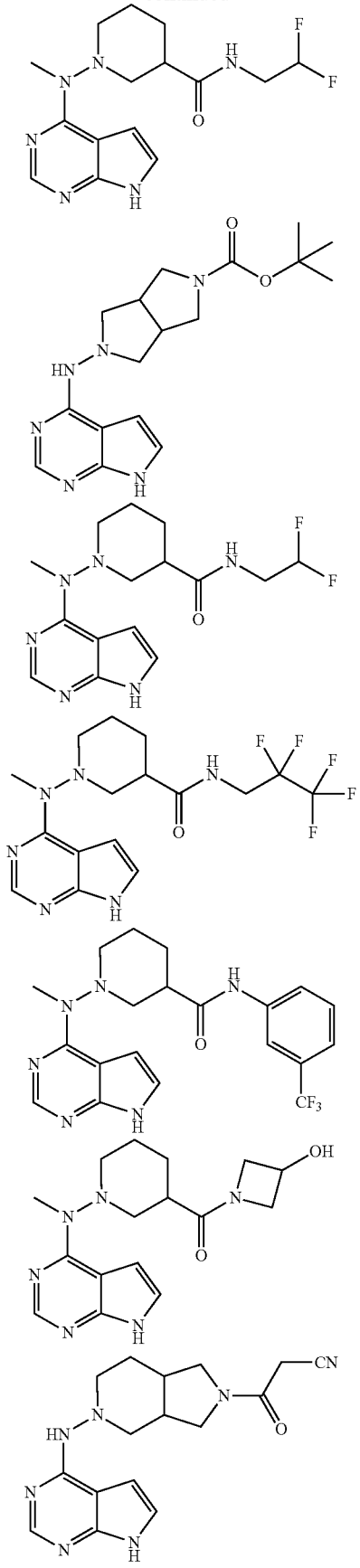

-continued

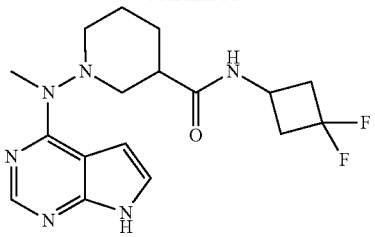

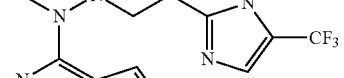

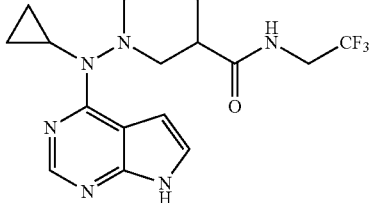

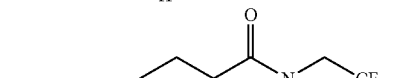

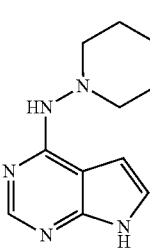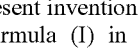

The present invention also provides use of the compound of the formula (I) in preparation of drugs for treating diseases related to JAK.

Definition

Unless otherwise indicated, the following terms and phrases used in the context have the following meanings. A particular term or phrase shall not be considered as being uncertain or unclear when there is no particular definition, and shall be understood according to the common meanings. When proprietary name is used herein, it is intended to refer to the corresponding commodity or the active ingredients thereof. $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; C3-12 is selected from $C_3$, $C_4$, $C_5$, $C_6$, $C_7$, $C_8$, $C_9$, $C_{10}$, $C_{11}$ and $C_{12}$.

$C_{1-12}$ alkyl or heteroalkyl, $C_{3-12}$ cyclic group or heterocyclic alkyl, $C_{1-12}$ alkyl or heteroalkyl substituted by $C_{3-12}$ cyclic alkyl or heterocyclic alkyl include but are not limited to:

$C_{1-12}$ alkyl, $C_{1-12}$ alkyl amino, N, N-di($C_{1-12}$ alkyl) amino, $C_{1-12}$ alkoxy, $C_{1-12}$ alkyl acyl, $C_{1-12}$ alkoxycarbonyl, $C_{1-12}$ alkyl sulfonyl, $C_{1-12}$ alkyl sulfinyl, $C_{3-12}$ cycloalkyl, $C_{3-12}$ cyclic alkyl amino, $C_{3-12}$ Heterocyclic alkyl amino, $C_{3-12}$ cyclic alkoxy, $C_{3-12}$ cyclic alkyl acyl, $C_{3-12}$ cyclic alkoxycarbonyl, $C_{3-12}$ cyclic alkyl sulfonyl, $C_{3-12}$ cyclic alkyl sulfinyl, 5~12 membered aryl or hereroaryl, 5~12 membered aralkyl or hereroaralkyl;

methyl, ethyl, n-propyl, isopropyl, —CH2C(CH3)(CH3)(OH), cyclopropyl, cyclobutyl, propyl methylene, cyclopropyl acyl, benzyloxy, trifluoromethyl, aminomethyl, hydroxymethyl, methoxyl, formyl, methoxycarbonyl, mesyl, methylsulfinyl, ethyoxyl, ethanoyl, ethyl sulfonyl, ethoxycarbonyl, dimethylamino, diethylamino, diethylamino carbonyl and diethylamino carbonyl;

$N(CH_3)_2$, $NH(CH)$, $—CH_2CF_3$, $—CH_2CH_2CH_3$, $—CH_2CH_2F$, $—CH_2CH_2S(=O)_2CH_3$, $—CH_2CH_2CN$,

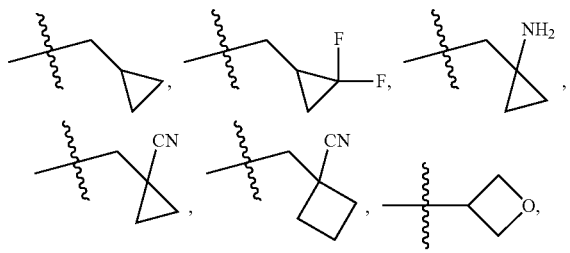

$—CH_2CH(OH)(CH_3)_2$, $—CH_2CH(F)(CH_3)_2$, $—CH_2CH_2F$, $—CH_2CF_3$, $—CH_2CH_2CF_3$, $—CH_2CH_2NH_2$, $—CH_2CH_2OH$, $—CH_2CH_2OCH_3$, $—CH_2CH_2CH_2OCH_3$, $—CH_2CH_2N(CH_3)_2$, $—S(=O)_2CH_3$, $—CH_2CH_2S(O)_2CH_3$; and phenyl, thiazoly, biphenyl, naphthyl, cyclopenty, furyl, 3-pyrroline, pyrrolidyl, 1,3-dioxolane, pyrazolyl, 2-pyrazolinyl, pyrazolidinyl, imidazolyl, oxazole, thiazolyl, 1, 2, 3-imidazolyl, 1, 2, 3-triazolyl, 1, 2, 4-triazolyl, 1, 3, 4-thiadiazole, 4H-pyranyl, pyridyl, piperidyl, 1,4-dioxane, morpholinyl, pyridazinyl, pyrimidyl, pyrazinyl, piperazinyl, 1, 3, 5-trithiane, 1, 3, 5-triazinyl, benzofuryl, benzo-thiophenyl, indolyl, benzimidazolyl, benzothiazolyl, purinyl, quinolyl, isoquinolyl, cinnoline or quinoxalinyl;

The term "pharmaceutically acceptable" used herein is to describe compounds, materials, combinations and/or formulation as they can be contacted with human and animal tissue within a reliable medical judgment range without overmuch toxicity, irritation and allergy y reactions, or other problems or complications, which is matched with the reasonable interest/risk.

The term "pharmaceutically acceptable salt" refers to the salt of the compound according to the present invention, which is prepared by the compound with particular substituent discovered by the present invention with relatively nontoxic acid or alkali. When the compound of the present invention contains relatively acidic functional group, the base addition salt can be obtained by contacting sufficient alkalit with the neutral form of this kind of compound in pure solution or proper inert solvent. The pharmaceutically acceptable base addition salt include sodium salt, potassium salt, calcium salt, ammonium salt, organic amino salt or magnesium salt, or similar salt. When the compound of the present invention contains relatively alkalic functional group, the acid addition salt can be obtained by contacting sufficient acid with the neutral form of this kind of compound in the pure solution or proper inert solvent. Examples of the pharmaceutically acceptable acid addition salt include inorganic acid salts, which include, e.g., hydrochloric acid, hydrobromic acid, nitric acid, carbonic acid, bicarbonate, phosphoric acid, hydrogen phosphate, dihydrogen phosphate, sulfuric acid, hydrogen sulfate, hydroiodic acid, phosphorous acid, etc.; and organic acid salt, the said organic acid salt include acetic acid, propionic acid, isobutyric acid, maleic acid, malonic acid, benzoic acid, succinic acid, suberic acid, fumaric acid, lactic acid, mandelic acid, phthalic acid, benzenesulfonic acid, para-toluenesulfonic acid, citric acid, tartaric acid, methanesulfonic acid, and other similar acids; and further include salts of amino acid (such as arginine), and the salts of glucuronic acid and other organic acids (Berge et al., "Pharmaceutical Salts", Journal of Pharmaceutical Science 66: 1-19 (1977)). Particular compound of the present invention contains alkaline and acidic functional group so as to be converted into any base or acid addition salt.

Preferably, the salt is contacted with the alkali or acid by conventional way, and then the parent compound is separated, thereby to prepare the neutral form of the compound. The parent form of the compound is different from the forms of various salts thereof in some physical properties, for example, the solubility is different in polar solvent.

The "pharmaceutically acceptable salt" used herein belongs to the derivatives of the compound of the present invention, wherein the parent compound is modified by acid addition or base addition forming salts. Examples of the pharmaceutically acceptable salt include but are not limited to: inorganic acid salt or organic acid salt of basic group, e.g. amine, and alkali metal or organic salt of acid, e.g. carboxylic acid, etc. The pharmaceutically acceptable salt includes regular non-toxic salt or quaternary ammonium salt of the parent compound, such as salts formed by non-toxic inorganic acid or organic acid. The regular non-toxic salt includes but is not limited to salts derived from the inorganic acid or organic acid, the said inorganic acid or organic acid is selected from 2-acetoxybenzoic acid, 2-hydroxyethylsulfonic acid, acetic acid, ascorbic acid, benzenesulfonic acid, benzoic acid, bicarbonate, carbonic acid, citric acid, edetic acid, ethane disulfonic acid, ethane sulfonic acid, fumaric acid, glucoheptose, gluconic acid, glutamic acid, glycollic acid, hydrobromic acid, hydrochloric acid, hydriodate, hydroxyl, hydroxynaphthoate, isethionic acid, lactic acid, lactin, dodecyl sulfonate, maleic acid, malic acid, mandelic acid, methane sulfonic acid, nitric acid, oxalic acid, pamoic acid, pantothenic acid, phenylacetic acid, phosphoric acid, poly-galacturonic, propionic acid, salicylic acid, stearic acid, ethylidene acid, succinic acid, sulfamic acid, sulfanilic acid, sulfuric acid, tannin, tartaric acid and para-toluenesulfonic acid.

The pharmaceutically acceptable salt of the present invention can be synthesised by the parent compound containing acid or basic group through a regular chemical process. Generally, the preparation of the salt is as follow: the compounds in free acid or free alkali form are reacted with stoichiometric proper alkali or acid in the water or organic solvent, or the mixture of them to prepare the salt. Generally, ether, ethyl acetate, ethanol, isopropanol or acetonitrile and other non-aqueous medias are preferable.

In addition to salt, the compound provided by the present invention also has prodrug form. The prodrug of the compound described herein can be easily converted to the compound of the present invention by undergoing chemical changes under physiological conditions. In addition, the prodrug can be converted into the compound of the present invention by chemical or biochemical way in vivo.

Some compounds of the present invention can be exist in non-solvated form or solvated form, including hydrate form. Generally speaking, the non-solvated form is equivalent to the solvated form, and both of them are in the scope of the present invention. Some compounds of the present invention can have asymmetric carbon (optical center) or double bond. Racemate, diastereoisomer, geometric isomer and single isomer are all within the scope of the present invention.

The graphic representation of racemate and individual possible stereoisomer; and t racemates mixture, inequality enantiomer mixture or the pure compound of enantiomer are from Maehr, J. CHem. Ed. 1985, 62:114-120. 1985, 62: 114-120. Unless otherwise indicated, an absolute configuration of a stereoscopic center is shown by wedge-shaped bond and dotted line bond. When the compound as described herein contains olefinic double bond or other geometrically asymmetric center, unless otherwise indicated, it include E and Z geometric isomers. Similarly, all the tautomeric forms are within the scope of the present invention within the scope of the present invention.

The compound of the present invention can have particular geometric isomers or stereoisomers. The present invention conceives all these compounds, including cis and trans isomers, (−)- and (+)-paired enantiomer, (R)- and (S)-enantiomer, diastereoisomer, (D)-isomer, (L)-isomer, and the racemate mixture thereof and other mixtures, such as the mixture enriched with enantiomers or diastereomers, all these mixtures are within the scope of the present invention. Other asymmetrical carbon may exist in substituents, e.g., alkyl. All these isomers and their mixtures are within the scope of the present invention within the scope of the present invention.

The (R)- and (S)-isomers, and D and L isomers with optical activity can be prepared by chiral synthesis, chiral reagent or other conventional technologies. An enantiomer of a particular compound of the present invention can be prepared by asymmetric synthesis or derivatization with chiral auxiliary, wherein the obtained diastereomer mixture is separated, and the auxiliary group is broken to provide pure enantiomer required. Alternatively, a molecule with alkaline functional group (such as amino) or acidic functional group (such as carboxyl) can form diastereoisomer salt with proper acid and alkali of optical activity, then resolution of diastereoisomer is conducted through the resolution method wellknown in the art, and then pure enantiomer is recovered. In addition, separation of enantiomer and diastereoisomer is conducted by chromatography, where chiral stationary phase is used, and optionally combined with chemical derivatization method (e.g., carbamate can be produced from amine).

The compound of the present invention may include atomic isotope of on one or more atoms of the compound in non-natural ratio. For example, the compound can be labeled by radio isotope, such as tritium ($^3H$), iodine-125($^{125}I$) or C-14($^{14}C$). All isotope variants of i the compound of the present invention, no matter radioactive or not, is within the scope of the present invention.

The term "pharmaceutically acceptable carrier" represent any agent or carrier medium which can deliver effective quantity of the present active compound without interfere the bioactivity thereof, and is of no toxicity or any side-effect to host or patient. Representative carriers include water, oil, vegetable and mineral, cream base, lotion base, ointment base, and etc. These materials include suspending agent, tackifier, transdermal enhancer, and etc. Their formulation are wellknown by those skilled in the cosmetic field or topical medicine field. For other information about carrier, refer to Remington: The Science and Practice of Pharmacy, 21th Ed., Lippincott, Williams & Wilkins (2005), which is incorporated herein by reference.

The term "excipient" generally refers to the carrier, diluent and/or media required for preparing effective medical composition.

Regarding to the medicine or pharmacology active agent, the term "effective amount" or "therapeutically effective amount" refers to the amount of the the drug which is sufficient to achieve the expected effect without toxicity. Regarding to the oral formulation of the present invention, the "effective amount" of an active agent in the composition refers to the amount required to achieve the expected effect when combined with another active agent in the composition. The effective amount varys with each individual, and depends on the age and general condition of the subject, and also depends on the particular active agent. The proper effective amount in individual case can be determined by conventional test by those skilled in the art.

The term "active ingredient", "therapeutic agent", "active substance" or "active agent" refers to a chemical entity that can effectively treat the target disorders, diseases or conditions.

The term "substituted" refers to any one or more hydrogen atoms on a particular atom replaced by a substituent or several substituents, including heavy hydrogen and variants of hydrogen, on condition that the valence state of the particular atom is normal and the substituted compound is stable. When the substituent is keto group (that is =O), it means that two hydrogen atoms are replaced. The ketone replacement will not occur on aryl. The term "optionally substituted" means it may be replaced and may not be replaced. Unless otherwise indicated, the type and number of the substituent can be optional as long as can be realized chemically.

When any variate (such as R) appears more than once on the compound, definition thereof under each condition is independent. Therefore, for example, if a group is replaced by 0 to 2 R, then the group can be optionally replaced by two R at the most, and the R under each condition has an independent option. In addition, the combination of the substituent and/or variants thereof is allowed only under the condition that the combination can generate stable compound.

When the bonds of a substituent can be crosswise connected to two atoms on a ring, the substituent can be bonded with any atom on the ring. When there is no indication show that through which atom the illustrated substituent is connected to the compound included in the general formula of the chemical structure but is not specifically described, the substituent can be bonded to any atom. The combination of the substituent and/or variant thereof is allowed only under the condition that the combination may generate stable compound. For example, the structure unit

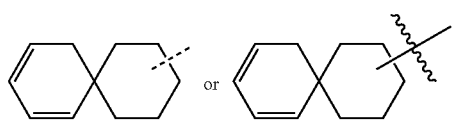

indicate that it may be substituted on any position of the cyclohexyl or the cyclodiene.

The substituent of alkyl and hereroalkyl is generally called "aryl substituent", and they can be selected from but not limited to one or more of the following groups: —R', OR', =O, =NR', =N—OR', —NR'R", —SR', halogen, —SiR'R"R''', OC(O)R', —C(O)R', —CO$_2$R', —CONR'R", —OC(O)NR'R", —NR"C(O)R', NR'C(O)NR"R''', —NR"C (O)₂R', —NR''''-C(NR'R''R''')=NR'' '', NR''''C(NR'R'')=NR''', —S(O)R', —S(O)₂R', —S(O)₂NR'R'', NR''SO₂R', —CN, —NO₂, —N₃, —CH(Ph)₂ and fluoro (C₁-C₄) alkyl, and the number of the substituent is 0 to (2m'+1), wherein m' is the total number of carbon atoms in these groups. R', R'', R''', R'''' and R''''' are independently selected from hydrogen, substituted or unsubstituted hereroalkyl, substituted or unsubstituted aryl (such as the aryl substituted by 1 to 3 halogens), substituted or unsubstituted alkyl, alkoxy, sulfo-alkoxy or aralkyl. When the compound of the present invention includes more than one R, for example, each R is independently selected, just as being each group of them when there are more than one R', R'', R''', R'''' and R'''''. When R' and R'' attach to the same nitrogen atom, they may combine with the nitrogen atom to form 5-, 6- or 7-membered ring. For example, —NR'R'' is intended to include but not limited to 1-pyrrolidyl and 4-morpholinyl. According to the discussion about the substituent above, those skilled in the art can understand that the term "aryl" is intended to include the group formed by carbon atom bonded with non-hydrogen group, such as haloalkyl (such as —CF₃ and —CH₂CF₃) and acyl (such as —C(O)CH₃, —C(O)CF₃, —C(O)CH₂CH₃ etc.).

Similar to the substituent of alkyl, substituent of aryl and hereroaryl substituent is generally called "aryl substituent", which is selected from, e.g. —R', —OR', —NR'R'', —SR', -halogen, —SiR'R''R''', OC(O)R'. —C(O)R'. —CO₂R', —CONR'R'', —OC(O)NR'R'', —NR''C(O)R', NR' C(O)NR''R''', —NR''C(O)₂R'. —NR''''-C(NR'R''R''')=NR'''', NR'''' C(NR'R'')=NR''', —S(O)R', —S(O)₂R'. —S(O)₂NR'R'', NR''SO₂R', —CN, —NO₂, —N₃, —CH(Ph)₂, fluoro(C₁-C₄)alkoxy and fluoro(C₁-C₄)alkyl, etc., the number of the substituent is between 0 to the total number of open valence on the aromatic ring; wherein, R', R'', R''', R'''' and R''''' are independently selected from hydrogen, substituted or unsubstituted alkyl, substituted or unsubstituted hereroalkyl, substituted or unsubstituted aryl, and substituted or unsubstituted hereroaryl. When the compound of the present invention includes more than one R, for example, each R is independently selected, just as being each group of them when there are more than one R', R'', R''', R'''' and R'''''.

Two substituents on the adjacent atoms of aryl or hereroaryl can be substituted by the substituent with general formula of -T-C(O)—(CRR')q-U— optionally, wherein T and U are independently selected from —NR, —O—, CRR'— or single bond, and q is integer from 0 to 3. Alternatively, two substituents on the adjacent atoms of aryl or hereroaryl can be substituted by the substituent with general formula of -A(CH₂)rB— optionally, wherein A and B are independently selected from —CRR'—, —O—, —NR—, —S—, —S(O)—, —S(O)₂—, —S(O)₂NR'— or single bond, and r is integer from 1 to 4. Optionally, the single bond on a new ring formed can be replaced by double bond. Alternatively, two substituents on the adjacent atom of aryl or hereroaryl can be substituted by the substituent with general formula of -A(CH₂)rB— optionally, wherein s and d are independently selected from an integer from 0 to 3, and X is —O—, —NR', —S—, —S(O)—, —S(O)₂— or —S(O)₂NR'—. Substituents R, R', R'' and R''' are independently selected from hydrogen and substituted or unsubstituted (C₁-C₆)alkyl.

Unless otherwise indicated, the term "halo-" or "halogen" itself or as a part of other substituent represent fluorine, chlorine bromine or iodine atom. In addition, the term "halo alkyl" is intended to include single halogenated alkyl and polyhalogenated alkyl. For example, the term "halo (C₁-C₄) alkyl" is intended to include but not limited to trifluoromethyl, 2, 2, 2-trifluoroethyl, 4-chlorobutyl, 3-brominepropyl, etc.

Examples of haloalkyl include, but are not limited to: trifluoromethyl, trichloromethyl, pentafluoroethyl, and pentachloroethyl. "Alkoxy" represents the above-mentioned alkyl having a particular number of carbon atoms bonded by oxygen bridge. C₁₋₆ alkoxy includes alkoxyl of C₁, C₂, C₃, C₄, C₅ and C₆. Examples of alkoxy include, but are not limited to: methoxy, ethoxy, n-propoxy, isopropoxy, n-butoxy, sec-butoxy, tert-butoxy, n-pentyloxy and S-pentyloxy. "Cycloalkyl" includes saturated cyclic group, such as cyclopropyl, cyclobutyl or cyclopentyl. 3-7 cycloalkyl includes C₃, C₄, C₅, C₆ and C₇ cycloalkyl. "Alkenyl" includes linear or branched hydrocarbon chain, wherein one or more carbon-carbon double bonds, such as vinyl and propenyl, are present at any stable site on the chain.

The term "halo" or "halogen" means fluorine, chlorine, bromine and iodine.

Unless otherwise specified, the term "hetero" means heteroatom or heteroradical (i.e., radical containing heteroatoms), including atoms other than carbon (C) and hydrogen (H) and the radical containing thereof, for example, including oxygen (O), nitrogen (N), sulphur (S), silicon (Si), germanium (Ge), aluminum (Al), boron (B), —O—, —S—, =O, =S, —C(=O)O—, —C(=O)—, —C(=S)—, —S(=O), —S(=O)₂—, and optionally substituted —C(=O)N(H)—, —N(H)—, —C(=NH)—, —S(=O)₂N(H)— or —S(=O)N(H)—.

Unless otherwise specified, "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes single ring, a linked ring, a spiro ring, and a fused ring or a bridged ring. The number of atoms on the ring is usually defined as the member number of rings, for example, "5~7 membered ring" refers to the surrounding arrangement of 5~7 atoms. Unless otherwise specified, the ring optionally contains 1~3 heteroatoms. Therefore, the term of "5~7 membered ring" includes, for example, phenylpyridine and piperidinyl; and, on the other hand, the term "5~7 membered heterocyclic alkyl ring" includes pyridyl and piperidinyl, but does not include phenyl. The term "ring" also includes a ring system containing at least one ring, wherein each "ring" independently meets the above-mentioned definition.

Unless otherwise specified, the term of "heterocyclo" or "heterocycle" means a stable monocyclic ring, bicyclic ring or tricycle containing heteroatom or hetero atomic group, which can be saturated, partially unsaturated or unsaturated (aromatic), and which contain carbon atoms and 1, 2, 3 or 4 ring heteroatoms independently selected from N, O and S, wherein any of said heterocycles may be fused to a benzene ring to form a dicyclo ring. Nitrogen and sulfur heteroatoms can be optionally oxidized (i.e., NO and S(O) p). Nitrogen atom may be substituted or unsubstituted (i.e., N or NR, wherein R is H or other substituent already be defined herein). The heterocyclic ring may be attached to the side groups of any heteroatom or carbon atom to form a stable structure. If the generated compound is stable, the heterocycles described herein may undergo substitutions at the carbon or nitrogen positions. The nitrogen atom on the heterocycle is optionally quaternized. In a preferred embodiment, when the total number of S and O atoms in the heterocycle exceeds 1, these heteroatoms are not adjacent to each other. In another preferred embodiment, the total number of S and O atoms in the heterocycle does not exceed 1. As used herein, the term "aromatic heterocyclo" or "heteroaryl" means stable 5 membered monocyclic ring or bicyclic ring, 6 membered monocyclic ring or bicyclic ring, 7 membered monocyclic ring or bicyclic ring, or aromatic cycle containing 7,8,9 or 10 membered bicyclic heterocyclyl, which contains carbon atoms and 1, 2, 3 or 4 heteroatoms independently selected from N, O and S. The nitrogen atom may be substituted or unsubstituted (i.e., N or NR, wherein R is H or other substituent already defined herein). Nitrogen and sulfur heteroatoms may be optionally oxidized (i.e., NO and S(O) p). It should be noted that the total number of S and O atoms on the aromatic heterocycle does not exceed 1. The bridged ring is also included in the definition of the heterocycle. A bridged ring is formed when one or more atoms (i.e., C, O, N, or S) are bonded to two non-adjacent carbon atoms or nitrogen atoms. The preferred bridged rings include, but are not limited to, one carbon atom, two carbon atoms, one nitrogen atom, two nitrogen atoms and one carbon-nitrogen group. It should be noted that one bridge always converts the monocyclic ring into the tricyclic ring. In the bridged ring, the substituents on the ring can also appear on the bridge.

Examples of heterocyclic compounds include, but are not limited to, acridinyl, azocine, benzimidazolyl, benzofuranyl, benzothiolfuranyl, benzothiolphenyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromene, cinnolinyl decahydroquinolyl, 2H, 6H-1,5,2-dithiazinyl, dihydrofuro [2,3-b] tetrahydrofuranyl, furyl, furazanyl, imidazolidinyl, imidazolinyl, imidazolyl, 1H-indazolyl, indolealkenyl, dihydro-indolyl, indolizinyl, indolyl, 3H-indolyl, isatinoyl, isobenzofuranyl, pyran, isoindolyl, isoindolinyl, isoindolyl, indolyl, isoquinolyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, isoxazolyl, oxindolyl, pyrimidinyl, phenanthridinyl, phenanthrolinyl, phenazine, phenothiazine, benzoxanthine, phenoxazinyl, phthalazinyl, piperazinyl, piperidinyl, piperidone, 4-piperidone, piperonyl, pteridinyl, purinyl, pyranyl, pyrazinyl, pyrazolidinyl, pyrazolinyl, pyrazolyl, pyridazinyl, pyridoxazoles, pyridinedimidazoles, pyridoxiazoles, pyridyl, pyrimidinyl, pyrrolidyl, pyrrolinyl, 2H-pyrrolyl, pyrrolyl, pyrazolyl, quinazolinyl, quinolyl, 4H-quinolizinyl, quinoxalinyl, quinuclidinyl, tetrahydrofuranyl, tetrahydroisoquinolyl, tetrahydroquinolyl, tetrazolyl, 6H-1,2,5-thiadiazinyl, 1,2,3-thiadiazolyl, 1,2,4-thiadiazolyl, 1,2,5-thiadiazinyl, 1,3,4-thiadiazinyl, thianthrenyl, thiazolyl, isothiazolylthienyl, thienyl, thienooxazolyl, thienothiazolyl, thienoimidazolyl, thienyl, triazinyl, 1,2,3-triazolyl, 1,2,4-triazolyl, 1,2,5-triazolyl, 1,3,4-triazolyl, and xanthenyl. The examples further include fused ring and spiro ring compound.

Unless otherwise indicated, the term "alkyl" or the subordinate concept (such as alkyl, alkenyl, alkynyl, phenyl, etc.) itself or as a part of other substituent represents hydrocarbon atomic groups or the combination thereof of the linear chain, branched chain or ring, it can be completely saturated, or unsaturated on single member or multiple members, can be single-substituted, double-substituted or multiple substituted, can be mono valent (such as methyl), divalent (such as methylene), or multivalent (such as methine), and can include divalent or multivalent atomic group, with carbon atoms of appointed quantity (such as $C_1$-$C_{10}$ which represents 1 to 10 carbons). "Alkyl" include but is not limited to aliphatic hydrocarbyl and aryl hydrocarbyl. The aliphatic hydrocarbyl includes chain and ring forms, and in particular, includes but not limits to alkyl, alkenyl an alkynyl, and the aryl hydrocarbyl includes but not limits to 6~12 membered aryl hydrocarbyl, such as benzene, naphthalene, etc. In some embodiments, the term "alkyl" indicates linear chain and branched chain atomic group or their combination thereof, it can be completely saturated, or unsaturated in single member or multiple members, and may include divalent or multivalent atomic group. Examples of the saturated hydrocarbon radical include but not limited to methyl, ethyl, n-propyl, isopropyl, n-butyl, tert-butyl, isobutyl, sec-butyl, isobutyl, cyclohexyl, (cyclohexyl) methyl, cyclopropyl methyl, and n-amyl, n-hexyl, n-heptyl, n-octyl, etc., and homologs or isomers thereof. The unsaturated alkyl has one or more double bond or triple bond, examples thereof include but not limited to vinyl, 2-propenyl, butenyl, crotyl, 2-isopentenyl, 2-(butadienyl), 2, 4-pentadienyl, 3-(1, 4-pentadienyl), acetenyl, 1- and 3-propinyl, 3-butynelene, and high homologs or isomers.

Unless otherwise indicated, the term "hereroalkyl" or the subordinate concept (such as hereroalkyl, hereroalkenyl, hereroalkynyl, hereroaryl, etc.) itself or combined with another term represent the stable hydrocarbon group or the combination thereof of the linear chain, branched chain or ring, which is formed by a particular number of carbon atoms and at least one heteroatom. In some embodiments, the term "hereroalkyl" itself o combined with another term to represent the stable hydrocarbon radical or the combination thereof of the linear chain, branched chain or ring, which is formed by a certain number of carbon atoms and at least one heteroatom. In a particular embodiment, the heteroatom is selected from B, O, N and S, wherein the nitrogen and sulphur atoms are oxidized optionally, and the nitrogen heteroatom quaternized optionally. The heteroatom B, O, N and S can be at any internal position of the hereroalkyl (including the position where the alkyl attaches on rest part of the molecule). Examples include but not limited to —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —CH$_2$—CH═N—OCH$_3$ and —CH═CH-n(CH$_3$)—CH$_3$. At most two heteroatoms can be continuous, such as —CH$_2$—NH—OCH$_3$.

The term "alkoxy", "alkyl amino" and "alkyl sulphanyl" (or sulfo-alkoxy) are conventional expression, which refer to the alkyl group connected to the rest part of the molecular through an oxygen atom, amidogen or sulphur atom.

Unless otherwise indicated, the term "cycloalkyl", "heterocycle alkyl" or the subordinate concept (such as aryl, heteroaryl, cycloalkyl, heterocyclo alkyl, cycloalkenyl, heterocyclo alkenyl, cycloalkynyl, heterocyclp alkynyl, etc.) itself or combined with other terms respectively represents cyclized "alkyl" and "heteroalkyl". In addition, regarding to the heteroalkyl or heterocyclo alkyl (such as heteroalkyl and heterocyclo alkyl), the heteroatom may occupy the position where the heterocycle attaches to the rest part of the molecule. Examples of the cycloalkyl include but not limit to cyclopentyl, cyclohexyl, 1-cyclohexenyl, 3-cyclohexenyl, cycloheptyl, and etc. Non-restrictive examples of the heterocyclyl include 1-(1, 2, 5, 6-tetrahydropyridine), 1-piperidyl, 2-piperidyl, 3-piperidyl, 4-morpholinyl, tetrahydrofuran-2-yl, tetrahydrofuran indole-3-yl, thiophane-2-yl, thiophane-3-yl, 1-piperazinyl and 2-piperazinyl.

Unless otherwise specified, term "aryl" refers to polyunsaturated aromatic substituent, which can be monosubstituted, bi-substituted or polysubstituted, and can be monovalent, divalent or multivalent, and can be monocyclic or polycyclic (such as monocyclic to tricyclic; wherein, at least one ring is aromatic), and they are fused together or in covalent linkage. Term "heteroaryl" refers to aryl (or ring) containing 1-4 heteroatoms. In an illustrative example, heteroatom is selected from B, N, O and S, wherein nitrogen and sulphur atom are optionally oxidized, and nitrogen atom is optionally quaternized. Heteroaryl can be connected to other parts of a molecule via heteroatom. Non-restrictive examples of aryl and heteroaryl include 1-naphthyl, 2-naphthyl, 4-biphenyl, 1-pyrryl, 2-pyrryl, 3-pyrryl, 3-pyrazolyl, 2-imidazolyl, 4-imidazolyl, pyrazinyl, 2-oxazolyl, 4-oxazolyl, 2-benzyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. Substituent of any above aryl and heteroaryl ring is selected from acceptable substituent stated hereinafter.

For convenience, when aryl is used together with other terms (such as aryloxy, arylthio and aralkyl) includes aryl and heteroaryl ring as defined above. Thus, term "aralkyl" is meant to include those atomic groups with aryl attached to alkyl (such as benzyl, phenethyl, pyridyl methyl, etc.), and includes those alkyls with carbon atom (such as methylene) have already been substituted by, for example, oxygen atom, such as phenoxymethyl, 2-pyridine oxygen methyl, 3-(1-naphthoxy) propyl, etc.

Term "leaving group" refers to functional group or atom that can be substituted by another functional group or atom via substitution (such as nucleophilic substitution). For example, representative leaving group includes triflate; chlorine, bromine and iodine; sulfonate, such as methanesulfonate, toluenesulfonate, p-bromobenzene sulfonate, p-toluenesulfonate; acyloxy, such as acetoxyl and trifluoroacetyl.

Term "protecting group" includes but not limited to "amino protecting group", "hydroxyprotecting group" or "sulfydrylprotecting group". Term "amino protecting group" refers to protecting group that is suitable for preventing side reaction on amino nitrogen. Representative amino protecting group includes but not limited to: formyl; acyl, such as chain alkanoyl (such as acetyl, trichloroacetyl and trifluoroacetyl); alkoxy carbonyl, such as t-Butyloxy carbonyl(Boc); aryl methoxycarbonyl, such as carbobenzoxy(Cbz) and 9-fluorenylmethoxycarbonyl(Fmoc); arylmethyl, such as benzyl (Bn), triphenylmethyl(Tr), 1,1-di-(4'-methoxyphenyl) methyl; silicyl, such as trimethylsilyl(TMS) and t-butyl dimethysilyl(TBS). Term "hydroxyprotecting group" refers to protecting group that is suitable for preventing side reaction of hydroxyl. Representative hydroxy protecting group includes but not limited to: alkyl, such as methyl, ethyl and ter-butyl; acyl, such as alkane acyl (such as acetyl); arylmethyl, such as benzyl(Bn), p-methoxybenzyl(PMB), 9-fluorenylmethyl(Fm) and diphenyl methyl (benzhydryl, DPM); silicyl, such as trimethylsilyl(TMS) and t-butyl dimethysilyl(TBS).

The compound of the present invention j can be prepared through a plurality of synthetic methods known by those skilled in the art, including detailed embodiments listed below, the embodiments formed by combination of the said detailed embodiments and other chemical synthesis methods, and equivalent replacement known by those skilled in the art. The preferable embodiments include but not limited to the embodiments of the present invention.

The solvent used in the present invention is commercially available. The following abbreviations are used in the present invention: aq represents water; HATU represents O-(7-aza-benzotriazole-1-yl)-N, N, N', N'-tetramethylurea hexafluorophosphate; EDC represents N-(3-dimethylaminopropyl)-N'-ethyl carbodiimide hydrochloride; m-CPBA represents 3-chlorine peroxy-benzoic acid; eq represents equivalent weight and equivalent; CDI represents carbonyl diimidazole; DCM represents dichloromethane; PE represents petroleum ether; DIAD represents azo-dicarboxylic acid diisopropyl ester; DMF represents N, N-dimethyl formamide; DMSO represents dimethylsulfoxide; EtOAc represents ethyl acetate; EtOH represents ethyl alcohol; MeOH represents methyl alcohol; CBz represents carbobenzoxy, which is an amine protecting group; BOC represents tertiary butyl carbonyl, which is an amine protecting group; HOAc represents acetic acid; NaCNBH$_3$ represents sodium cyanoborohydride; r.t. represents ambient temperature; O/N represents overnight; THF represents tetrahydrofuran; Boc$_2$O represents ditertiary butyl dicarbonic ester; TFA represents trifluoroacetic acid; DIPEA represents diisopropyl ethylamine; SOCl$_2$ represents thionyl chloride; CS$_2$ represents carbon disulfide; TsOH represents p-toluenesulfonic acid; NFSI represents N-fluoro-N-(benzenesulfonyl) benzsulfamide; NCS represents 1-chloro pyrrolidine-2, 5-diketone; n-Bu$_4$NF represents fluoro-tetrabutyl ammonium; iPrOH represents 2-propyl alcohol; mp represents melting point; LDA represents lithium diisopropyl amide; TLC represents the thin-layer chromatography; MS ESI represents the electrospray ionization mass spectrum; DCM represents dichloromethane; LCMS represents the liquid chromatography-mass spectrometry; SFC represents supercritical fluid chromatography; DMF represents N, N-dimethylformamide; HOBt represents 1-hydroxy benzotriazole; and EDCI represents 1-(3-dimethylamino propyl)-3-ethyl carbodiimide hydrochloride.

The compound is named manually or by ChemDraw® software, and the compound commercially availablet use the name in vendor catalog.

DETAILED DESCRIPTION

In order to illustrate the present invention in further details, the following embodiments are presented, but the scope of the present invention is not limited to them.

Synthesis of key intermediate 1, intermediate 2 and intermediate 3:

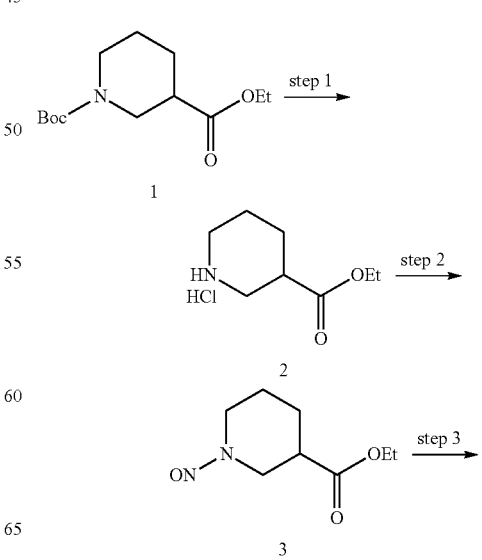

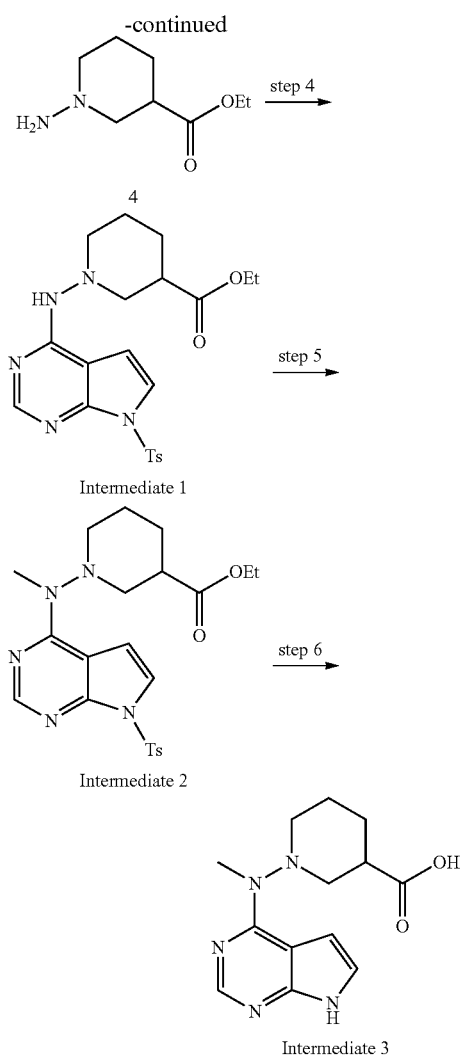

Step 1: Hydrochloric acid/dioxane (10 M, 200 mL) was dropwise added into solution (50 mL)ethyl 1-Boc-piperidyl-3-carboxylate (50 g, 194.30 mmol) in DCM at 0° C., then the reaction solution was warmed up to 25° C. and stirred for 2 h. TLC showed that the reaction was completed. The mixture was concentrated under reduced pressure to obtain ethylpiperidyl-3-carboxylate hydrochloride which was yellow solid (42.63 g, crude product). The product was directly used in next step without further purification. The value of $C_8H_{15}NO_2[M+H]^+$ 158 was calculated using MS ESI, and was 158.

Step 2: ethyl piperidyl-3-carboxylate hydrochloride (40.00 g, 206.54 mmol) was dissolved in a mixed solvent of glacial acetic acid (400 mL) and water (200 mL), and a water solution (200 mL) of sodium nitrite (28.50 g, 413.08 mmol) was dropwise added (30 min) at 0° C. After the water solution was dropwise added, the mixture was stirred and reacted for 1 h at 0° C. Afterwards, the reaction solution was heated to 25° C. and then stirred for 1 h again. TLC (petroleum ether:ethyl acetate=5:1) showed that the raw materials are completely reacted. The reactants were quenched by water, and then extracted using ethyl acetate (100 mL×2). The merged organic phases were washed by saturated sodium hydrogen carbonate solution (100 mL×3) and saturated saline solution (100 mL×2) respectively, dried by anhydrous sodium sulfate, filtered, and concentrated under reduced pressure. Residues were purified by a silica column chromatography (petroleum ether:ethyl acetate=5:1) to obtain 1-nitrosopiperidyl-3-carboxylic acid ethyl ester which was colorless oily matter (31.00 g, yield was 80.60%). The value of $C_8H_{14}N_2O_3[M+H]^+$ 187 was calculated using MS ESI, and was 187.

Step 3: Ethyl 1-nitrosopiperidyl-3-carboxylate (10.00 g, 53.70 mmol) and zinc dust (17.56 g, 268.50 mmol) were dissolved in methanol (80 mL), and cooled to −5° C., and then glacial acetic acid (80 mL) was dropwise added. The mixture obtained was stirred for 30 min at 0° C., then was warmed up to 25° C. and stirred to react for 2 h. TLC showed that the reaction was completed. Solids were filtered out, and the filtrate was concentrated under reduced pressure. The residues were adjusted by saturated sodium hydrogen carbonate solution to pH=7-8, and an aqueous phasemL× was extracted by dichloromethane/methanol (5:1) (100 mL×3). The merged organic phases were washed by saturated sodium chloride solution (50 mL×3), dried by anhydrous sodium sulfate, filtered and concentrated under reduced pressure to obtain 1-aminopiperidyl-3-carboxylic acid ethyl ester which was buff oily matter (6.50 g, crude product). The product was directly used in next step without further purification. The value of $C_8H_{16}N_2O_2[M+H]^+$ 173 was calculated using MS ESI, and was 173.

Step 4: Ethyl 1-aminopiperidyl-3-carboxylate (6.50 g, 37.74 mmol) and 4-cloro-7-tosyl-7H-pyrrolo[2,3-d]pyrimidine (12.78 g, 41.51 mmol) were dissolved in DCM (60 mL). Triethylamine (11.46 g, 113.22 mmol) was added into the foregoing solution at 25° C. The mixed solution was stirred to react for 10 h at 25° C. TLC showed that the reaction was completed. The mixture was concentrated to be dry under reduced pressure. Residues were poured into water (100 mL), and the aqueous phase was extracted using ethyl acetate (100 mL×2). Consolidated organic phases were washed by saturated saline solution (50 mL×2), dried by anhydrous sodium sulfate, filtered and concentrated to be dry under reduced pressure. Residues were purified by silica column chromatography (dichloromethane:ethyl acetate=1:0 to 2:1) to obtain 1-((7-tosyl-7H-pyrrolo[2,3-d]pyrimidine-4-yl)amino)piperidyl-3-carboxylic acid ethyl ester which was white spumescent solid (5.60 g, wherein the yield was 33.47%). Residues were purified by silica column chromatography (dichloromethanedichloromethane:ethyl acetate=1:0 to 2:1) to obtain 1-((7-p-tosyl-7H-pyrrolo[2,3-d]pyrimidine-4-yl) amino) piperidyl-3-carboxylic acid ethyl ester which was white spumescent solids (5.60 g, the yield was 33.47%). The value of $C_{21}H_{25}N_5O_4S[M+H]^+$ 444 was calculated using MS ESI, and was 444.

Step 5: Ethyl 1-[[7-(tosyl)pyrrolo[2,3-d]pyrimidin-4-yl]amino]piperidyl-3-carboxylate (2.00 g, 4.51 mmol) was dissolved in tetrahydrofuran (30 mL), and NaH (60%, 270.80 mg, 6.77 mmol) was added in batches at 0° C., then the mixture was warmed up to 28° C. and stirred for 30 min. Afterwards, the reaction system was cooled to 0° C., and methyl iodide (960.22 mg, 6.77 mmol) was dropwise added; then the reaction system was warmed up to 28° C. and was stirred to react for 2 h at the same temperature. LCMS and TLC showed that the reaction was completed. The reaction solution was quenched by water (5 mL), and an aqueous phase was extracted using ethyl acetate (20 mL×3). The merged organic phases were washed by saturated saline solution (15 mL×2), dried by anhydrous sodium sulfate, filtered and concentrated to be dry under reduced pressure. Residues were purified by silica column chromatography (petroleum ether:ethyl acetate=5:1, 3:1) to obtain ethyl 1-[methyl-[7-(tosyl)pyrrolo[2,3-d]pyrimidin-4-yl]amino]piperidyl-3-carboxylate which were white spumescent solid (900.00 mg, wherein the yield was 41.43%). The value of $C_{22}H_{27}N_5O_4S[M+H]^+$ 458, was calculated using MS ESI, and was 458.

Step 6: Ethyl 1-[methyl-[7-(tosyl)pyrrolo[2,3-d]pyrimidin-4-yl]amino]piperidyl-3-carboxylate (900.00 mg, 1.97 mmol) was dissolved in a mixed solvent of methanol (8 mL), THF(8 mL) and water (4 mL), and sodium hydroxide (315.20 mg, 7.88 mmol) was added, then the mixture was heated to 70° C. and stirred for 1 h. TLC showed that the reaction was completed. The solvent was concentrated to be dry under reduced pressure, and residues were adjusted by 2 M hydrochloric acid (4 mL) to pH=3-4. An aqueous phase was subjected to vacuum concentration to obtain 1-[methyl (7H-pyrrolo[2,3-d]pyrimidin-4-yl)amino]piperidyl-3-carboxylic acid which was white solid (650.00 mg, crude product). The product was directly used in next step without further purification. The value of $C_{13}H_{17}N_5O_2[M+H]^+$ 276 was calculated using MS ESI, and was 276.

Embodiment 1

WX01

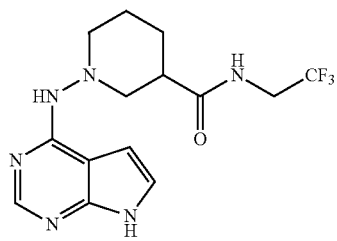

1-((7H-pyrrolo[2,3-d]pyrimidin-4-yl)amino)-N-(2,2,2-trifluoroethyl)piperidyl-3-formamide

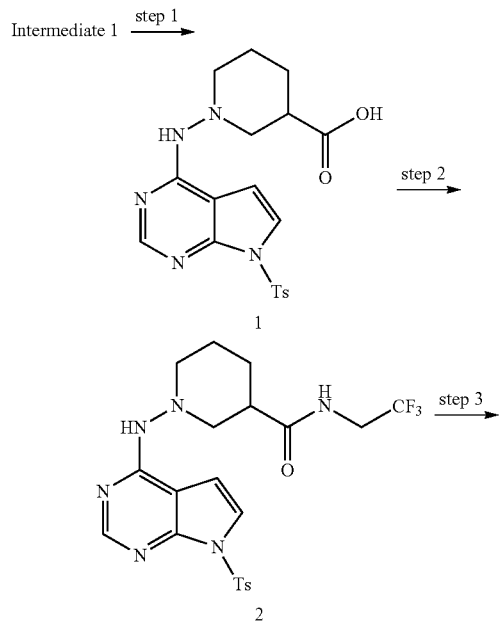

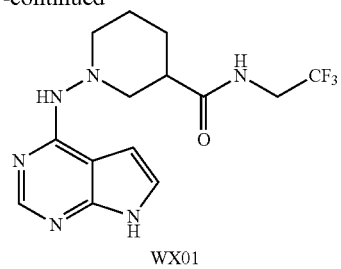

WX01

Step 1: Intermediate 1 (270.00 mg, 608.77 umol) was dissolved in a mixed solvent of tetrahydrofuran (5 mL) and water (3 mL), lithium hydroxide monohydrate (51.09 mg, 1.22 mmol) was added in batches at 25° C., and was stirred to react for 5 h at 25° C. LCMS and TLC showed that the reaction was completed. The reaction solution was concentrated to be dry under reduced pressure, and the aqueous phase was adjusted by 2 M HCl (3 mL) to pH=2-3, and extracted by ethyl acetate (10 mL×2). Merged organic phases were washed by saturated saline solution (10 mL), dried by anhydrous sodium sulfate, filtered and concentrated in vacuum to obtain 1-((7-tosyl-7H-pyrrolo[2,3-d]pyrimidin-4-yl)amino)piperidyl-3-carboxylic acid which was yellow oily matter (200.00 mg, crude product). The value of $C_{19}H_{21}N_5O_4S[M+H]^+$ 416 was calculated using MS ESI, and was 416.

Step 2: 1-((7-tosyl-7H-pyrrolo[2,3-d]pyrimidin-4-yl)amino)piperidyl-3-carboxylic acid (200.00 mg, 481.38 umol) was dissolved in DMF (10 mL), and then HOBt (130.09 mg, 962.76 umol), EDCI (184.56 mg, 962.76 umol), triethylamine (292.27 mg, 2.89 mmol) and 2,2,2-trifluoroethylamine (95.36 mg, 962.76 umol) were added at 0° C. The mixture was warmed up to 25° C. and stirred for 10 h. LCMS showed that the reaction was completed. The reaction solution was poured into water (30 mL), and the aqueous phase was extracted using ethyl acetate (15 mL×2). Merged organic phases were washed by saturated saline solution (10 mL×2), dried by anhydrous sodium sulfate, filtered and concentrated in vacuum. Residues were purified through a prep-TLC (ethyl acetate:petroleum ether=1:10) to obtain 1-((7-tosyl-7H-pyrrolo[2,3-d]pyrimidine-4-yl) amino)-N-(2,2,2-trifluoroethyl)piperidyl-3-formamide which was yellow oily matter (40.00 mg, yield was 16.74%). The value of $C_{21}H_{23}F_3N_6O_3S[M+H]^+$ 497 was calculated using MS ESI, and was 497.

Step 3: 1-((7-tosyl-7H-pyrrolo[2,3-d]pyrimidin-4-yl)amino)-N-(2,2,2-trifluoroethyl)piperidyl-3-formamide (40.00 mg, 80.56 umol) was dissolved in MeOH (3 mL) and water (3 mL), potassium carbonate (22.27 mg, 161.12 umol) was added at 25° C., and then the reaction solution was heated to 70° C. and stirred for 2 h. LCMS showed that the reaction was completed. A mixture was cooled to 25° C. and concentrated to be dry under reduced pressure. The aqueous phase was extracted using ethyl acetate (10 mL×2). Merged organic phases were washed by saturated saline solution (10 mL), dried by anhydrous sodium sulfate, filtered and concentrated in vacuum. Residues were purified through a prep-TLC (dichloromethane:methanol=10:1) to obtain WX01: 1-((7H-pyrrolo[2,3-d]pyrimidin-4-yl)amino)-N-(2,2,2-trifluoroethyl)piperidyl-3-formamide (7.00 mg, yield was 25.38%). $^1$H NMR (400 MHz, MeOD-$d_4$) δ=8.11 (br. s., 1H), 6.51-7.23 (m, 2H), 3.96 (br. s, 2H), 2.53-3.26 (m, 5H), 1.38-2.05 (m, 4H), 6.74 (s, 1H), 4.64-4.72 (m, 1H), 4.44-4.59 (m, 2H), 3.77-3.84 (m, 1H), 3.66 (dd, J=5.02, 13.30 Hz, 1H), 3.18-3.28 (m, 3H), 1.25 (t, J=7.40 Hz, 3H). The value of $C_{14}H_{17}F_3N_6O[M+H]^+$ 343 was calculated using MS ESI, and was 343.

Embodiment 2

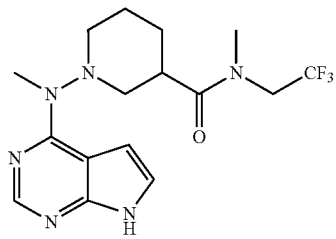

WX02

N-methyl-1-(methyl(7H-pyrrolo[2,3-d]pyrimidin-4-yl)amino)-(2,2,2-trifluoroethyl)piperidyl-3-formamide

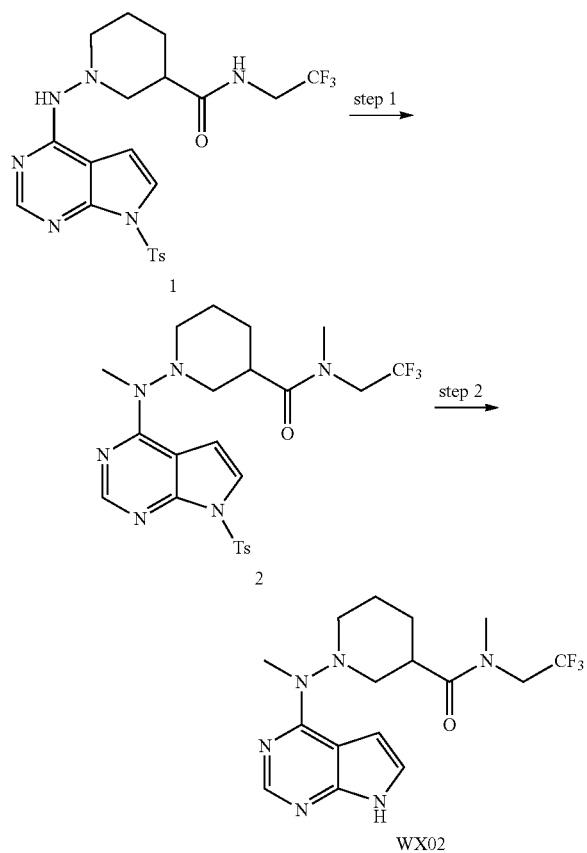

Step 1: 1-((7-tosyl-7H-pyrrolo[2,3-d]pyrimidin-4-yl)amino)-N-(2,2,2-trifluoroethyl)piperidyl-3-formamide (60.00 mg, 120.84 umol) was dissolved in THF(5 mL), and NaH (60%, 5.30 mg, 132.50 umol) was added in batches at 0° C.; after the mixture was stirred for 1 h at 0° C., methyl iodide (1.05 g, 7.40 mmol) was dropwise added. The reaction solution was warmed up to 20° C. and stirred for 2 h. TLC showed that the reaction was completed. The mixture was cooled to 0° C., added with water (10 mL), and stirred for 20 min, then the aqueous phase was extracted using ethyl acetate (10 mL×2). Merged organic phases were washed by saturated saline solution (10 mL×2), dried by anhydrous sodium sulfate, filtered and concentrated to be dry under reduced pressure to obtain N-methyl-1-[methyl-[7-(tosyl)-7H-pyrrolo[2,3-d]pyrimidin-4-yl]amino]-N-(2,2,2-trifluoroethyl)piperidyl-3-formamide which was yellow oily matter (50.00 mg, crude product). The value of $C_{23}H_{27}F_3N_6O_3S[M+H]^+$ 525 was calculated using MS ESI, and was 525.

Step 2: N-methyl-1-[methyl-[7-(tosyl)-7H-pyrrolo[2,3-d]pyrimidin-4-yl]amino]-N-(2,2,2-trifluoroethyl)piperidyl-3-formamide (50.00 mg, 95.32 umol) was dissolved in a mixed solvent of methanol (3 mL) and water (3 mL), potassium carbonate (39.52 mg, 285.96 umol) was added, and then the mixture was heated to 80° C. and stirred for 5 h. LCMS showed that the reaction was completed. The mixture was cooled to 25° C., and concentrated to be dry under reduced pressure. Residues were purified through prep-HPLC to obtain WX02: N-methyl-1-(methyl(7H-pyrrolo[2,3-d]pyrimidin-4-yl)amino)-(2,2,2-trifluoroethyl)piperidyl-3-formamide (11.00 mg, yield was 31.16%). $^1$HNMR (400 MHz, MeOD-d$_4$) δ=8.11 (br. s., 1H), 7.04-7.11 (m, 2H), 3.94-4.39 (m, 2H), 3.22 (s, 6H), 2.84-3.13 (m, 5H), 1.93 (br. s., 3H), 1.38-1.58 (m, 1H). The value of $C_{16}H_{21}F_3N_6O[M+H]^+$ 371 was calculated using MS ESI, and was 371.

Embodiment 3

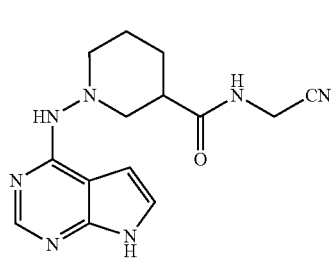

WX03

1-((7H-pyrrolo[2,3-d]pyrimidin-4-yl)amino)-N-(cyanomethyl)piperidyl-3-formamide

Intermediate 1 →$^{step\ 1}$

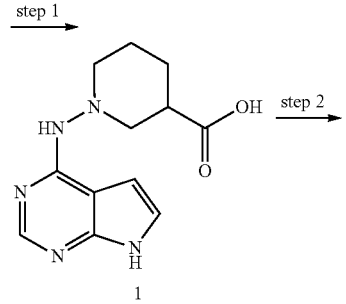

→$^{step\ 2}$

1

32

1-(methyl(7H-pyrrolo[2,3-d]pyrimidin-4-yl)amino)-
N-(2,2-trifluoroethyl)piperidyl-3-formamide

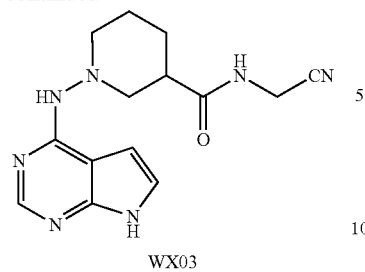

WX03

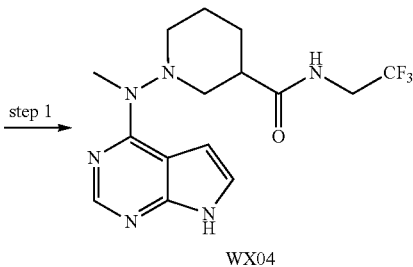

Step 1: The intermediate 1 (1.32 g, 2.98 mmol) was dissolved in a mixed solvent of tetrahydrofuran (10 mL) and water (10 mL), and sodium hydroxide (238.40 mg, 5.96 mmol) was added. The reaction solution was heated to 70° C. and stirred for 10 h. LCMS showed that the reaction was completed. The mixture was cooled to 20° C., and the solvent was concentrated to be dry under reduced pressure. Residues were neutralized by 2 M HCl till the pH value is 2-3, and then were concentrated under reduced pressure to obtain 1-(7H-pyrrolo[2,3-d]pyrimidin-4-yl-amino)piperidyl-3-carboxylic acid which was grey oily matter (2.00 g, crude product). The product was directly used in next step without needing further purification. The value of $C_{12}H_{15}N_5O_2[M+H]^+$ 262 was calculated using MS ESI, and was 262.

Step 2: 1-(7H-pyrrolo[2,3-d]pyrimidin-4-yl-amino)piperidyl-3-carboxylic acid (520.00 mg, 1.99 mmol) was dissolved in DMF (15 mL), and HOBt (537.78 mg, 3.98 mmol), EDCI (762.97 mg, 3.98 mmol), 2-glycinonitrile hydrochloride (220.98 mg, 2.39 mmol) and triethylamine (1.01 g, 9.95 mmol) were added at 0° C. The reaction solution was stirred for 10 h at 25° C. LCMS showed that the reaction was completed. Residues were poured into water (20 mL) and stirred for 20 min. The aqueous phase was extracted by dichloromethane and methanol (10: 1, 15 mL×3). Merged organic phases were washed by saturated saline solution (20 mL×2), dried by anhydrous sodium sulfate, filtered and concentrated in vacuum. Residues were purified through a prep-HPLC (NH₃.H₂O) to obtain WX03: N-(cyanomethyl)-1-(7H-pyrrolo[2,3-d]pyrimidin-4-yl-amino)piperidyl-3-formamide (56.27 mg, yield was 9.45%). ¹H NMR (400 MHz, MeOD-d₄) δ=8.21 (br. s., 1H), 7.16 (br. s., 1H), 6.72 (br. s., 1H), 4.15-4.28 (m, 2H), 2.66-3.26 (m, 5H), 1.84 (d, J=6.8 Hz, 4H). The value of $C_{14}H_{17}N_7O[M+H]^+$ 300 was calculated using MS ESI, and was 300.

Step 1: The intermediate 3 (650.00 mg, 2.36 mmol) was dissolved in DMF (15 mL), and HOBt (637.77 mg, 4.72 mmol), EDCI (904.82 mg, 4.72 mmol), 2,2,2-trifluoroethylamine (467.52 mg, 4.72 mmol) and triethylamine (1.43 mg, 14.16 mmol) were added, the reaction solution was stirred for 10 h at 25° C. LCMS showed that the reaction was completed. The mixture was poured into water (50 mL), and the aqueous phase was extracted using ethyl acetate (20 mL×3). Merged organic phases were washed by saturated saline solution (15 mL), dried by anhydrous sodium sulfate, filtered and concentrated to be dry under reduced pressure. Residues were purified through a prep-HPLC (NH₃.H₂O) to obtain WX04: 1-[methyl(7H)pyrrolo-[2,3-d]pyrimidin-4-yl) amino]-N-(2,2,2-trifluoroethyl)piperidyl-3-formamide (270.00 mg, yield was 32.11%). ¹H NMR (400 MHz, MeOD-d₄) δ=8.11 (s, 1H), 7.00-7.10 (m, 2H), 3.75-4.00 (m, 2H), 3.21 (s, 3H), 3.01 (d, J=7.3 Hz, 2H), 2.85-2.96 (m, 3H), 1.85-2.02 (m, 3H), 1.37-1.58 (m, 1H). The value of $C_{15}H_{19}F_3N_6O[M+H]^+$ 357 was calculated using MS ESI, and was 357.

Embodiment 5

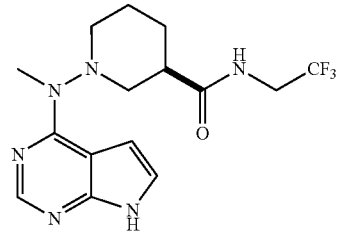

WX05

Embodiment 4

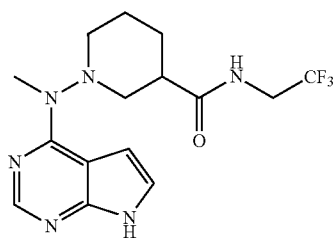

WX04

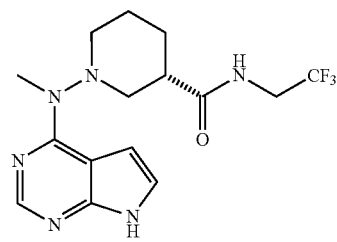

WX06

(R&S)1-(methyl(7H-pyrrolo[2,3-d]pyrimidin-4-yl)amino)-N-(2,2-trifluoroethyl)piperidyl-3-formamide

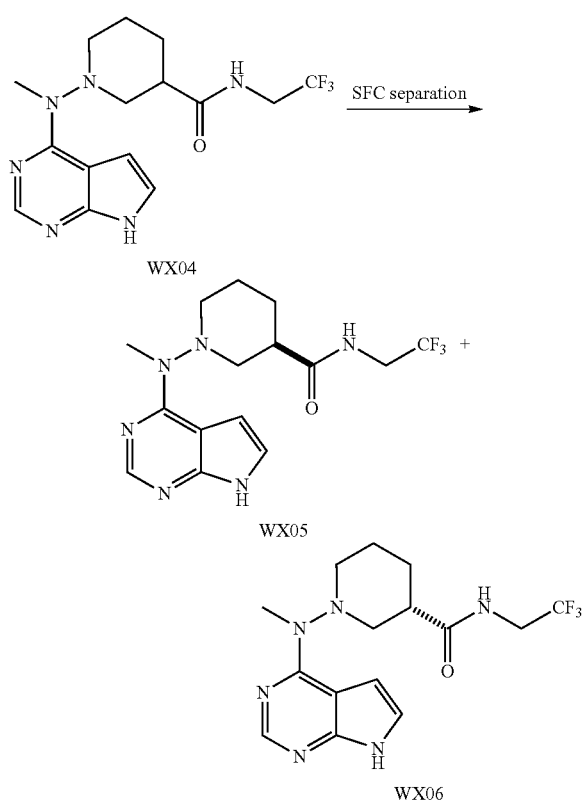

1-[methyl(7H-pyrrolo[2,3-d]pyrimidin-4-yl)amino]-N-(2,2,2-trifluoroethyl)piperidyl-3-formamide (140.00 mg, 392.87 umol) was separated through a chiral column to obtain WX05: (R or S)-1-[methyl(7H pyrrolo[2,3-d]pyrimidin-4-yl)amino]-N-(2,2,2-trifluoroethyl)piperidyl-3-formamide (68.00 mg, yield was 48.57% and WX06: (S or R)—1-[methyl(7H-pyrrolo[2,3-d]pyrimidin-4-yl)amino]-N-(2,2,2-trifluoroethyl)piperidyl-3-formamide (53.00 mg, yield was 37.86%).

SFC separation conditions:
column: AS-H chiral column
mobile phase: A: supercritical $CO_2$, B: 20% EtOH (0.1% $NH_3.H_2O$), A:B=50:50 flow rate: 60 mL/min
column temperature: 38° C.
wavelength: 220 nm
jet pressure: 100 Bar
nozzle temperature: 60° C.
evaporating temperature: 20° C.
conditioning temperature: 25° C.

WX05: (R or S)-1-[methyl(7H pyrrolo[2,3-d]pyrimidin-4-yl)amino]-N-(2,2,2-trifluoroethyl)piperidyl-3-formamide, retention time: 3.268 min. $^1$H NMR (400 MHz, MeOD-$d_4$) 8.11 (s, 1H), 7.06 (s, 2H), 3.76-3.98 (m, 2H), 3.21 (s, 3H), 2.83-3.07 (m, 5H), 1.84-2.02 (m, 3H), 1.39-1.55 (m, 1H). The value of $C_{15}H_{19}F_3N_6O[M+H]^+$ 357 calculated using MS ESI, was 357.

WX06: (S or R)-1-[methyl(7H pyrrolo[2,3-d]pyrimidin-4-yl)amino]-N-(2,2,2-trifluoroethyl)piperidyl-3-formamide, retention time: 3.991 min. $^1$H NMR (400 MHz, MeOD-$d_4$) δ=8.11 (s, 1H), 7.06 (br. s., 2H), 3.75-3.99 (m, 2H), 3.21 (s, 3H), 2.82-3.07 (m, 5H), 1.82-2.04 (m, 3H), 1.47 (d, J=12.0 Hz, 1H). The value of $C_{15}H_{19}F_3N_6O[M+H]^+$ 357 was calculated using MS ESI, and was 357.

Embodiment 6

(N-(cyanomethyl)-1-(methyl(7H-pyrrolo[2,3-d]pyrimidin-4-yl)amino)piperidyl-3-formamide Step 1: The intermediate 3 (550.00 mg, 2.00 mmol) was dissolved in DMF (15 mL), and HOBt (540.48 mg, 4.00 mmol), EDCI (766.80 mg, 4.0 mmol), 2-glycinonitrile hydrochloride (370.12 mg, 4.0 mmol) and triethylamine (1.21 mg, 12.0 mmol) were added. The mixture was stirred to react for 10 h at 25° C. LCMS showed that the reaction was completed. The mixture was poured into water (50 mL), an aqueous phase was extracted using ethyl acetate (15 mL×4), merged organic phases were washed by saturated saline solution (20 mL×2), dried by anhydrous sodium sulfate, and filtered and concentrated to be dry under reduced pressure. Residues were purified through a preparation type HPLC ($NH_3.H_2O$) to obtain WX07: N-(cyanomethyl)-1-[methyl(7H-pyrrolo[2,3-d]pyrimidin-4-yl)amino]piperidyl-3-formamide (170.00 mg, yield was 26.74%). $^1$H NMR (400 MHz, $CDCl_3$) δ=8.43 (br. s., 1H), 8.31 (br. s., 1H), 7.18 (br. s., 1H), 6.87-7.07 (m, 1H), 6.59 (br. s., 1H), 4.11-4.40 (m, 3H), 3.32-3.47 (m, 1H), 3.39 (br. s., 3H), 3.22 (br. s., 1H), 2.74-3.14 (m, 7H), 1.95 (d, J=15.9 Hz, 2H), 1.74 (d, J=12.5 Hz, 1H), 1.55 (d, J=12.7 Hz, 1H). The value of $C_{15}H_{19}N_7O[M+H]^+$ 314 was calculated using MS ESI, and was 314.

Embodiment 7

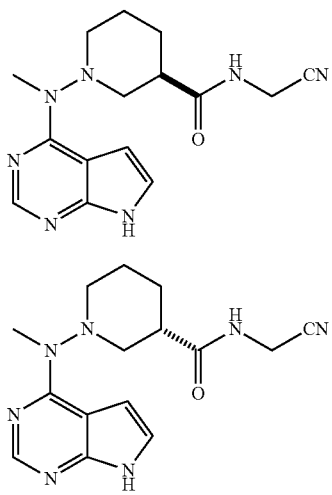

R&S (N-(cyanomethyl)-1-(methyl(7H-pyrrolo[2,3-d]pyrimidin-4-yl)amino)piperidyl-3-formamide

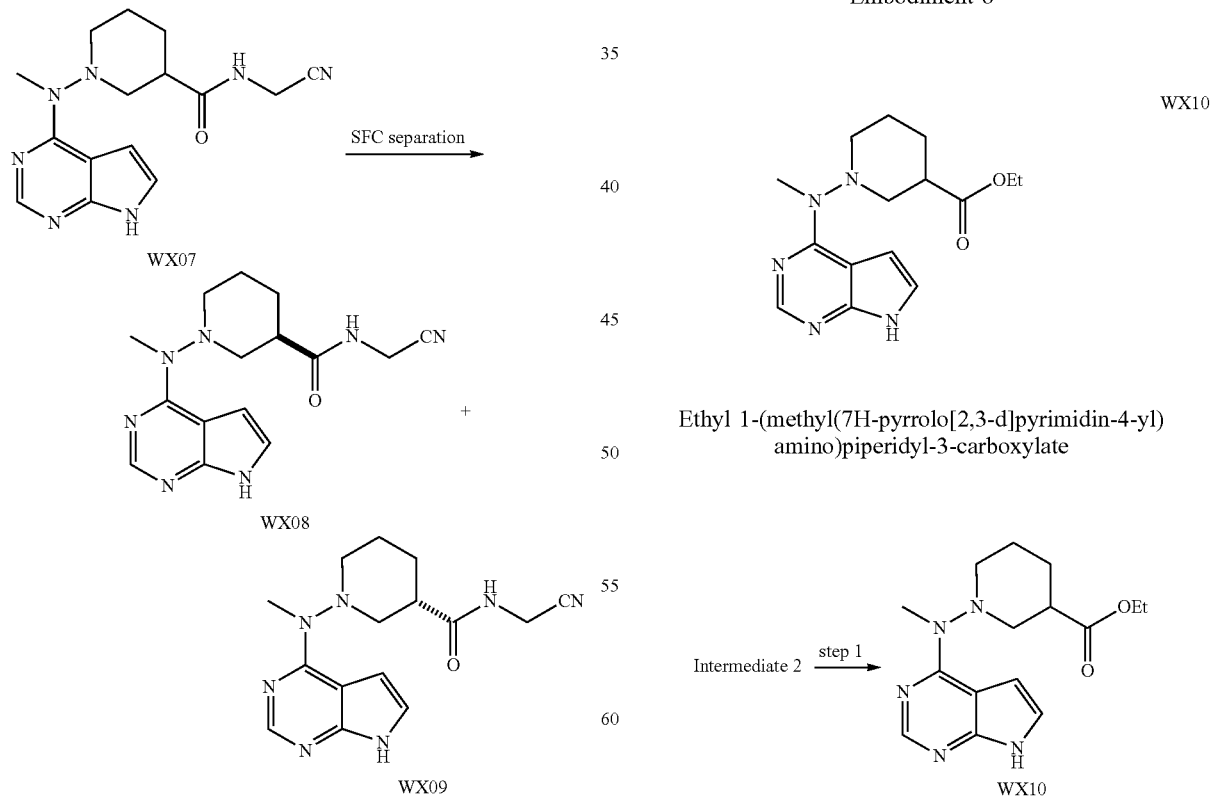

N-(cyanomethyl)-1-[methyl(7H-pyrrolo[2,3-d]pyrimidin-4-yl)amino]piperidyl)-3-formamide (170.00 mg, 542.51 umol) was separated through a chiral separation column to obtain WX08: (R or S)—N-(cyanomethyl)-1-[methyl(7H-pyrrolo[2,3-d]pyrimidin-4-yl)amino]piperidyl)-3-formamide (68.00 mg, yield was 40.00%) and WX09: (S or R)—N-(cyanomethyl)-1-[methyl(7Hpyrrolo[2,3-d]pyrimidin-4-yl)amino]piperidyl)-3-formamide (64.00 mg, yield was 37.65%).

SFC separation conditions:
separation column: AS-H
mobile phase: A: supercritical $CO_2$, B: 30% MeOH (0.1% NH3H2O), A:B=50:50
flow rate: 50 mL/min
column temperature: 38° C.
wavelength: 220 nm
jet pressure: 100 Bar
nozzle temperature: 60° C.
evaporating temperature: 20° C.
conditioning temperature: 25° C.

WX08: (R or S)—N-(cyanomethyl-1-[methyl(7H-pyrrolo[2,3-d]pyrimidin-4-yl)amino]piperidyl)-3-formamide, retention time: 5.659 min. $^1H$ NMR (400 MHz, MeOD-$d_4$) δ=8.11 (s, 1H), 6.97-7.13 (m, 2H), 4.12 (d, J=5.0 Hz, 2H), 3.21 (s, 3H), 2.79-3.07 (m, 5H), 1.80-2.03 (m, 3H), 1.38-1.55 (m, 1H). The value of $C_{15}H_{19}N_7O[M+H]^+$ 314 was calculated using MS ESI, and was 314.

WX09: (S or R)—N-(cyanomethyl-1-[methyl(7H-pyrrolo[2,3-d]pyrimidin-4-yl)amino]piperidyl)-3-formamide, retention time: 6.872 min. $^1H$ NMR (400 MHz, MeOD-$d_4$) δ=8.11 (s, 1H), 6.96-7.12 (m, 2H), 4.03-4.20 (m, 2H), 3.21 (s, 3H), 2.76-3.09 (m, 5H), 1.84-2.01 (m, 3H), 1.39-1.56 (m, 1H). The value of $C_{15}H_{19}N_7O[M+H]^+$ 314 was calculated using MS ESI, and was 314.

Embodiment 8

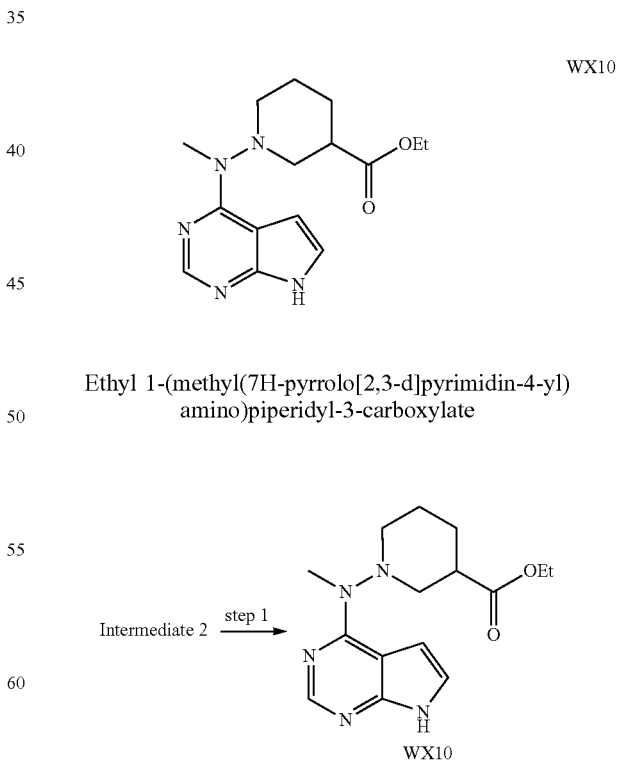

Ethyl 1-(methyl(7H-pyrrolo[2,3-d]pyrimidin-4-yl)amino)piperidyl-3-carboxylate

Step 1: Potassium carbonate (90.62 mg, 655.68 umol) was added into ethanol solution (10.00 mL) of the intermediate 2 (100.00 mg, 218.56 umol) at 25° C. under nitrogen protection. The mixture was stirred for 16 h at 25° C. TLC showed that the reaction was completed. The mixture was concentrated under reduced pressure at 40° C. Residues were diluted by water (10 mL). The aqueous phase was extracted using ethyl acetate (50 mL×2). Merged organic phases were washed by saturated saline water (20 mL×2), dried by anhydrous sodium sulfate, and filtered, and the solvent was concentrated under reduced pressure. Residues were purified using a preparation type HPLC (alkalic method) to obtain WX10: Ethyl 1-[methyl(7H-pyrrolo[2,3-d]pyrimidin-4-yl)amino]piperidyl-3-carboxylate (30.00 mg, 98.89 umol, yield was 45.25%, and the purity was 100%). $^1$H NMR (400 MHz, Methanol-$d_4$) δ=8.13 (s, 1H), 7.06 (d, J=16.8 Hz, 2H), 4.14 (q, J=6.9 Hz, 2H), 3.23 (s, 3H), 3.15 (d, J=6.8 Hz, 1H), 2.94 (br. s., 4H), 2.12 (d, J=13.3 Hz, 1H), 1.92 (br. s., 2H), 1.41 (br. s., 1H), 1.26 (t, J=6.9 Hz, 3H), 1.00 (br. s., 1H). The value of $C_{15}H_{21}N_5O_2[M+H]^+$ 304 was calculated using MS ESI, and was 304.

Embodiment 9

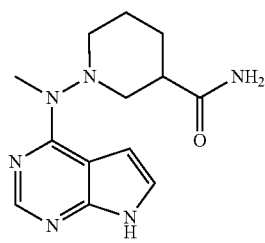

WX11

1-[methyl(7H-pyrrolo[2,3-d]pyrimidin-4-ylamino] piperidyl)-3-formamide

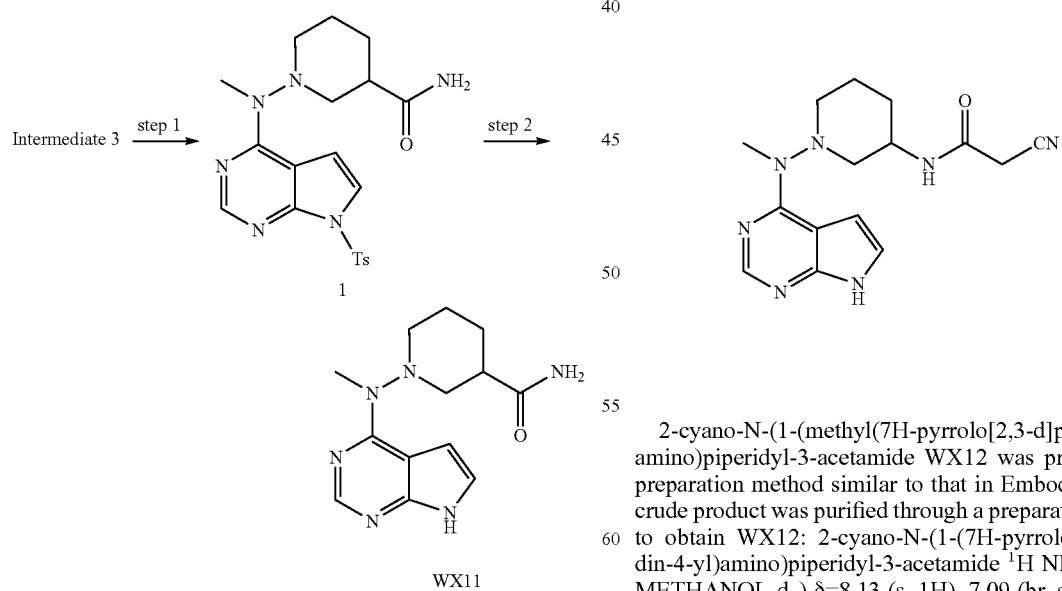

Step 1: Ethyl 1-[methyl-[7-(tosyl)pyrrolo[2,3-d]pyrimidin-4-yl]amino]piperidyl-3-carboxylate (470.00 mg, 1.09 mmol) and triethylamine (166.10 mg, 1.64 mmol) were dissolved in tetrahydrofuran (20.00 mL). Isopropyl chloroformate (134.11 mg, 1.09 mmol, 1.00 eq) was dropped into the foregoing solution system at 0° C. The mixture was stirred for 1 h at room temperature. TLC (petroleum ether: ethyl acetate=1:1) showed that the reaction was completed. The mixture was directly used in next reaction. The mixture above was cooled to 0° C. again and added with aqueous ammonia (383.56 mg, 10.94 mmol). The mixture obtained finally was stirred for 16 h at 25° C. The mixture was diluted by water (10 mL). The aqueous phase was extracted using ethyl acetate (50 mL×3). Merged organic phases were washed by saturated saline water (20 mL×2), dried by anhydrous sodium sulfate, and filtered and concentrated to be dry under reduced pressure to obtain 1-[methyl-[7-(tosyl)pyrrolo[2,3-d]pyrimidin-4-yl]amino]piperidyl)-3-formamide (470.00 mg, crude product) which was yellow solid, and was directly used in next reaction without further purification.

Step 2: 1-[methyl-[7-(tosyl)pyrrolo[2,3-d]pyrimidin-4-yl]amino]piperidyl)-3-formamide (70.00 mg, 163.36 umol) was dissolved in a mixed solvent of tetrahydrofuran (5.00 mL) and methanol (5.00 mL), and a water solution (2.50 mL) of sodium hydroxide (13.07 mg, 326.72 umol) was added. The mixture was stirred to react for 2 h at 100° C. TLC showed that the reaction was completed. The mixture was cooled to 25° C., and the solvent was concentrated under reduced pressure at 40° C. Residues were adjusted by diluted hydrochloric acid to pH=8-9. The residues were purified using a preparation type HPLC (alkalic method) to obtain WX11: 1-[methyl(7H-pyrrolo[2,3-d]pyrimidin-4-yl)amino]piperidyl)-3-formamide (30.00 mg, yield was 66.94%). $^1$H NMR (400 MHz, METHANOL-$d_4$) δ=8.12 (s, 1H), 7.07 (s, 2H), 3.23 (s, 3H), 3.10-2.81 (m, 5H), 2.03-1.87 (m, 3H), 1.54-1.41 (m, 1H). The value of $C_{13}H_{18}N_6O[M+H]^+$ 275 was calculated using MS ESI, and was 275.

Embodiment 10

WX12

2-cyano-N-(1-(methyl(7H-pyrrolo[2,3-d]pyrimidin-4-yl)amino)piperidyl-3-acetamide WX12 was prepared using a preparation method similar to that in Embodiment 6, and a crude product was purified through a preparation type HPLC to obtain WX12: 2-cyano-N-(1-(7H-pyrrolo[2,3-d]pyrimidin-4-yl)amino)piperidyl-3-acetamide $^1$H NMR (400 MHz, METHANOL-$d_4$) δ=8.13 (s, 1H), 7.09 (br. s., 1H), 7.05 (d, J=3.5 Hz, 1H), 4.24-4.08 (m, 1H), 3.22 (s, 3H), 3.15 (d, J=5.5 Hz, 1H), 3.06-2.83 (m, 2H), 2.68 (t, J=10.0 Hz, 1H), 2.05 (d, J=11.5 Hz, 1H), 1.99-1.85 (m, 2H), 1.32-1.18 (m, 1H). The value of $C_{15}H_{19}N_7O[M+H]^+$ 314 was calculated using MS ESI, and was 314.

Embodiment 11

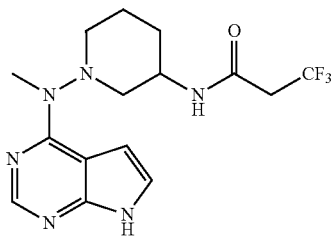

3,3,3-trifluoroethyl-N-(1-(methyl(7H-pyrrolo[2,3-d]pyrimidin-4-yl)amino)piperidyl-3-)propylcarboxamide WX13 was prepared using a preparation method similar to that in Embodiment 6, and a crude product was purified through a preparation type HPLC to obtain WX13: 3,3,3-trifluoroethyl-N-(1-(methyl(7H-pyrrolo[2,3-d]pyrimidin-4-yl)amino)piperidyl-3-)propylcarboxamide. $^1$H MR (400 MHz, METHANOL-d$_4$) δ=8.13 (s, 1H), 7.12-7.04 (m, 2H), 4.21 (t, J=11.2 Hz, 1H), 3.22 (s, 3H), 3.15 (d, J=10.5 Hz, 1H), 2.97-2.83 (m, 2H), 2.67 (t, J=9.9 Hz, 1H), 2.04 (d, J=11.8 Hz, 1H), 1.98-1.84 (m, 2H), 1.32-1.19 (m, 1H). The value of $C_{15}H_{19}F_3N_6O[M+H]^+$ 357 was calculated using MS ESI, and was 357.

Embodiment 12

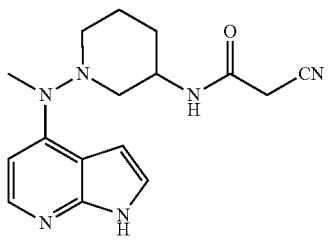

N-(cyanomethyl)-1-(methyl(1H-pyrrole[2,3-b]pyridyl-4-)amino)piperidyl-3-formamide

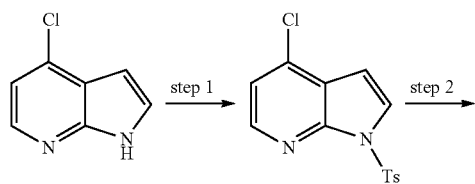

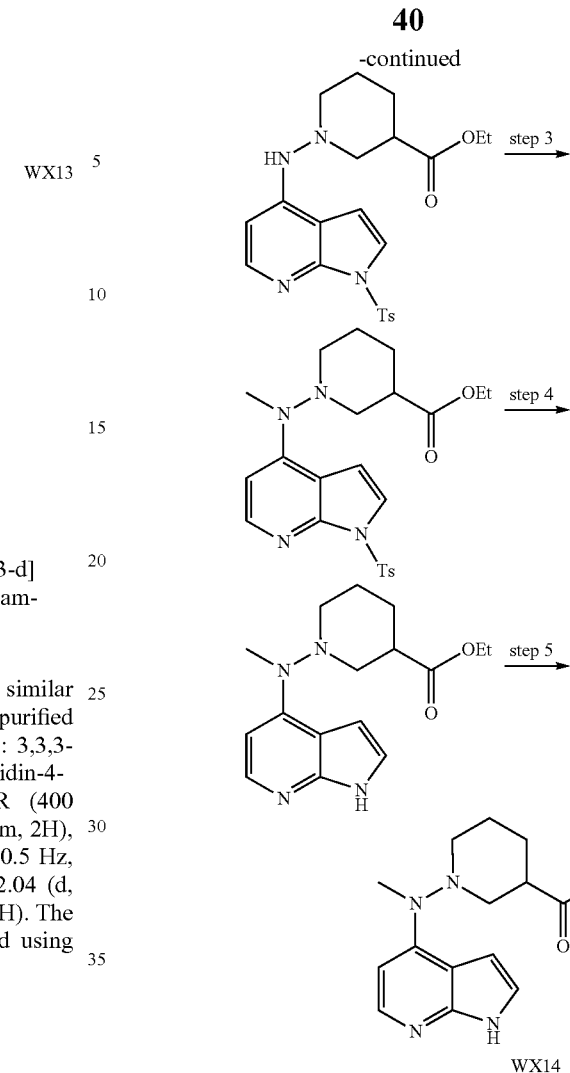

Step 1: 4-chloro-1H-pyrrole[2,3-b]pyridine (20.00 g, 131.08 mmol) was dissolved in dichloromethane (400 mL), and Et$_3$N (39.79 g, 393.24 mmol) was added; later, DMAP (1.60 g, 13.11 mmol) was added and cooled to 0° C., p-toluenesulfonyl chloride (27.49 g, 144.19 mmol) was added in batches, and continuously stirred for 4 h at this temperature, then warmed up to 25° C. and stirred for 12 h. LC-MS showed that the raw materials were completely reacted and a target product was detected. Water (100 mL) was added for quenching, the aqueous phase was extracted by dichloromethane (100 mL×3), organic layers were merged, and washed by saturated saline solution (100 mL), dried by anhydrous Na$_2$SO$_4$, filtered, and concentrated under reduced pressure to obtain brown solid, and the crude product was recrystallized (ethyl acetate:petroleum ether=10 mL: 200 mL) to obtain a crude product of 4-chloro-1-(tosyl)pyrrole[2,3-b]pyridine (18.90 g). The product was directly used in next reaction without further purification. The value of $C_{14}H_{11}ClN_2O_2S[M+H]^+$ 307.0 was calculated using MS ESI, and was 306.9.

Step 2: 4-chloro-1-(tosyl)pyrrole[2,3-b]pyridyl (5.9 g, 19.2 mmol), and 1-aminopiperidyl-3-ethyl formate (3.00 g, 17.42) (referring to key intermediate route) were dissolved in anhydrous toluene (40 mL), and Cs$_2$CO$_3$ (11.35 g, 34.84 mmol) was added, replaced three times by N$_2$, then Pd2(dba)$_3$ (1.60 g, 1.74 mmol) and Xantphos (2.02 g, 3.48 rnmol) were added, replaced three times by N₂. The mixture was subjected to a reflux reaction for 3 h at 120° C., and LC-MS showed that a product was generated. The reaction time was extended, the raw materials were not consumed anymore, and by-products with big molecular weight were generated at the same time. The mixture was diluted by ethyl acetate, filtered and the filtrate was concentrated, separated by a column (petroleum ether:ethyl acetate=5:1) to obtain light red 1-[[1-(tolylsulfonyl)pyrrole[2,3-b]pyridine-4-]amino]piperidyl-3-ethyl formate (800.00 mg, yield was 10.38%). The value of $C_{22}H_{26}N_4O_4S[M+H]^+$ 443.1 was calculated using MS ESI, and was 443.1.

Step 3: 1-[[1-(tolylsulfonyl)pyrrole[2,3-b]pyridyl-4-]amino]piperidyl-3-ethyl formate (543.00 mg, 1.23 mmol) was dissolved in tetrahydrofuran (10 mL), and NaH (54.00 mg, 1.35 mmol) was added in batches at 0° C., and stirred for 0.5 h at 25° C. Then the mixture was cooled to 0° C. again, added with CH₃I (174.17 mg, 1.23 mmol, 1.00 Eq), and then stirred to react for 1 h at 25° C. LC-MS showed that the raw materials were not reacted anymore, then added with water (10 ml) to quench, and extracted by ethyl acetate (10 mL×3). Organic layers were merged, washed by saturated saline solution (10 mL×2), dried by anhydrous Na₂SO₄, then filtered, concentrated and separated by a silicagel column (100-200 mesh silica gel, petroleum ether:ethyl acetate=5:1 to 3:1) to obtain yellow oily 1-[methyl-[1-(tosyl) pyrrole[2,3-b] pyridin-4yl-]amino]piperidyl-3-ethyl formate (204.00 mg, yield was 35.60%). The value of $C_{23}H_{28}N_4O_4S[M+H]^+$ 457.1 was calculated using MS ESI, and was 457.1.

Step 4: 1-[methyl-[1-(tosyl)pyrrole[2,3-b]pyridyl-4-]amino]piperidyl-3-ethyl formate (204.00 mg, 446.82 umol) was dissolved in a mixed solvent of H₂O (4 mL) and CH₃OH (4 mL), and NaOH (71.5 mg, 1797.28 umol) was added and stirred to react for 13 h at 80° C. LC-MS showed that the raw materials were completely reacted, then the solvent was removed by reduced pressure distillation, and HCl (2 M) was added to adjust the pH to be neutral, and then a buff crude product (122 mg) of 1-[methyl-[1-(tosyl)pyrrole[2,3-b]pyridyl-4-]amino]piperidyl-3-formate was obtained after concentration under reduced pressure. The product was directly used in next reaction without further purification. The value of $C_{14}H_{18}N_4O_2[M+H]^+$ 274.9 was calculated using MS ESI, and was 274.9.

Step 5: 1-[methyl-[1-(tosyl)pyrrole[2,3-b]pyridyl-4-]amino]piperidyl-3-formate (61.00 mg, 222.37 umol) was dissolved in DMF (4 mL), and HOBt (72.12 mg, 533.68 umol) and EDCI (102.2 mg, 533.68 umol) were added and stirred to react for 30 min at 25° C., then 2-glycinonitrile hydrochloride (24.69 mg, 266.84) and Et₃N (90.01 mg, 889.47 umol) were added, and continuously stirred to react for 18 h at 25° C. LC-MS showed that the raw materials were completely reacted, and the target molecular weight was detected. Preparation type HPLC (alkalic method) separation was conducted to obtain WX14: N-(cyanomethyl)-1-(methyl(1H-pyrrole[2,3-b]pyridyl-4-)amino)piperidyl-3-formamide (19.2 mg, yield was 27.6%). ¹H NMR (400 MHz, DMSO-d₆) δ=11.27 (br. s., 1H), 8.66 (t, J=5.3 Hz, 1H), 7.85 (d, J=5.8 Hz, 1H), 7.10 (br. s., 1H), 6.87 (br. s., 1H), 6.23 (d, J=5.3 Hz, 1H), 4.08 (d, J=5.5 Hz, 2H), 3.00 (s, 3H), 2.91-2.62 (m, 6H), 1.79 (br. s., 2H), 1.38 (m, 1H). The value of $C_{16}H_{20}N_6O[M+H]^+$ 313 was calculated using MS ESI, and was 313.

Embodiment 13

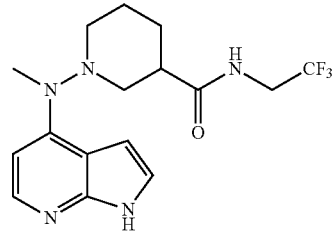 [SMILES: CN(c1ccnc2[nH]ccc12)N1CCCC(C(=O)NCC(F)(F)F)C1]

N-(2,2,2-trifluoroethyl)-1-(methyl(1H-pyrrole[2,3-d]pyridin-4-yl)amino)piperidyl-3-formamide WX15 was prepared using a preparation method similar to that in Embodiment 12, and a crude product was purified through a preparation type HPLC to obtain WX15: N-(2,2,2-trifluoroethyl)-1-(methyl(I H-pyrrole[2,3-d]pyridin-4-yl)amino)piperidyl-3-formamide. ¹H NMR (400 MHz, DMSO-d₆) δ=11.27 (br. s., 1H), 8.66 (t, J=5.3 Hz, 1H), 7.85 (d, J=5.8 Hz, 1H), 7.10 (br. s., 1H), 6.87 (br. s., 1H), 6.23 (d, J=5.3 Hz, 1H), 4.08 (d, J=5.5 Hz, 2H), 3.00 (s, 3H), 2.91-2.62 (m, 6H), 1.79 (br. s., 2H), 1.38 (m, 1H). The value of $C_{16}H_{20}N_6O[M+H]^+$ 313 was calculated using MS ESI, and was 313.

Embodiment 14

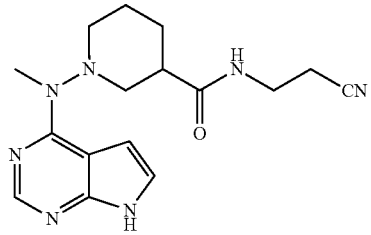

WX16

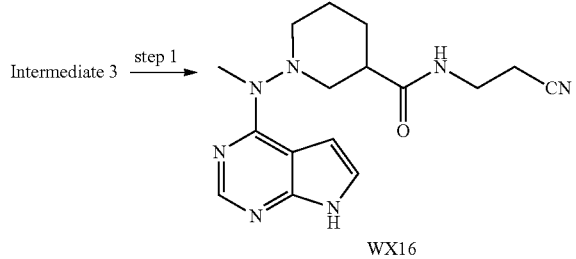

WX16

N-(cyanoethyl)-1-(methyl(1H-pyrrole[2,3-d]pyridyl-4-)amino)piperidyl-3-formamide WX16 was prepared using a preparation method similar to that in Embodiment 12, and a crude product was purified through a preparation type HPLC to obtain WX16: N-(cyanoethyl)-1-(methyl(I H-pyrrole[2,3-d]pyridyl-4-)amino)piperidyl-3-formamide (32.30 mg, yield was 35.0%). ¹H NMR (400 MHz, DMSO-d₄) δ=8.12 (s, 1H), 7.12-7.02 (m, 2H), 3.42 (t, J=6.4 Hz, 2H), 3.22 (s, 3H), 3.08-2.99 (m, 2H), 2.98-2.79 (m, 3H), 2.70-2.62 (m, 2H), 2.30-2.22 (m, 1H), 2.03-1.86 (m, 3H), 1.58-1.42 (m, 1H), 1.28-1.05 (m, 1H). The value of $C_{16}H_{21}N_7O[M+H]^+$ 328.1 was calculated using MS ESI, and was 328.1.

Embodiment 15

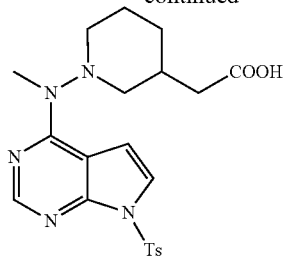

WX17

N-(2,2,2-trifluoroethyl)-2-(1-(methyl(7-tosyl-7H-pyrrole[2,3-d]pyrimidin-4-yl)amino) piperidyl-3-acetamide

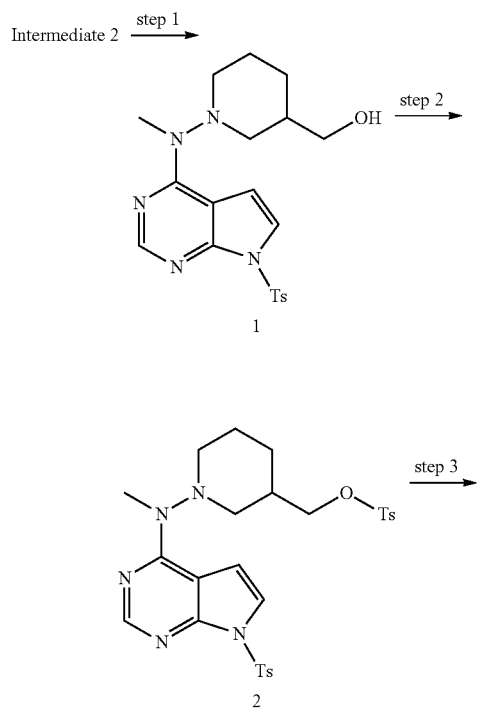

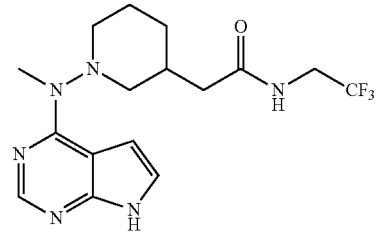

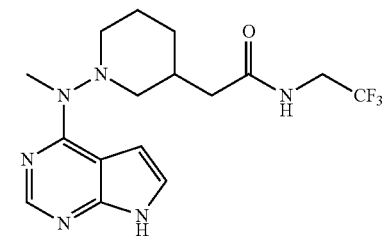

Step 1: The intermediate 2 (1.65 g, 3.61 mmol) was dissolved in $C_2H_5OH$ (40 mL), and protected by $N_2$, then NaBH$_4$ (546.27 mg, 14.44 mmol) was added at 0° C., and then stirred to react for 16 h at 25° C. LC-MS showed that the raw materials were completely reacted, and a target molecular weight was detected. Water (5 mL) was added for quenching, then the mixture was extracted by ethyl acetate (10 mL×3). Organic phases were merged, washed by saturated saline solution (10 mL), dried by anhydrous Na$_2$SO$_4$, and concentrated under reduced pressure to obtain yellow viscous liquid (1-(methyl(7-tosyl-7H-pyrrole[2,3-b]pyrimidine-4-)amino)piperidin-3-yl)methanol (1.29 g, crude product) which was not separated and directly used in next step. The value of $C_{20}H_{25}N_5O_3S[M+H]^+$ 416 was calculated using MS ESI, and was b416.

Step 2: (1-(methyl(7-tosyl-7H-pyrrole[2,3-b]pyrimidine-4-)amino)piperidyl-3-yl)methanol (967.50 mg, 2.33 mmol) and Et$_3$N (706.85 mg, 6.99 mmol) were dissolved in CH$_2$Cl$_2$ (30.00 mL), and DMAP (28.45 mg, 232.87 umol, 0.1 eq) and paratoluensulfonyl chloride (1.864 g, 9.76 mmol, 4.2 eq) were added under N$_2$ at 0° C., then the system was stirred to react for 6 h at 25° C. LC-MS showed that the reaction was complete, and water (20 mL) was added for quenching. Then the aqueous phase was extracted using AcOET (10 mL×3), and organic phases were merged, washed by HCl (2 M, 10 mL) and saturated saline solution (10 mL) successively, dried by anhydrous Na$_2$SO$_4$, filtered and concentrated. Silicagel column separation (100-200 mesh silica gel, petroleum ether:ethyl acetate=3/1, 1/1) was conducted to obtain white p-(1-(methyl(7-tosyl-7H-pyrrole[2,3-b]pyrimidin-4-)amino)piperidin-3-yl)methylbenze nesulfonate (993.00 mg, wherein the yield was 74.73%). The value of $C_{33}H_{46}N_6O_5S_2$ $[M+H]^+$ 470 was calculated using MS ESI, and was 470.

Step 3: (1-(methyl(7-tosyl-7H-pyrrole[2,3-b]pyrimidine-4-)amino)piperidin-3-yl)methyl benzenesulfonate (943.00 mg, 1.66 mmol) was dissolved in a mixed solvent of DMF (30.00 mL) and H$_2$O (10.00 mL), and KCN (440.00 mg, 6.76 mmol) was added and stirred to react for 6 h at 80° C. LC-MS showed that the raw materials were completely reacted, and a target molecular weight was detected. AcOEt (5 mL) was added to dilute and the mixture was stirred, then ethyl acetate (10 mL×3) was used for extraction. Organic layers were merged, washed by saturated saline solution (10 mL×3), dried by anhydrous Na₂SO₄, filtered and concentrated. Silicagel column separation (100-200 mesh silica gel, petroleum ether:ethyl acetate=3/1, 1/1) was conducted to obtain buff viscous material 2-(1-(methyl(7-tosyl-7H-pyrrole pyrimidine-4-)amino)piperidin-3-yl)acetonitrile (665.00 mg, wherein the yield was 94.37%). The value of $C_{21}H_{24}N_6O_2S[M+H]^+$ 425 was calculated using MS ESI, and was 425.

Step 4: HCl (12.0 ml, 72.18 mmol, 237.53 eq) was added to 2-(1-(methyl(7-tosyl-7H-pyrrole[2,3-b] pyrimidine-4-)amino)piperidin-3-yl)acetonitrile (129.00 mg, 303.87 umol), and the mixture was cooled to room temperature after being stirred to reflux for 15 h at 100° C., then NaOH (24 mg, 600 umol) was added and the mixture was continuously stirred for 4 h at 100° C. LC-MS showed that the raw materials were completely reacted, and a target molecular weight was detected. The reaction solution was concentrated and separated by a preparation type HPLC (alkalic method) to obtain 2-(1-(methyl(7-tosyl-7H-pyrrole[2,3-b]pyrimidine-4-)amino)piperidyl-3-)acetic acid (90.00 mg, yield was 97.04%). The value of $C_{14}H_{19}N_5O_2[M+H]^+$ 290 was calculated using MS ESI, and was 290.

Step 5: 2-(1-(methyl(7-tosyl-7H-pyrrole[2,3-b]pyrimidine-4-)amino)piperidin-3-yl)acetic acid (45.50 mg, 157.26 umol) was dissolved in DMF (4.00 mL), and HOBt (85.00 mg, 629.04 umol, 4.00 eq) and EDCI (212.79 mg, 1.11 mmol, 4.00eq) were added and stirred to react for 30 min at 25° C., then 2,2,2-trifluoroethylamine (46.73 mg, 471.78 umol, 3.00 eq) and Et₃N (63.65 mg, 629.04 umol, 4.00 eq) were added and continuously stirred to react for 12 h at this temperature. LC-MS showed that the raw materials were completely reacted, and a target molecular weight was detected. The mixture was filtered and separated by a preparation type HPLC (alkaline method) to obtain WX017: N-(2,2,2-trifluoromethyl)-2-(1-(methyl(7-tosyl-7H-pyrrole[2,3-b]pyrimidine-4-)amino)piperidin-3-yl)acetamide (7.40 mg, yield was 14.37%). ¹H NMR (400 MHz, METHANOL-d₄) δ=8.11 (s, 1H), 7.11-7.03 (m, 2H), 4.65 (br. s., 1H), 4.02-3.76 (m, 2H), 3.20 (s, 3H), 3.01-2.80 (m, 3H), 2.62 (t, J=10.5 Hz, 1H), 2.41 (dd, J=3.5, 7.5 Hz, 1H), 2.26-2.16 (m, 2H), 1.99-1.77 (m, 3H), 1.12-0.93 (m, 1H). The value of $C_{16}H_{21}F_3N_6O[M+H]^+$ 371 was calculated using MS ESI, and was 371.

Embodiment 16

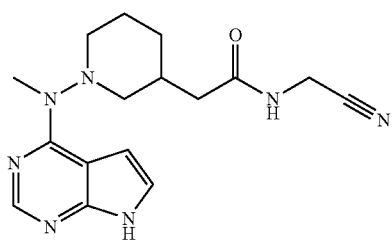

WX18

N-(cyanomethyl)-2-(1-(methyl(7-tosyl-7H-pyrrole[2,3-b]pyrimidyl-4-)amino)piperidyl-3-)acetamide WX18 was prepared using a preparation method similar to that in Embodiment 15, and a crude product was purified through a preparation type HPLC to obtain WX18 (4.20 mg, yield was 7.82%). ¹H NMR (400 MHz, METHANOL-d₄) δ=8.11 (s, 1H), 7.15-7.03 (m, 2H), 4.14 (d, J=4.0 Hz, 2H), 3.21 (s, 3H), 3.01-2.79 (m, 3H), 2.68-2.53 (m, 1H), 2.48-2.53 (m, 2H), 2.34-2.28 (m, 1H), 2.22 (d, J=6.0 Hz, 2H), 1.94-1.82 (m, 3H). The value of $C_{16}H_{21}N_7O[M+H]^+$ 328 was calculated using MS ESI, and was 328.

Embodiment 17

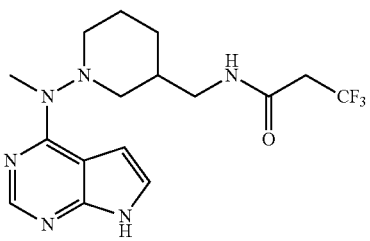

WX19

3,3,3-trifluoro-N-((1-(methyl(7H-pyrrole[2,3-d]pyrimidine-4-)amino)piperidyl-3-)methyl)propionamide

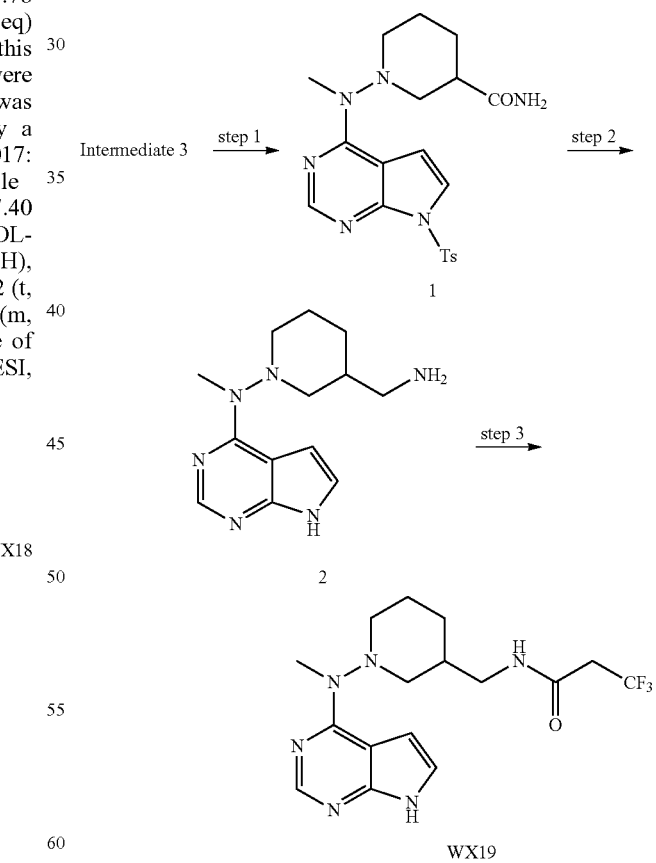

Step 1: The intermediate 3 (1.15 g, 2.67 mmol) and isopropyl chloroformate (327.57 mg, 2.67 mmol, 1.00 Eq) were dissolved in THF (30 mL), Et₃N (811.42 mg, 8.02 mmol, 3.00 Eq) was dropwise added at a temperature lower than 10° C., then the mixture was stirred to react for 1 h at 25° C., then cooled to 10° C., added with NH$_3$.H$_2$O (3.75 g, 26.76 mmol, 10.01 Eq) and then t continuously stirred to react for 7 h at 25° C. LC-MS showed that the raw materials were completely reacted, and a target molecular weight was detected. Ice water (10 mL) was added and stirred for 30 min, and then ethyl acetate (20 mL×3) was adopted for extraction; organic layers were merged, washed by saturated saline solution (10 mL), dried by anhydrous Na$_2$SO$_4$, filtered and concentrated, and separated by silicagel column chromatography (100-200 mesh silica gel, ethyl acetate) to obtain white solid 1-[[1-(tolylsulfonyl)pyrrole[2,3-b]pyridine-4-]amino]piperidyl)-3-formamide (568.00 mg, yield was 49.65%). The value of C$_{20}$H$_{24}$N$_6$O$_3$S[M+H]$^+$ 429 was calculated using MS ESI, and was 429.

Step 2: 1-[[1-(tolylsulfonyl)pyrrole[2,3-b]pyridine-4-]amino]piperidyl)-3-formamide (569.9 mg, 1.33 mmol) was suspended in THF (20 ml), added with LiAlH4 (807.58 mg, 21.28 mmol) at 0° C., then was heated and reflux for 24 h at 70° C. LC-MS showed that the reaction was completed. Water (0.8 ml), NaOH (0.8 ml 10%) solution and water (2.4 ml) were added successively at 0° C. and stirred for 15 min. The mixture was filtered, concentrated, to separated by prepare TLC (CH$_2$Cl$_2$:CH$_3$OH=10:1) to obtain white solid N-(3-aminomethyl)piperidyl-1-)-N-methyl-7H-pyrrole[2,3-b]pyrimidine-4-amine (147.00 mg, eyield was 42.45%). The value of C$_{13}$H$_{20}$N$_6$[M+H]$^+$ 261.1 was calculated using MS ESI, and was 261.1.

Step 3: 3,3,3-trifluoropropionate (57.74 mg, 450.94 umol, 2.00 eq) was dissolved in DMF (4 mL), then HOBt (121.86 mg, 901.88 umol, 4.00 eq) and EDCI (172.89 mg, 901.88 umol, 4.00 eq) were added and stirred to react for 30 min at 25° C.; then N-(3-aminomethyl)piperidyl-1-)-N-methyl-7H-pyrrole[2,3-b]pyrimidine-4-amine (58.70 mg, 225.47 umol, 1.00 eq) and Et$_3$N (182.52 mg, 1.80 mmol, 8.00 eq) were added. The mixture was continuously stirred to react for 12 h at 25° C. LC-MS showed that the reaction was completed. Then the mixture was filtered, concentrated under reduced pressure, and the filtrate was separated by a preparation type HPLC (alkalic method) to obtain WX19: 3,3,3-trifluoro-N ((1-(methyl(7H-pyrrole[2,3-d]pyrimidine-4-)amino)piperidyl-3-)methyl)propionamide (7.4 mg, yield was 8.8%). $^1$H NMR (400 MHz, METHANOL-d$_4$) δ=8.09 (s, 1H), 7.02 (s, 2H), 3.23-3.16 (m, 4H), 3.16-3.06 (m, 3H), 3.01-2.75 (m, 3H), 2.57 (t, J=10.5 Hz, 1H), 2.21-2.02 (m, 1H), 1.94-1.72 (m, 3H), 1.47-1.12 (m, 1H), 1.09-0.84 (m, 1H). The value of C$_{16}$H$_{21}$F$_3$N$_6$O[M+H]$^+$ 371 was calculated using MS ESI, and was 371.

Embodiment 18

N-(cyanomethyl)-1-(methyl(7H-pyrrolo[2,3-d]pyrimidin-4-yl)amino)piperidyl-4-formamide

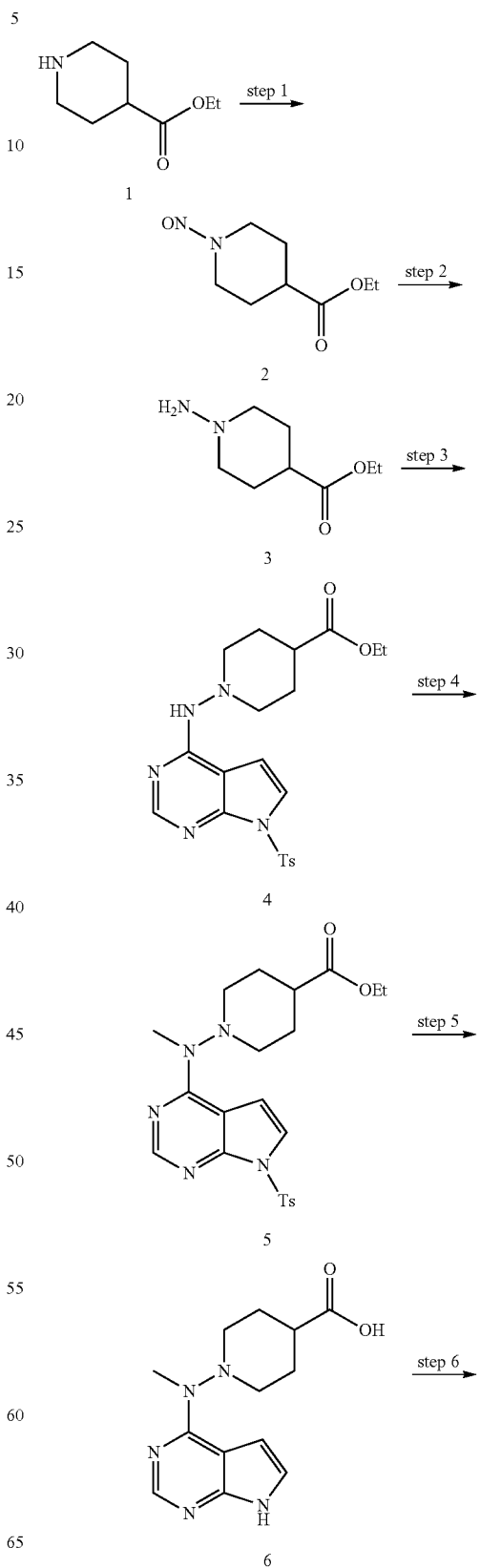

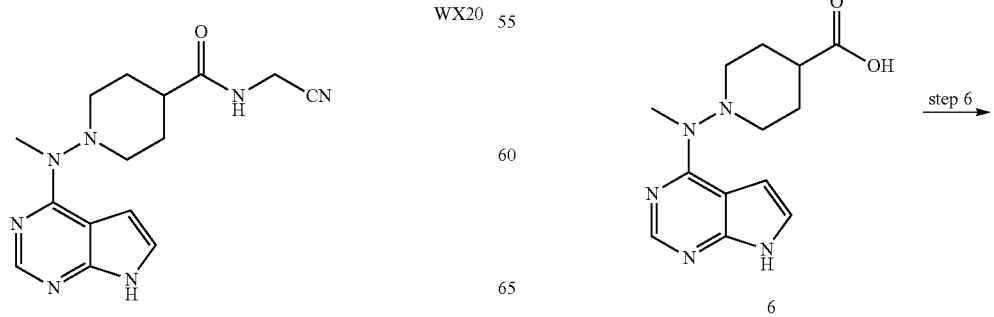

WX20

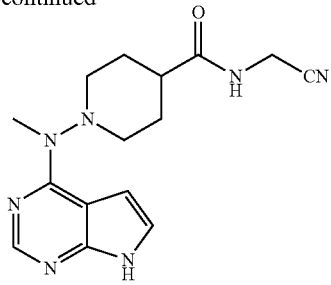

WX20

Step 1: piperidyl-4-carboxylic acid ethyl ester (9.00 g, 57.25 mmol) was dissolved in a mixture of acetic acid (30 mL) and water (30 mL), and cooled to 0° C., then an aqueous solution (30 mL) of sodium nitrite (7.90 g, 114.50 mmol) was dropwise added under nitrogen protection. After the aqueous solution was completely dropwise added, the reaction solution was stirred for 30 min at 0° C., and then stirred for 2 h at 25° C. TLC showed that the reaction was completed. The mixture was extracted using ethyl acetate (100 mL×2), merged organic phases were washed by saturated saline solution (20 mL×2), dried by anhydrous sodium sulfate, and filtered and concentrated to be dry under reduced pressure and at 70° C. so as to remove partial acetic acid. Residues were dissolved in ethyl acetate (100 mL) and water (50 mL), and adjusted by NaOH (2 M) to pH=8-9. The mixture was extracted using ethyl acetate (100 mL×2), merged organic phases were washed by saturated saline water (20 mL×2), dried by anhydrous sodium sulfate, filtered, and concentrated under reduced pressure to obtain 1-nitrosopiperidyl-4-carboxylic acid ethyl ester (10.60 g, crude product) which was yellow oily matter and directly used in next reaction without further purification. The value of $C_8H_{14}N_2O_3[M+H]^+$ 87 was calculated using MS ESI, and was 187.

Step 2: 1-nitrosopiperidyl-4-carboxylic acid ethyl ester (10.60 g, 58.04 mmol) was dissolved in methanol (80 mL) and cooled to −10° C., then zinc dust (17.68 g, 270.39 mmol) was added under nitrogen protection. Acetic acid (32.47 g, 540.79 mmol, 10.00 Eq) was dropwise added in the foregoing solution during 30 min at −10° C. The mixture was stirred for 30 min at −10° C., and then stirred for 2 h at 0° C. TLC showed that the reaction was completed. The mixture was filtered, and washed by methanol (50 mL) and water (50 mL) respectively. The filtrate was concentrated under reduced pressure at 70° C. Residues were dissolved in dichloromethane:methanol (5:1, 100 mL), and adjusted by NaOH (2 M) to pH=8-9. The mixture was filtered through diatomite, and washed by a mixed solution of dichloromethane and methanol (5:1). The filtrate was concentrated under reduced pressure to obtain 1-aminopiperidyl-4-carboxylic acid ethyl ester (9.80 g, crude product) which was buff oily matter and was directly used in next reaction without further purification. The value of $C_8H_{16}N_2O_2[M+H]^+$ 173 was calculated using MS ESI, and was 173.

Step 3: a mixture of 1-aminopiperidyl-4-carboxylic acid ethyl ester (9.80 g, 48.37 mmol, 1.00 Eq) and 4-chloro-7-(tosyl)pyrrolo[2,3-d]pyrimidine (16.37 g, 53.21 mmol, 1.10 Eq) was dissolved in dioxane (100 mL), and triethylamine (14.68 g, 145.11 mmol, 3.00 Eq) was added under nitrogen protection, then the mixture was stirred for 12 h at 110° C. TLC showed that the reaction was completed. The mixture was cooled to 25° C., and concentrated under reduced pressure at 60° C., then residues were poured into water (50 mL). The aqueous phase was extracted using ethyl acetate (100 mL×3). Merged organic phases were washed by saturated saline water (20 mL×3), dried by anhydrous sodium sulfate, and filtered, and dried under vacuum. The residues were purified by a silica gel chromatography (100-200 mesh silica gel, petroleum ether:ethyl acetate=5:1 to 1:1) to obtain 1-[[7-(tosyl)pyrrolo[2,3-d]pyrimidin-4-yl)amino]piperidyl-4-carboxylic acid ethyl ester (9.50 g, yield was 44.28%) which was pale yellow solid. The value of $C_{21}H_{25}N_5O_4S$ $[M+H]^+$ 444 was calculated using MS ESI, and was 444.

Step 4: 1-[[7-(tosyl)pyrrolo[2,3-d]pyrimidin-4-yl)amino]piperidyl-4-carboxylic acid ethyl ester (8.80 g, 19.84 mmol) was dissolved in tetrahydrofuran (150 mL), and then sodium hydride (1.19 g, 29.76 mmol) was added in batches at 0° C. under nitrogen protection. The mixture was stirred for 30 min at 25° C., and cooled to 0° C., dropwise added with methyl iodide (4.22 g, 29.76 mmol, 1.50 Eq), and stirred to react for 2 h at 25° C. TLC showed that the reaction was completed. The mixture was cooled to 0° C., and water (20 mL) was added to quench. The aqueous phase was extracted using ethyl acetate (100 mL×2), merged organic phases were washed by saturated saline solution (20 mL), dried by anhydrous sodium sulfate, filtered, and concentrated under reduced pressure. Residues were purified by a silica gel chromatography (100-200 mesh silica gel, petroleum ether: ethyl acetate=3:1-2:1) to obtain 1-[methyl-[7-(tosyl)pyrrolo[2,3-d]pyrimidin-4-yl]amino]piperidyl-4-carboxylic acid ethyl ester (4.10 g, yield was 45.17%) which was pale yellow solid. The value of $C_{22}H_{27}N_5O_4S[M+H]^+$ 458 was calculated using MS ESI, and was 458.

Step 5: 1-[methyl-[7-(tosyl)pyrrolo[2,3-d]pyrimidin-4-yl]amino]piperidyl-4-carboxylic acid ethyl ester (500.00 mg, 1.09 mmol) was dissolved in a mixed solvent of tetrahydrofuran (10 mL) and methanol (10 mL), and a water solution (5 mL) of sodium hydroxide (87.20 mg, 2.18 mmol) was added. The mixture was stirred for 30 min at 100° C. TLC showed that the reaction was completed. The mixture was cooled to 25° C., and then concentrated under reduced pressure at 50° C. Residues were neutralized by an aqueous solution of diluted hydrochloric acid and concentrated under reduced pressure to obtain 1-[methyl(7H-pyrrolo[2,3-d]pyrimidin-4-yl)amino]piperidyl-4-carboxylic acid (400.00 mg, crude product) which was buff solid and directly used in next reaction. The value of $C_{13}H_{17}N_5O_2[M+H]^+$ 276 was calculated using MS ESI, and was 276.

Step 6: 1-[methyl(7H-pyrrolo[2,3-d]pyrimidin-4-yl)amino]piperidyl-4-carboxylic acid (150.00 mg, 544.84 umol) was dissolved in DMF (4 mL) at 25° C. and added with HOBt (88.34 mg, 653.81 umol) and EDCI (125.34 mg, 653.81 umol). The mixture was stirred for 30 min at 25° C., then added with 2-aminoacetonitrile (60.50 mg, 653.81 umol, 1.20 Eq) and triethylamine (220.53 mg, 2.18 mmol, 4.00 Eq), and continuously stirred to react for 12 h at this temperature. LC-MS showed the reaction was completed. The mixture was concentrated under reduced pressure, then residues were purified through a alkalic type HPLC to obtain WX20 (35 mg, 25%). $^1$H NMR (400 MHz, METHANOL-$d_4$) δ=8.12 (s, 1H), 7.14 (d, J=3.5 Hz, 1H), 7.09 (d, J=3.5 Hz, 1H), 4.19 (s, 2H), 3.22 (s, 3H), 3.05-2.96 (m, 4H), 2.30 (d, J=12.0 Hz, 1H), 2.16-2.04 (m, 2H), 2.01-1.91 (m, 2H). The value of $C_{18}H_{19}N_7O[M+H]^+$ 314 was calculated using MS ESI, and was 314.

Embodiment 19

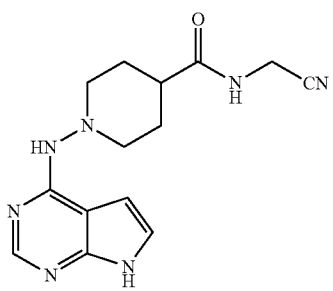

WX21

WX21 was prepared using a preparation method similar to that in Embodiment 18, and a crude product was purified through a preparation type HPLC to obtain WX21. $^1$H NMR (400 MHz, METHANOL-d$_4$) δ=8.08 (s, 1H), 7.13 (d, J=33 Hz, 1H), 6.93 (br. s., 1H), 4.62 (br. s., 1H), 4.18 (s, 2H), 3.23 (d, J=93 Hz, 2H), 2.68 (br. s., 2H), 2.34 (br. s., 1H), 2.10-1.98 (m, 2H), 1.97-1.89 (m, 2H). The value of $C_{14}H_{17}N_7O[M+H]^+$ 300 was calculated using MS ESI, and was 300.

Embodiment 20

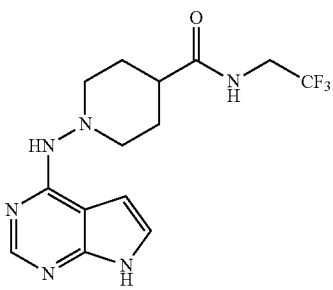

WX22

WX22 was prepared using a preparation method similar to that in Embodiment 18, and a crude product was purified through a preparation type HPLC to obtain WX22. $^1$H NMR (400 MHz, METHANOL-d$_4$) δ=8.08 (s, 1H), 7.12 (d, J=33 Hz, 1H), 6.94 (br. s., 1H), 3.94 (q, J=93 Hz, 2H), 3.23 (d, J=10.0 Hz, 2H), 2.68 (t, J=102 Hz, 2H), 2.41-2.29 (m, 1H), 2.10-1.98 (m, 2H), 1.96-1.87 (m, 2H). The value of $C_{14}H_{17}F_3N_6O[M+H]^+$ 343 was calculated using MS ESI, and was 343.

Embodiment 21

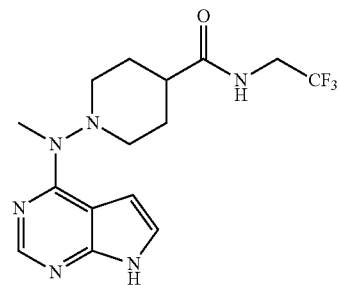

WX23

WX23 was prepared using a preparation method similar to that in Embodiment 18, and a crude product was purified through a preparation type HPLC to obtain WX23. $^1$H NMR (400 MHz, METHANOL-d$_4$) δ=8.12 (s, 1H), 7.14 (d, J=3.5 Hz, 1H), 7.08 (d, J=3.3 Hz, 1H), 3.95 (q, J=9.5 Hz, 2H), 3.21 (s, 3H), 3.05-2.95 (m, 4H), 2.32 (d, J=12.5 Hz, 1H), 2.17-2.05 (m, 2H), 1.94 (d, J=11.8 Hz, 2H). The value of $C_{15}H_{19}F_3N_6O[M+H]^+$ 357 was calculated using MS ESI, was 357.

Embodiment 22

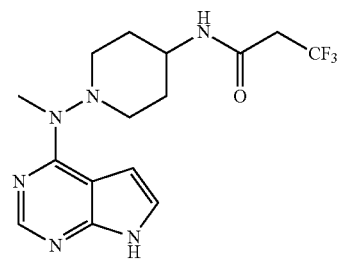

WX24

WX24 was prepared using a preparation method similar to that in Embodiment 18, and a crude product was purified through a preparation type HPLC to obtain WX24. $^1$H NMR (400 MHz, METHANOL-d$_4$) δ=8.12 (s, 1H), 7.12-7.09 (m, 1H), 7.09-7.06 (m, 1H), 3.84-3.69 (m, 1H), 3.26-3.13 (m, 5H), 3.12-3.02 (m, 2H), 2.98 (br. s., 2H), 2.04 (d, J=11.3 Hz, 2H), 1.95-1.80 (m, 2H). The value of $C_{18}H_{19}F_3N_6O[M+H]^+$ 3557 was calculated using MS ESI, was 357.

Embodiment 23

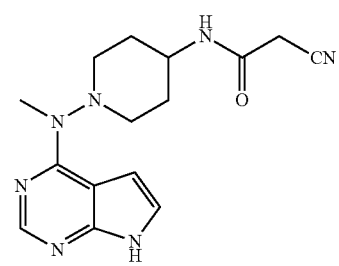

WX25

2-cyano-N-(1-(methyl(7H-pyrrolo[2,3-d]pyrimidin-4-yl)amino)piperidin-4-yl)acetamide

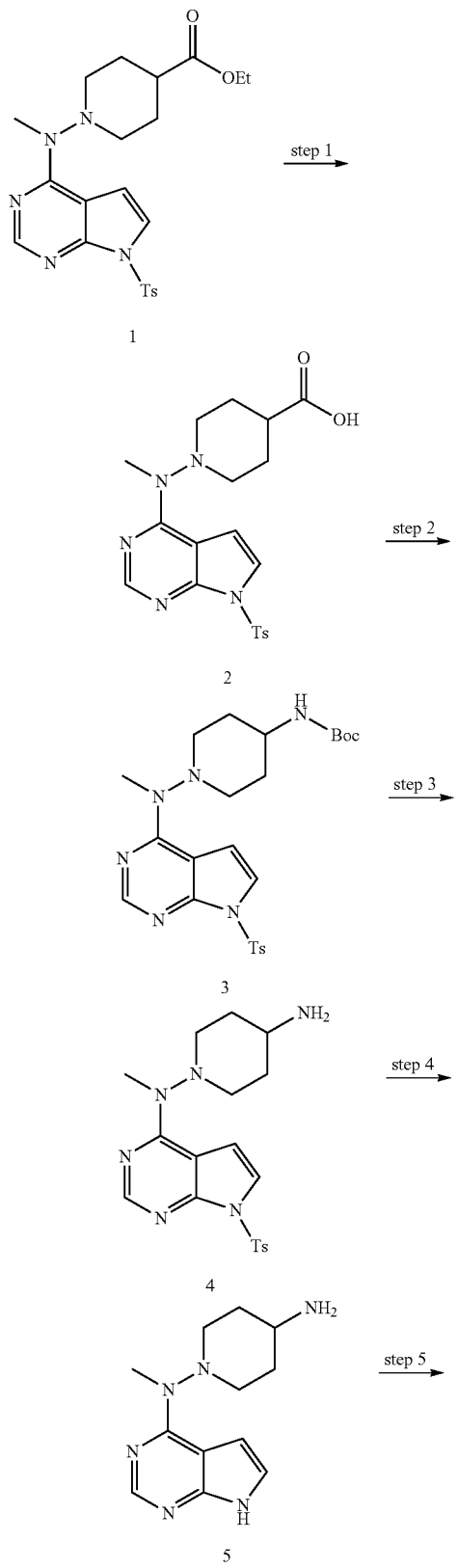

Step 1: 1-[methyl-[7-(tosyl)pyrrolo[2,3-d]pyrimidin-4-yl]amino]piperidyl-4-carboxylic acid ethyl ester (3.50 g, 7.65 mmol) was dissolved in tetrahydrofuran (20 mL) at 25° C., and added with an aqueous solution (20 mL) of lithium hydroxide monohydrate (481.47 mg, 11.47 mmol), the mixture was stirred for 3 h at 25° C. TLC showed that the reaction was completed. The mixture was concentrated under reduced pressure at 40° C. Residues were acidized by an aqueous solution of diluted hydrochloric acid to pH=4-5. The aqueous phase was extracted using ethyl acetate (100 mL×2). Merged organic phases were washed by saturated saline solution (20 mL), dried by anhydrous sodium sulfate, filtered and concentrated under reduced pressure to obtain 1-[methyl-[7-(tosyl)pyrrolo[2,3-d]pyrimidin-4-yl]amino]piperidyl-4-carboxylic acid (3.10 g, yield was 94.35%) which was faint yellow solid. The value of $C_{20}H_{23}N_5O_4S[M+H]^+$ 430 was calculated using MS ESI, and was 430.

Step 2: 1-[methyl-[7-(tosyl)pyrrolo[2,3-d]pyrimidin-4-yl]amino]piperidyl-4-carboxylic acid (2.00 g, 4.66 mmol) and triethylamine (706.82 mg, 6.99 mmol) were dissolved in toluol (100 mL) and stirred for 0.5 h, and then added with [azido(phenoxy)phosphoryl]oxybenzene sulfonic acid (1.28 g, 4.66 mmol) at 25° C. under nitrogen protection, and stirred for 30 min at 25° C., and then heated to 110° C. and stirred for 2 h. LC-MS showed the reaction was completed. The mixture was cooled to 25° C., and ter-butyl alcohol (7.70 g, 103.89 mmol) was added. The mixture was stirred for 12 h at 110° C. TLC showed that the reaction was completed. The mixture was cooled to 25° C., and then concentrated under reduced pressure and at 50° C. Residues were diluted by water (30 mL). The aqueous phase was extracted using ethyl acetate (100 mL×2), merged organic phases were washed by saturated saline water (20 mL×2), dried by anhydrous sodium sulfate, filtered and concentrated under reduced pressure. Residues were purified by a silica gel chromatography (100-200 mesh silica gel, petroleum ether:ethyl acetate=4:1-2:1) to obtain N-[1-[methyl-[7-(tosyl)pyrrolo[2,3-d]pyrimidin-4-yl]amino]-4-piperidinyl]-tert-butyl carbamate (950.00 mg, yield was 40.46%) which was faint yellow solid. The value of $C_{24}H_{32}N_6O_4S[M+H]^+$ 501 was calculated using MS ESI, was 501.

Step 3: N-[1-methyl-[7-(tosyl)pyrrolo[2,3-d]pyrimidin-4-yl]amino]-4-piperidinyl]tert-butyl carbamate (500.00 mg, 998.78 umol) was dissolved in dichloromethane (500.00 mg, 998.78 umol), and then trifluoroacetic acid (500.00 mg, 998.78 umol) was dropwise added. The mixture was stirred for 30 min at 25° C. TLC showed that the reaction was completed. The mixture was concentrated to be dry under reduced pressure at 40° C. Residues obtained were dissolved in water (10 mL), and alkalized by solid sodium bicarbonate to pH=9, and the aqueous phase was extracted using ethyl acetate (50 mL×3). Merged organic phases were washed by saturated saline water (20 mL), dried by anhydrous sodium sulfate, and filtered and concentrated to be dry under reduced pressure to obtain 1-(methyl[7-(tosyl-7H-pyrrolo[2,3-d]pyrimidin-4-yl]piperidyl-4-amine (400 mg, 56%) which was buff solid, and was directly used in next reaction. The value of $C_{19}H_{24}N_6O_2S[M+H]^+$ 401 was calculated using MS ESI, was 401.

Step 4: 1-(methyl[7-(tosyl-7H-pyrrolo[2,3-d]pyrimidin-4-yl]piperidyl-4-amine (400.00 mg, 998.75 umol) was dissolved in a mixed solvent of tetrahydrofuran (10.00 mL) and methanol (10.00 mL), and an aqueous solution (5 mL) of sodium hydroxide (79.90 mg, 2.00 mmol) was added. The mixture was stirred for 1 h at 100° C. LC-MS showed the reaction was completed. The mixture was concentrated under reduced pressure at 40° C., residues were dissolved in water (10 mL), and adjusted by an aqueous solution of diluted hydrochloric acid to pH=9, and concentrated under reduced pressure to obtain 1-(methyl(7H-pyrrolo[2,3-d]pyrimidin-4-yl)amino)piperidyl-4-amine (300 mg, crude product) which was buff solid and directly used in next reaction. The value of $C_{12}H_{18}N_6[M+H]^+$ 247 was calculated using MS ESI, was 247.

Step 5: 2-cyanoacetic acid (49.73 mg, 584.63 umol), HOBt (78.99 mg, 584.63 umol) and EDCI (112.07 mg, 584.63 umol) were dissolved in DMF (4.00 mL). The mixture was stirred for 30 min at 25° C., and then added with 1-(methyl(7H-pyrrolo[2,3-d]pyrimidine-4-yl)amino)piperidyl-4-amine (120.00 mg, 487.19 umol) and triethylamine (98.60 mg, 974.38 umol), and then the mixture was stirred for 24 h at 25° C. LC-MS showed that the reaction was completed, the mixture was concentrated to be dry under reduced pressure and at a temperature lower than 70° C.; and residues obtained were purified through a alkalic type HPLC to obtain WX25 (25 mg, 35%). $^1$H NMR (400 MHz, METHANOL-d$_4$) δ=8.12 (s, 1H), 7.11 (d, J=3.5 Hz, 1H), 7.07 (d, J=3.3 Hz, 1H), 3.75 (br. s., 1H), 3.23 (s, 3H), 3.13-3.04 (m, 2H), 2.99 (br. s., 2H), 2.06 (d, J=10.0 Hz, 2H), 1.96-1.81 (m, 2H). The value of $C_{18}H_{19}N_7O[M+H]^+$ 314 was calculated using MS ESI, and was 314.

Embodiment 24

WX26

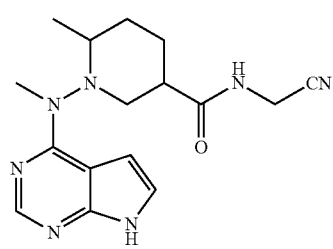

N-(cyanomethyl)-6-methyl-1-(methyl(7H-pyrrolo[2,3-d]pyrimidin-4-yl)amino)piperidyl-3-formamide

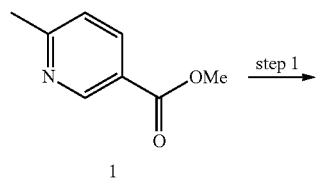

1 → step 1

-continued

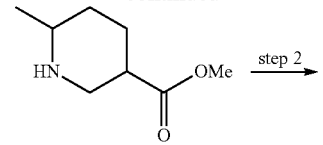

2 → step 2

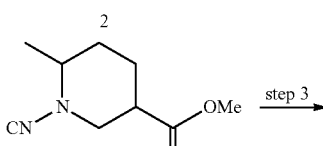

3 → step 3

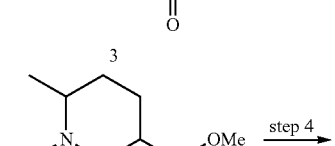

4 → step 4

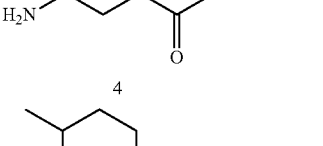

5 → step 5

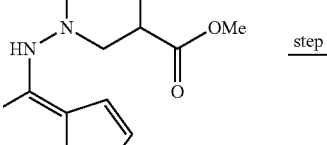

6 → step 6

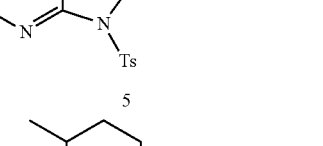

7 → step 7

WX26

Step 1: PtO$_2$ (3.00 g) was added to a methanol solution (200 mL) of methyl 6-methylpyridine-3-carboxylate (18.00 g, 119.08 mmol), and then added with water (10 mL) and hydrochloric acid (20 mL); under H$_2$ (50 psi), the reaction solution was heated to 50° C. and stirred for 15 h. TLC showed that the reactants were completely consumed; then solid were filtered, and the filtrate was concentrated under reduced pressure, residues were dissolved in toluol (100 mL), then the solvent toluol was spin-dried to obtain methyl 6-methylpiperidyl-3-carboxylate which was yellow oily matter (18.00 g, yield was 96.15%). The value of C$_8$H$_{15}$NO$_2$ [M+H]$^+$ 157 was calculated using MS ESI, was 157.

Step 2: Methyl 6-methylpiperidyl-3-carboxylate (25.00 g, 159.02 mmol) was dissolved in water (50 mL) and glacial acetic acid (100 mL), and an aqueous solution (50 mL) of sodium nitrite (21.95 g, 318.05 mmol) was slowly added at 0° C.; the reaction solution was stirred for 1 h at room temperature, diluted by ethyl acetate (100 mL) and water (50 mL), and then separated; the water layer was extracted using ethyl acetate (100 mL×2), merged organic layers were washed by saturated saline solution, dried by sodium sulfate, filtered and concentrated under reduced pressure to obtain a crude product which was purified through a silicagel column (petroleum ether:ethyl acetate=10:1) to obtain methyl 6-methyl-1-nitroso-piperidyl-3-carboxylate which was yellow oily matter (20.00 g, yield was 67.54%). The value of C$_8$H$_{14}$N$_2$O$_3$[M+H]$^+$ 187 was calculated using MS ESI, and was 187.

Step 3: methyl 6-methyl-1-nitroso-piperidyl-3-carboxylatei (21.00 g, 112.78 mmol) and zinc dust (36.87 g, 563.90 mmol) were dissolved in an anhydrous methanol (1100 mL) solution, and was slowly drop wised added with glacial acetic acid (100 mL) at 0° C., wherein the inside temperature was kept to be lower than 5° C., then the mixture was stirred for 1 h at 0° C. Afterwards, the solvent was concentrated under reduced pressure, and then the reaction solution was adjusted by saturated sodium bicarbonate solution to pH=7, and then extracted using ethyl acetate (200 mL×3). Merged organic layers were dried and concentrated to obtain methyl 1-amino-6-methyl-piperidyl-3-carboxylate which was yellow oily matter (18.00 g, yield was 92.67%). The value of C$_8$H$_{16}$N$_2$O$_2$[M+H]$^+$ 173 was calculated using MS ESI, and was 173 Step 4: methyl 1-amino-6-methyl-piperidyl-3-carboxylate (15.00 g, 46.16 mmol) and 4-chloro-7-(tosyl)pyrrolo[2,3-d]pyrimidine (20.00 g, 64.99 mmol) were dissolved in a dioxane solution (200 mL), and added with solid caesium carbonate (15.04 g, 46.16 mmol) under nitrogen protection at 20° C.; the reaction solution was heated to 110° C. and stirred for 20 h. The mixture was cooled to 20° C., and the solvent was concentrated to be dry under reduced pressure. The residues were purified by a silica gel chromatography (petroleum ether:ethyl acetate=1:1) to obtain methyl 6-methyl-1-[[7-(tosyl)pyrrolo[2,3-d]pyrimidin-4-yl]amino]piperidyl-3-carboxylate (3.50 g, yield was 17.10%) which was white solid. The value of C$_{21}$H$_{25}$N$_5$O$_4$S[M+H]$^+$ 444 was calculated using MS ESI, and was 444.

Step 5: NaH (288.80 7.22 mmol) was added into a THF (50 mL) solution of methyl 6-methyl-1-[[7-(tosyl)pyrrolo[2,3-d]pyrimidin-4-yl]amino]piperidyl-3-carboxylatei (1.60 g, 3.61 mmol) under nitrogen protection at 0° C.; the mixture was stirred for 20 min at 0° C., and dropwise added with MeI (1.02 g, 7.22 mmol), and then stirred for 1 h at 20° C. LCMS showed that the reaction was completed. The reaction solution was poured into a mixed solution of DCM (50 mL) and water (50 mL), and then stood for lamination. The aqueous phase was extracted using DCM (50 mL×3). Merged organic phases were washed by saturated saline solution (100 mL), dried by anhydrous sodium sulfate, filtered and concentrated to be dry under reduced pressure. The residues were purified by a silica gel chromatography (petroleum ether:ethyl acetate==10/1 to 1/1) to obtain methyl 6-methyl-1-[methyl-[7-(tosyl)pyrrolo[2,3-D]pyrimidin-4-yl)amino]piperidyl-3-carboxylate (1.50 g, yield was 90.81%) which was yellow solid. The value of C$_{22}$H$_{27}$N$_5$O$_4$S[M+H]$^+$ 458 was calculated using MS ESI, and was 458.

Step 6: NaOH (656.00 mg, 16.40 mmol) was added into a mixed solution of THF (20 mL) and water (10 mL) of methyl 6-methyl-1-[methyl-[7-(tosyl)pyrrolo[2,3-D]pyrimidin-4-yl)amino]piperidyl-3-carboxylate (1.50 g, 3.28 mmol) at 20° C.; and the reaction solution was heated to 60° C. and stirred for 15 h. MeOH (10 mL) was added, and then the mixture was heated to 80° C., and stirred for 3 h. LCMS showed that the reaction was completed. The mixture was cooled to 20° C., adjusted by HCl (6 M) to pH=7, and then concentrated under reduced pressure to obtain 6-methyl-1-[methyl-(7H-pyrrolo[2,3-d]pyrimidin-4-yl)amino]piperidyl-3-carboxylic acid (1.80 g, crude product) which was white solid. The value of C$_{14}$H$_{19}$N$_5$O$_2$[M+H]$^+$ 290 was calculated using MS ESI, and was 290.

Step 7: EDCI (331.28 mg, 1.73 mmol) and HOBt (233.51 mg, 1.73 mmol) were added into a DMF solution (5 mL) of 6-methyl-1-[methyl-(7H-pyrrolo[2,3-d]pyrimidin-4-yl)amino]piperidyl-3-carboxylic acid (250.00 mg, 864.07 umol). The mixture was stirred for 5 min at 20° C., then 2-aminoacetonitrile (72.67 mg, 1.30 mmol) and TEA (437.18 mg, 4.32 mmol) were added, and the mixture was stirred for 15 h at 20° C. LCMS showed that the reaction was completed. The mixture was filtered and purified through a preparation type HPLC (acidic condition: 0.1% TFA) to obtain WX26: N-(cyanomethyl)-6-methyl-1-[methyl(7H-pyrrolo[2,3-d]pyrimidin-4-yl)amino]piperidyl-3-formamide (61.95 mg, yield was 21.90%). $^1$H NMR (400 MHz, Methanol-d$_4$) δ=8.48 (s, 1H), 7.47 (d, J=3.6 Hz, 1H), 7.01 (d, J=3.6 Hz, 1H), 4.25-4.35 (m, 2H), 3.59 (s, 3H), 3.17-3.24 (m, 1H), 3.09-3.16 (m, 1H), 2.99-3.08 (m, 1H), 2.95 (br. s., 1H), 2.04-2.14 (m, 1H), 1.78-1.96 (m, 2H), 1.45-1.59 (m, 1H), 0.99 (d, J=6.4 Hz, 3H). The value of C$_{16}$H$_{21}$N$_7$O[M+H]$^+$ 328 was calculated using MS ESI, and was 328.

Embodiment 25

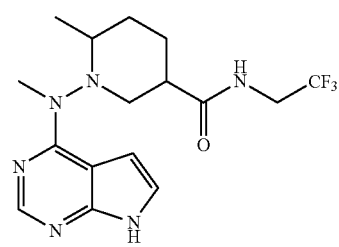

WX27

6-methyl-1-(methyl(7H-pyrrole[2,3-d]pyrimidin-4-yl)amino)-N-(2,2,2-trifluoroethyl)piperidyl-3-formamide 2-methyl-7-(7H-pyrrolo[2,3-d]pyrimidin-4-yl)-1,7-diazabicyclo[3.2.1]octan-6-one

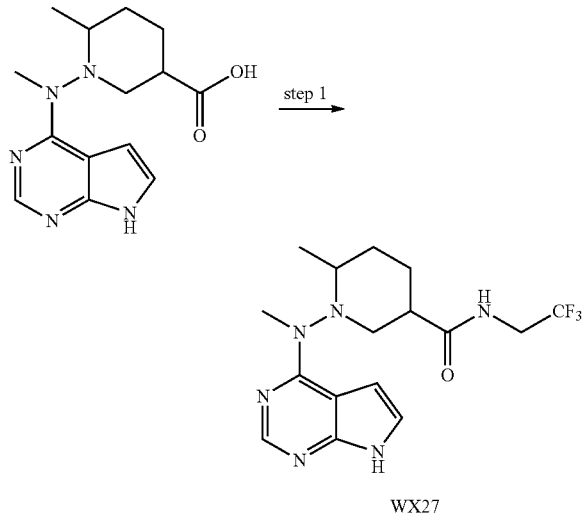

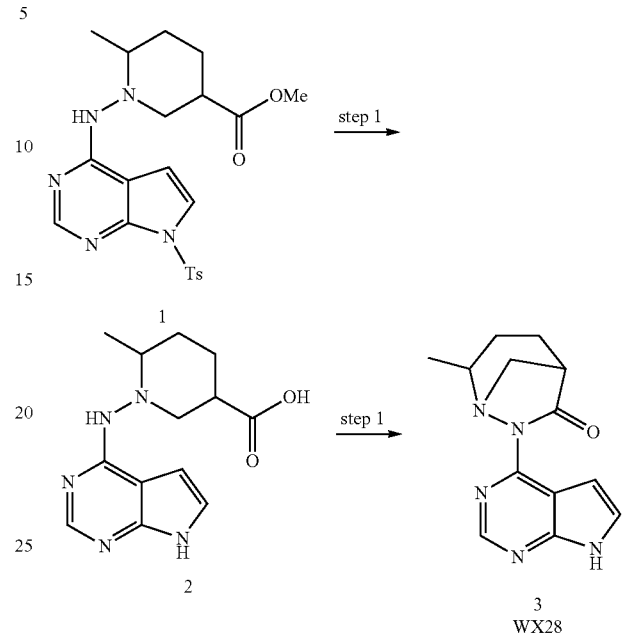

Step 1: EDCI (331.28 mg, 1.73 mmol) and HOBt (233.51 mg, 1.73 mmol) was added into a DMF solution (5 mL) of 6-methyl-1-[methyl-(7H-pyrrolo[2,3-d]pyrimidin-4-yl)amino]piperidyl-3-carboxylic acid (250.00 mg, 864.07 umol), the mixture was stirred for 5 min at 20° C., and then added with 2,2,2-trifluoroacetonitrile (128.38 mg, 1.30 mmol) and TEA (437.18 mg, 4.32 mmol); the mixture was stirred for 15 h at 20° C. LCMS showed that the reaction was completed. The mixture was filtered and purified through a preparation type HPLC (acidic condition: 0.1% TFA) to obtain WX27:

6-methyl-1-(methyl(7H-pyrrole[2,3-d]pyrimidin-4-yl)amino)-N-(2,2,2-trifluoroethyl)piperidyl-3-formamide (81.80 mg, yield was 25.56%). $^1$H NMR (400 MHz, Methanol-$d_4$) δ=8.88 (br. s., 1H), 8.46 (s, 1H), 7.45 (d, J=3.6 Hz, 1H), 6.99 (d, J=3.6 Hz, 1H), 4.10-4.27 (m, 1H), 3.86-4.02 (m, 1H), 3.58 (s, 3H), 3.09-3.21 (m, 2H), 2.98-3.08 (m, 1H), 2.96 (br. s., 1H), 2.10 (d, J=13.6 Hz, 1H), 1.76-1.97 (m, 2H), 1.42-1.57 (m, 1H), 0.98 (d, J=6.0 Hz, 3H). The value of $C_{14}H_{19}F_3N_6O[M+H]^+$ 345 was calculated using MS ESI, and was 345.

Step 1: NaOH (270.00 mg, 6.75 mmol) was added into a mixed solution of THF (20 mL) and water (10 mL) of methyl 6-methyl-1-[methyl-[7-(tosyl)pyrrolo[2,3-d]pyrimidin-4-yl)amino]piperidyl-3-carboxylate (600.00 mg, 1.35 mmol) at 20° C.; and the reaction solution was heated to 60° C. and stirred for 2 h. Then MeOH (10 mL) was added, heated to 80° C., and stirred for 2 h. LCMS showed that the reaction was completed. The mixture was cooled to 20° C., adjusted by HCl (6 M) to pH=7, and then concentrated in vacuum to obtain 6-methyl-1-[methyl-(7H-pyrrolo[2,3-d]pyrimidin-4-yl-amino)piperidyl-3-carboxylic acid (600.00 mg, crude product) which was white solid. The value of $C_{13}H_{17}N_5O_2[M+H]^+$ 276 was calculated using MS ESI, and was 276.

Step 2: HATU (513.77 mg, 1.35 mmol) was added into a DMF solution (5 mL) of 6-methyl-1-(7H-pyrrolo[2,3-d]pyrimidin-4-yl-amino) piperidyl-3-carboxylic acid at 20° C.; the reaction solution was stirred for 5 min, and then added with 2-aminoacetonitrile (56.82 mg, 1.01 mmol) and TEA (341.82 mg, 3.38 mmol), and stirred for 1 h at 20° C. LCMS showed that the original raw materials were completely consumed. The mixture was poured into DCM (50 mL) and water (10 mL), organic phases were washed by saturated saline solution (50 mL×3), then the organic layer was dried by anhydrous sodium sulfate, filtered and concentrated under reduced pressure to obtain a crude product which was purified through a preparation type HPLC (alkalic condition: 0.1% NH3.H2O) to obtain WX28: 2-methyl-7-(7H-pyrrolo[2,3-d]pyrimidin-4-yl)-1,7-diazabicyclo[3.2.1]octan-6-one (12.30 mg, yield was 7.08%). $^1$H NMR (400 MHz, DMSO-$d_6$) δ=8.50 (s, 1H), 7.39-7.46 (m, 1H), 6.67-6.74 (m, 1H), 5.78 (d, J=5.6 Hz, 1H), 3.81 (dd, J=4.0, 11.2 Hz, 1H), 2.20 (t, J=1.2 Hz, 1H), 1.96 (dd, J=3.2, 6.0 Hz, 2H), 1.59-1.82 (m, 2H), 1.47 (q, J=1.2 Hz, 1H), 0.96 (t, J=1.2 Hz, 1H), 0.64 (d, J=6.8 Hz, 3H). The value of $C_{13}H_{15}N_5O[M+H]^+$ 257 was calculated using MS ESI, and was 257.

Embodiment 26

WX28

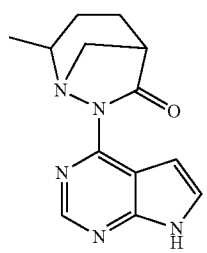

Embodiment 27

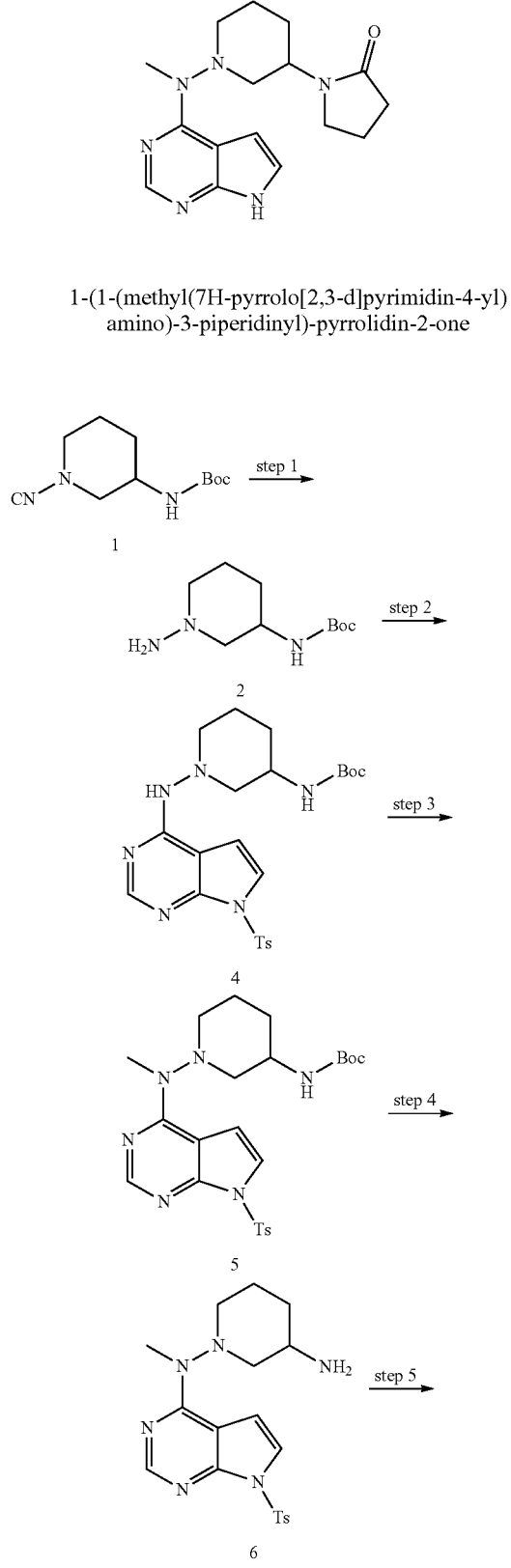

1-(1-(methyl(7H-pyrrolo[2,3-d]pyrimidin-4-yl)amino)-3-piperidinyl)-pyrrolidin-2-one

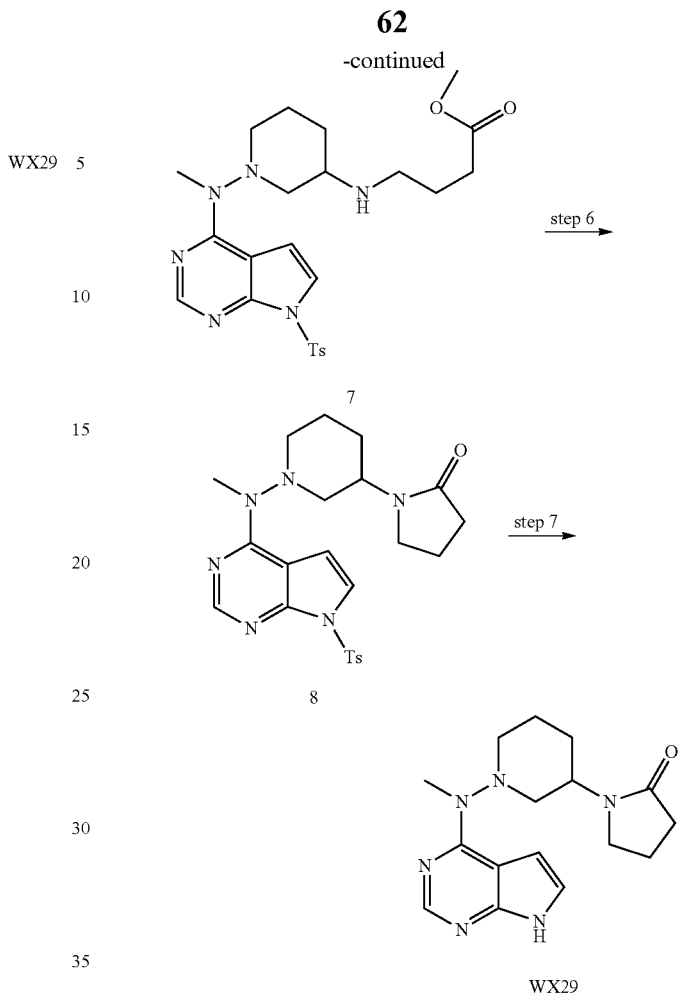

Step 1: tert-butyl N-(1-nitroso-3-piperidinyl) carbamate (5.00 g, 21.81 mmol) and zinc dust (7.13 g, 109.05 mmol) were dissolved in anhydrous methanol (30 mL), dropwise added with glacial acetic acid (30 mL) at −10° C.; after the glacial acetic acid was dropwise added in 1 h, the mixture was stirred for 30 min at −10° C., and then was warmed up to 25° C., and stirred for 2 h. TLC showed that the reaction was completed. Solids were filtered out, and residues were concentrated under reduced pressure, then water (5 mL) was added and the aqueous phase was adjusted by a saturated sodium dicarbonate solution (100 mL) to pH=8-9, then was extracted by dichloromethane:methanol (5/1; 50 mL×3). The merged organic phases were washed by saturated saline water (50 mL), dried by anhydrous sodium sulfate, filtered, and concentrated under reduced pressure to obtain tert-butyl N-(1-amino-3-piperidinyl)carbamate (1.80 g, crude product) which was buff oily matter and directly used in next reaction without further purification. The value of $C_{10}H_{21}N_3O_2[M+H]^+$ 216 was calculated using MS ESI, and was 216.

Step 2: tert-butyl N-(1-amino-3-piperidinyl) carbamate (1.80 g, 8.36 mmol) and 4-chloro-7-(tosyl)pyrrolo[2,3-d]pyrimidine (2.83 g, 9.20 mmol) were dissolved in a dichloromethane solution (20 mL), and added with triethylamine (2.54 g, 25.08 mmol), then the reaction solution was heated to 60° C. and stirred for 10 h. LCMS showed that the reaction was completed. The mixture was cooled to 25° C., and the solvent was concentrated to be dry under reduced pressure. Residues were poured into water (20 mL), the aqueous phase was extracted using ethyl acetate (30 mL×3), merged organic phases were washed by saturated saline solution (15 mL×2), dried by anhydrous sodium sulfate, and filtered and concentrated in vacuum. Residues were purified by silica column chromatography (dichloromethane/ethyl acetate=5:1/3:1) to obtain tert-butyl N-[1-[[7-(tosyl)pyrrolo[2,3-d]pyrimidin-4-yl)amino]-3-piperidyl] carbamate which was yellow spumescent solid (1.83 g, yield was 43.18%). The value of $C_{23}H_{30}N_6O_4S[M+H]^+$ 487 was calculated using MS ESI, and was 487.

Step 3: a solution of tert-butyl N-[1-[[7-(tosyl)pyrrolo[2,3-d]pyrimidin-4-yl)amino]-3-piperidyl]tcarbamate (1.80 g, 3.70 mmol) (25 mL) was dropwise added to a tetrahydrofuran suspension (25 mL) dissolved with sodium hydride (60%, 162.80 mg, 4.07 mmol) at 0° C. The mixture was stirred for 30 min under nitrogen protection at 0° C., then methyl iodide (577.70 mg, 4.07 mmol) was dropwise added. After the methyl iodide was dropwise added completely, the reaction solution was warmed up to a normal temperature and stirred for 1 h. LCMS showed that the reaction was completed. The mixture was quenched by saturated ammonium chloride solution (10 mL) and extracted using ethyl acetate (30 mL×2). Merged organic phases were washed by saturated saline solution (15 mL), dried by anhydrous sodium sulfate, filtered and concentrated in vacuum. Residues were purified by a silica gel chromatography (petroleum ether:ethyl acetate=3:1) to obtain tert-butyl N-[1-[methyl-[7-(tosyl)pyrrolo[2,3-d]pyrimidin-4-yl]amino]-3-piperidinyl] carbamate (900.00 mg, yield was 48.59%) which was faint spumescent solid. The value of $C_{24}H_{32}N_6O_4S[M+H]^+$ 501 was calculated using MS ESI, was 501.

Step 4: hydrochloric acid/dioxane (20 mL) was added into a DCM solution (5 mL) of tert-butyl N-[1-[methyl-[7-(tosyl)pyrrolo[2,3-d]pyrimidin-4-yl]amino]-3-piperidinyl]carbamate (900.00 mg, 1.80 mmol) at 0° C., then the mixture was heated to 30° C. and stirred for 1 h. Solid was formed, and TLC showed that the reaction was completed. The mixture was concentrated under reduced pressure to obtain N-methyl-N-[7-(tosyl)-7H-pyrrolo[2,3-d]pyrimidin-4-yl]amino]piperidyl-3-amine hydrochloride (900.00 mg, crude product) which was buff solid. The product was directly used in next step without purification. The value of $C_{19}H_{24}N_6O_2S[M+H]^+$ 401, was calculated using MS ESI, was 401.

Step 5: N-methyl-N-[7-(tosyl)-7H-pyrrolo[2,3-d]pyrimidine-4-yl]amino]piperidyl-3-amine hydrochloride (400 mg, 0.9 mmol) and methyl-4-oxobutyric acid (159.43 mg, 1.37 mmol) were dissolved in. anhydrous methanol (10 mL), and sodium acetoxyborohydride (388.03 mg, 1.83 mmol) was added in batches at normal temperature. The reaction solution was stirred to react for 10 h at 28° C. LC-MS showed that a new product was generated. Redundant solvent was spin-dried, residues were poured into water (10 mL) and saturated sodium bicarbonate (10 mL) solution, and the aqueous phase was extracted using ethyl acetate (30 mL×2). Merged organic phases were washed by saturated saline water (10 mL), dried by anhydrous sodium sulfate, and filtered and concentrated in vacuum to obtain methyl 4-[[1-[methyl-[7-(tosyl)pyrrolo[2,3-d]pyrimidin-4-yl]amino]-3-piperidinyl]amino]butyrate (600.00 mg, crude product) which was yellow oily matter, and was directly used in next reaction without further purification. The value of $C_{24}H_{32}N_6O_4S[M+H]^+$ 501 was calculated using MS ESI, was 501.

Step 6: N-methyl pyrrolidone (20 mL) solution of methyl 4-[[1-[methyl-[7-(tosyl)pyrrolo[2,3-d]pyrimidin-4-yl]amino]-3-piperidinyl]amino]butyrate (1.00 g, 2.00 mmol) was heated to 140° C. and stirred for 5 h. LCMS showed that the reaction was completed. The mixture was cooled to 30° C., and poured into water (50 mL), and the aqueous phase was extracted using ethyl acetate (20 mL×3). Merged organic phases were washed by saturated saline solution (10 mL×2), dried by anhydrous sodium sulfate, filtered and concentrated in vacuum. The residues were purified by a silica gel chromatography (petroleum ether:ethyl acetate=3:1 to 1:1) to obtain 1-[1-[methyl-[7-(tosyl)pyrrolo[2,3-d]pyrimidin-4-yl]amino]-3-piperidinyl]pyrrolid-2-one (385.00 mg, yield was 36.97%) which was yellow solid. The value of C23H28N6O3S[M+H]+ 469 was calculated using MS ESI, and was 469.

Step 7: 1-[1-[methyl-[7-(tosyl)pyrrolo[2,3-d]pyrimidin-4-yl]amino]-3-piperidinyl]pyrrolid-2-one (100.00 mg, 213.42 umol) was dissolved in a mixed solution of MeOH (3 mL) and water (3 mL), and added with potassium carbonate (88.49 mg, 640.26 umol), then the mixture was heated to 80° C. and stirred for 2 h. LCMS showed that the reaction was completed. The mixture was cooled to 30° C., and was concentrated to be dry under reduced pressure. Residues were poured into water (5 mL), and the aqueous phase was extracted by dichloromethane:methanol (5:1, 10 mL×3). Merged organic phases were washed by saturated saline solution (10 mL×2), dried by anhydrous sodium sulfate, filtered and concentrated in vacuum. Residues were purified through a preparation type HPLC ($NH_3.H_2O$) to obtain WX29: 1-[1-[methyl(7H-pyrrolo[2,3-d]pyrimidin-4-yl)amino]-3-piperidinyl]pyrrolid-2-one (28.00 mg, yield was 41.73%). $^1$H NMR (400 MHz, MeOD-$d_4$) δ=8.07-8.13 (m, 1H), 7.03-7.10 (m, 2H), 4.28-4.46 (m, 1H), 3.44-3.56 (m, 2H), 3.22 (s, 3H), 2.81-3.07 (m, 4H), 2.30-2.42 (m, 2H), 1.77-2.09 (m, 5H), 1.45-1.62 (m, 1H). The value of $C_{16}H_{22}N_6O[M+H]^+$ 315 was calculated using MS ESI, and was 315.

Embodiment 28

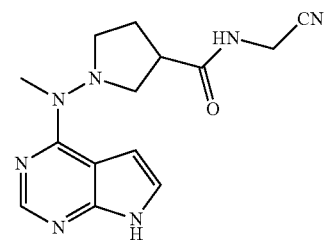

WX30

N-(cyanomethyl)-1-[methyl(7H-pyrrolo[2,3-d]pyrimidin-4-yl)amino]pyrrolidyl-3-formamide

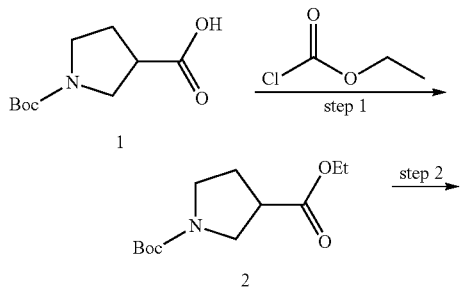

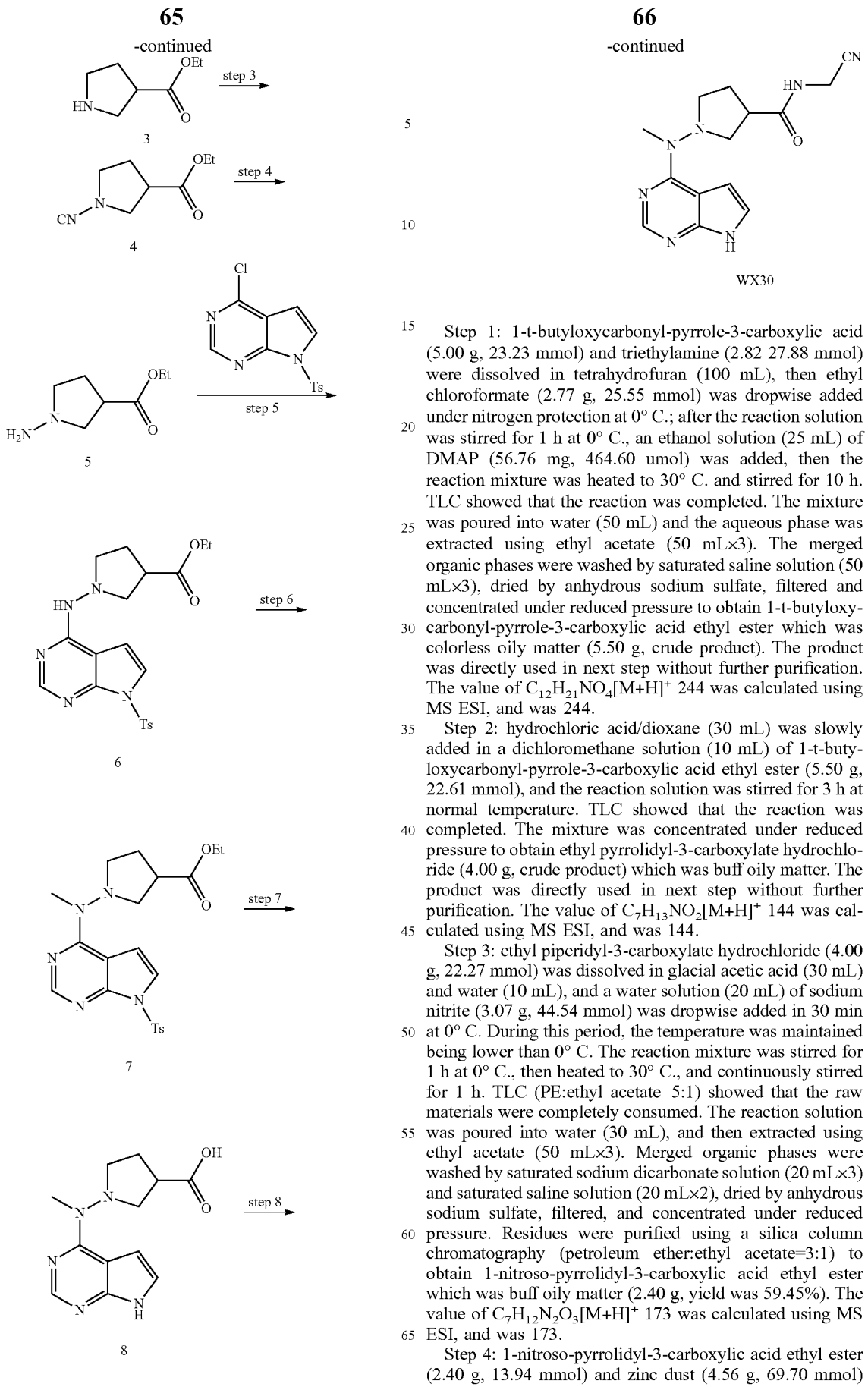

Step 1: 1-t-butyloxycarbonyl-pyrrole-3-carboxylic acid (5.00 g, 23.23 mmol) and triethylamine (2.82 27.88 mmol) were dissolved in tetrahydrofuran (100 mL), then ethyl chloroformate (2.77 g, 25.55 mmol) was dropwise added under nitrogen protection at 0° C.; after the reaction solution was stirred for 1 h at 0° C., an ethanol solution (25 mL) of DMAP (56.76 mg, 464.60 umol) was added, then the reaction mixture was heated to 30° C. and stirred for 10 h. TLC showed that the reaction was completed. The mixture was poured into water (50 mL) and the aqueous phase was extracted using ethyl acetate (50 mL×3). The merged organic phases were washed by saturated saline solution (50 mL×3), dried by anhydrous sodium sulfate, filtered and concentrated under reduced pressure to obtain 1-t-butyloxycarbonyl-pyrrole-3-carboxylic acid ethyl ester which was colorless oily matter (5.50 g, crude product). The product was directly used in next step without further purification. The value of $C_{12}H_{21}NO_4[M+H]^+$ 244 was calculated using MS ESI, and was 244.

Step 2: hydrochloric acid/dioxane (30 mL) was slowly added in a dichloromethane solution (10 mL) of 1-t-butyloxycarbonyl-pyrrole-3-carboxylic acid ethyl ester (5.50 g, 22.61 mmol), and the reaction solution was stirred for 3 h at normal temperature. TLC showed that the reaction was completed. The mixture was concentrated under reduced pressure to obtain ethyl pyrrolidyl-3-carboxylate hydrochloride (4.00 g, crude product) which was buff oily matter. The product was directly used in next step without further purification. The value of $C_7H_{13}NO_2[M+H]^+$ 144 was calculated using MS ESI, and was 144.

Step 3: ethyl piperidyl-3-carboxylate hydrochloride (4.00 g, 22.27 mmol) was dissolved in glacial acetic acid (30 mL) and water (10 mL), and a water solution (20 mL) of sodium nitrite (3.07 g, 44.54 mmol) was dropwise added in 30 min at 0° C. During this period, the temperature was maintained being lower than 0° C. The reaction mixture was stirred for 1 h at 0° C., then heated to 30° C., and continuously stirred for 1 h. TLC (PE:ethyl acetate=5:1) showed that the raw materials were completely consumed. The reaction solution was poured into water (30 mL), and then extracted using ethyl acetate (50 mL×3). Merged organic phases were washed by saturated sodium dicarbonate solution (20 mL×3) and saturated saline solution (20 mL×2), dried by anhydrous sodium sulfate, filtered, and concentrated under reduced pressure. Residues were purified using a silica column chromatography (petroleum ether:ethyl acetate=3:1) to obtain 1-nitroso-pyrrolidyl-3-carboxylic acid ethyl ester which was buff oily matter (2.40 g, yield was 59.45%). The value of $C_7H_{12}N_2O_3[M+H]^+$ 173 was calculated using MS ESI, and was 173.

Step 4: 1-nitroso-pyrrolidyl-3-carboxylic acid ethyl ester (2.40 g, 13.94 mmol) and zinc dust (4.56 g, 69.70 mmol)

were dissolved in anhydrous methanol solution (15 mL), then the reaction solution was cooled to −10° C., and glacial acetic acid (15 mL) was dropped slowly in 30 min. The reaction solution was stirred for 30 min at −10° C., heated to 30° C. and stirred for 1 h. TLC showed that the reaction was completed. Solid was filtered out, and the filtrate was concentrated under reduced pressure to obtain a crude product. The crude product was dissolved in water (10 mL), the aqueous phase was neutralized by saturated solid sodium dicarbonate to pH=7-8, and was extracted by dichloromethane:methanol (5:1, 200 mL×2). Merged organic phases were washed by saturated saline solution (50 mL×2), dried by anhydrous sodium sulfate, filtered and concentrated in vacuum to obtain 1-aminopyrrolidyl-3-carboxylic acid ethyl ester (1.60 g, crude product) which was faint yellow oily matter. The product was directly used in next step without purification. The value of $C_7H_{14}N_2O_2[M+H]^+$ 159 was calculated using MS ESI, and was 159.

Step 5: 1-aminopyrrolidyl-3-carboxylic acid ethyl ester (1.60 g, 10.11 mmol) and 4-chloro-7-(tosyl)pyrrolo[2,3-d]pyrimidine (3.42 g, 11.12 mmol) were dissolved in a dichloromethane solution (20 mL), and added with triethylamine (3.07 g, 30.33 mmol), then the reaction solution was heated to 60° C. and stirred for 10 h. LCMS showed that the reaction was completed. The solvent was spin-dried, residues were poured into water (20 mL), and an aqueous phase was extracted using ethyl acetate (20 mL×3). Merged organic phases were washed by saturated saline solution (15 mL×2), dried by anhydrous sodium sulfate, filtered and concentrated to be dry under reduced pressure. Residues were purified by silica column chromatography (dichloromethane:ethyl acetate=5:1 to 3:1) to obtain 1-((7-tosyl-7H-pyrrolo[2,3-d]pyrimidin-4-yl)amino)piperidyl-3-carboxylic acid ethyl ester which was yellow solid (1.00 g, yield was 22.11%). The value of $C_{20}H_{23}N_5O_4S[M+H]^+$ 430 was calculated using MS ESI, was 430.

Step 6: 1-((7-tosyl-7H-pyrrolo[2,3-d]pyrimidin-4-yl)amino)piperidyl-3-carboxylic acid ethyl ester (1.00 g, 2.33 mmol) was dropwise added to a tetrahydrofuran suspension (15 mL) of NaH (60%, 112.00 mg, 2.80 mmol) under nitrogen protection at 0° C. in 30 min, then the reaction solution was stirred for 1 h at 0° C., and added with methyl iodide (396.86 mg, 2.80 mmol). The reaction solution was warmed up to 25° C. and stirred for 1 h. TLC showed that the reaction was completed. The reaction solution was quenched by saturated ammonium chloride solution (10 mL) and the aqueous phase was extracted using ethyl acetate (30 mL×2). Merged organic phases were washed by saturated saline solution (10 mL), dried by anhydrous sodium sulfate, filtered and concentrated in vacuum. Residues were purified by silica column chromatography (petroleum ether:ethyl acetate=5/1 to 3/1) to obtain 1-(methyl-1-(7-tosyl-7H-pyrrolo[2,3-d]pyrimidin-4-yl)amino)piperidyl-3-carboxylic acid ethyl ester which was faint yellow spumescent solid (220.00 mg, yield was 17.67%). The value of $C_{21}H_{25}N_5O_4S$ $[M+H]^+$ 444 was calculated using MS ESI, and was 444.

Step 7: 1-(methyl-1-(7-tosyl-7H-pyrrolo[2,3-d]pyrimidine-4-yl)amino)piperidyl-3-carboxylic acid ethyl ester (220.00 mg, 496.03 umol) was dissolved in a mixed solution of tetrahydrofuran (5 mL) and water (2 mL), added with sodium hydroxide (79.36 mg, 1.98 mmol), and then the reaction solution was heated to 60° C. and stirred for 10 h. LCMS showed that the reaction was completed. The reaction solution was cooled to 25° C., and concentrated under reduced pressure. The aqueous phase was adjusted by an 2M HCl (3 mL) to pH=5-6, and the aqueous phase was concentrated in vacuum to obtain 1-[methyl(7H-pyrrolo[2,3-d]pyrimidin-4-yl)amino]pyrrolidyl-3-carboxylic acid (65.00 mg, crude product) which was yellow solid. The value of $C_{12}H_{15}N_5O_2[M+H]^+$ 262 was calculated using MS ESI, and was 262.

Step 8: HOBt (84.04 mg, 621.95 umol), EDCI (119.23 mg, 621.95 umol), 2-glycinonitrile hydrochloride (38.51 mg, 298.54 umol) and triethylamine (151.04 mg, 1.49 mmol) were added in a DMF solution (10 mL) of 1-[methyl(7H-pyrrolo[2,3-d]pyrimidin-4-yl)amino]pyrrolidyl-3-carboxylic acid (65.00 mg, 248.78 umol), and the reaction solution was stirred for 10 h at normal temperature. LCMS showed that the reaction was completed. The mixture was poured into water (10 mL), and an aqueous phase was extracted by dichloromethane:methanol (5/1, 30 mL×4). Merged organic phases were washed by saturated saline solution (15 mL), dried by anhydrous sodium sulfate, and then the organic phases were concentrated. Residues were purified through a preparation type HPLC(NH₃.H₂O) to obtain WX30: N-(cyanomethyl)-1-[methyl(7H-pyrrolo[2,3-d]pyrimidin-4-yl)amino]pyrrolidyl-3-formamide (34.00 mg, yield was 44.93%). ¹H NMR (400 MHz, MeOD-d₄) 8.09 (s, 1H), 7.04 (d, J=3.5 Hz, 1H), 6.90 (br. s., 1H), 4.11-4.27 (m, 2H), 3.00-3.27 (m, 8H), 2.18 (br. s., 2H). The value of $C_{14}H_{17}N_7O[M+H]^+$ 300 was calculated using MS ESI, and was 300.

Embodiment 29

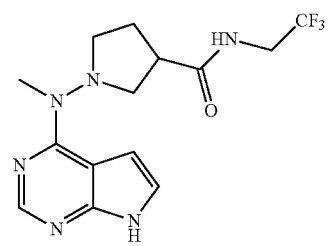

WX31

1-[methyl(7H-pyrrolo[2, 3-d]pyrimidin-4-yl)amino]-N-(2,2,2-trifluoroethyl)pyrrolidyl-3-formamide WX31 was prepared using a preparation method similar to that in Embodiment 28, and a crude product was purified through a preparation type HPLC to obtain WX31 (56.00 mg, yield was 62.47%). ¹H NMR (400 MHz, MeOD-d₄) 8.09 (s, 1H), 7.03 (d, J=3.3 Hz, 1H), 6.91 (br. s., 1H), 3.81-4.04 (m, 2H), 3.03-3.27 (m, 8H), 2.01-2.32 (m, 2H). The value of $C_{14}H_{17}F_3N_6O[M+H]^+$ 343 was calculated using MS ESI, and was 343.

Embodiment 30

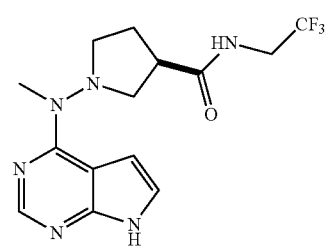

WX32

(R&S)-[methyl(7H-pyrrolo[2,3-d]pyrimidin-4-yl)amino]-N-(2,2,2-trifluoroethyl)pyrrolidyl-3-formamide

WX31

↓ SFC separation

WX32

+

WX33

1-[methyl(7H-pyrrolo[2,3-d]pyrimidin-4-yl)amino]-N-(2,2,2-trifluoroethyl)pyrrolidyl-3-formamide (2.00 g, 5.84 mmol) was separated through a chiral column to obtain WX32: (R or S)-1-[methyl(7H-pyrrolo[2,3-d]pyrimidin-4-yl)amino]-N-(2,2,2-trifluoroethyl) pyrrolidyl-3-formamide (890.00 mg, yield was 44.52%) and WX33: (S or R)-1-[methyl(7H-pyrrolo[2,3-d]pyrimidin-4-yl)amino]-N-(2,2,2-trifluoroethyl)pyrrolidyl-3-formamide (835.00 mg, yield was 41.78%).

SFC separation conditions:
Column: AD (250 mm×30 mm, 5 um) chiral column
mobile phase: A: supercritical $CO_2$, B: 20% MeOH (0.1% $NH_3H_2O$), A:B=80:20
flow rate: 60 mL/min
column temperature: 38° C.
wavelength: 220 nm
jet pressure: 100 Bar
nozzle temperature: 60° C.
evaporating temperature: 20° C.
conditioning temperature: 25° C.

WX32: (R or S)—N-(cyanomethyl)-1-[methyl(7H-pyrrolo[2,3-d]pyrimidin-4-yl)amino]piperidyl-3-formamide, retention time: 5.136 min. $^1$H NMR (400 MHz, MeOD-$d_4$)=8.09 (s, 1H), 7.03 (d, J=3.3 Hz, 1H), 6.76-6.99 (m, 1H), 3.83-4.03 (m, 2H), 3.00-3.27 (m, 8H), 2.19 (br. s., 2H). The value of $C_{14}H_{17}F_3N_6O$ [M+H]$^+$ 343 was calculated using MS ESI, and was 343.

WX33: (S or R)—N-(cyanomethyl)-1-[methyl(7H-pyrrolo[2,3-d]pyrimidin-4-yl)amino]piperidyl-3-formamide, retention time: 5.634 min. $^1$H NMR (400 MHz, MeOD-$d_4$) S=8.09 (s, 1H), 7.03 (d, J=3.3 Hz, 1H), 6.89 (br. s., 1H), 3.85-4.02 (m, 2H), 3.02-3.26 (m, 8H), 2.18 (br. s., 2H). The value of $C_{14}H_{17}F_3N_6O$[M+H]$^+$ 343 was calculated using MS ESI, and was 343.

Embodiment 31

WX34

3-(4-(methyl(7H-pyrrolo[2,3-d]pyrimidin-4-yl)amino)-1,4-diazepan-1-yl)-3-carbonyl-propionitrile 1 →(step 1)

2 →(step 2)

3 →(step 3)

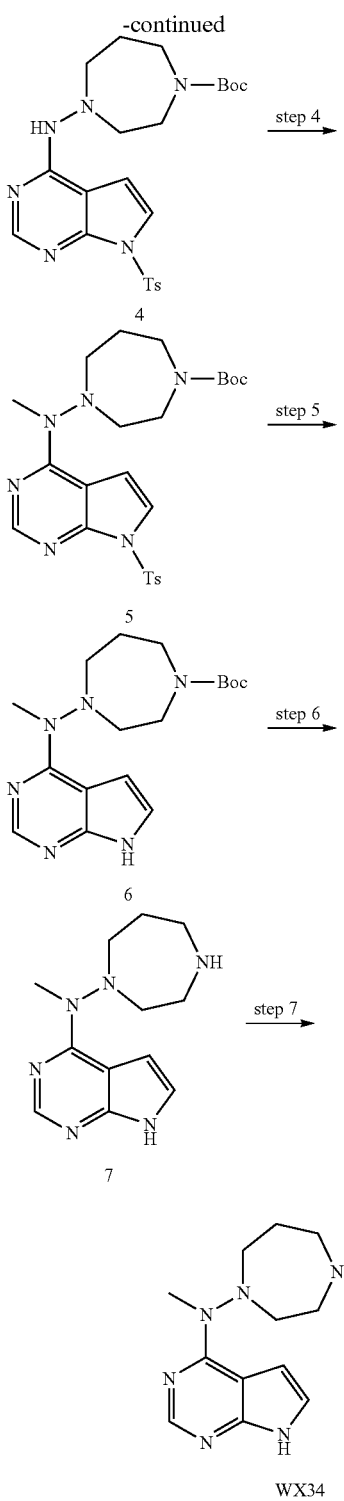

acetate (2*100 ml) was added for extraction. Organic phases were neutralized by solid sodium dicarbonate, washed by water and saline water, dried by anhydrous sodium sulfate, and concentrated under reduced pressure to obtain 4-nitroso-1,4-diazepan-1-carboxylic acid tert-butyl ester (7.00 g, crude product) which was buff oily matter and is directly used in next step. The value of $C_{10}H_{19}N_3O_3[M+H]^+$ 230, was calculated using MS ESI, and was 230.

Step 2: 4-nitroso-1,4-diazepan-1-tert-butyl formate (5.68 g, 24.77 mmol) was dissolved in tetrahydrofuran (100 mL), and lithium aluminum hydride (1.88 g, 49.55 mmol) was added in batched under nitrogen protection at 0° C., and stirred for 30 min at 0° C. Then the mixture was heated to 70° C. and stirred for 2 h. TLC showed that the reaction was completed. The mixture was cooled to 0° C., and added with water (0.88 mL), 15% sodium hydroxide solution (1.88 mL) and water (1.88*3 mL) in sequence. The mixture was stirred for 20 min, filtered and concentrated in vacuum to obtain 4-amino-1,4-diazepan-1-carboxylic acid tert-butyl ester (4.00 g, crude) which was yellow oily matter and directly used in next step. The value of $C_{10}H_{21}N_3O_2[M+H]^+$ 216 was calculated using MS ESI, and was 216.

Step 3: triethylamine (3.76 g, 37.16 mmol) was added into a dioxane solution (100 mL) of 4-amino-1,4-diazepan-1-carboxylic acid tert-butyl ester (4.00 g, 18.58 mmol) and 4-chloro-7-(tosyl)pyrrolo[2,3-d]pyrimidine at 25° C. The mixture was stirred for 5 h at 110° C. LC-MS showed the reaction was completed. The mixture was cooled to 25° C., and was concentrated to be dry under reduced pressure. The residues were purified by a silica gel chromatography (petroleum ether:ethyl acetate=3:1 to 1:1) to obtain 4-[[7-(tosyl)pyrrolo[2,3-d]pyrimidin-4-yl]amino]-1,4-diazepan-1-carboxylic acid tert-butyl ester (1.70 g, yield was 18.80%) which was yellow solid. The value of $C_{23}H_{30}N_6O_4S[M+H]^+$ 487 was calculated using MS ESI, and was 487.

Step 4: 4-[[7-(tosyl)pyrrolo[2,3-d]pyrimidin-4-yl]amino]-1,4-diazepan-1-carboxylic acid tert-butyl ester (800.00 mg, 1.64 mmol, 1.00 Eq) was dissolved in tetrahydrofuran (50 mL) and cooled to 0° C., and sodium hydride (118.37 mg, 4.93 mmol, 3.00 Eq) was added inin batcheses under nitrogen protection. The mixture was stirred for 30 min at 25° C. Then methyl iodide (8.40 g, 59.18 mmol, 36.09 Eq) was dropwise added at 0° C. The mixture was stirred for 2 h at 25° C. TLC showed that the reaction was completed. The mixture was cooled to 0° C., and water was added to quench the mixture. The aqueous phase was extracted using dichloromethane:methanol (10:1, 100 mL×3), M=merged organic phases were washed by saturated saline water (200 mL×2), dried by anhydrous sodium sulfate filtered and concentrated in vacuum to obtain 4-[methyl-[7-(tosyl)pyrrolo[2,3-d]pyrimidine-4-yl]amino]-1,4-diazepan-1-carboxylic acid tert-butyl ester (800.00 mg, 1.60 mmol, yield was 97.44%) which was yellow solid, and is directly used in next reaction without further purification. The value of $C_{24}H_{32}N_6O_4S[M+H]^+$ 501 was calculated using MS ESI, was 501.

Step 5: 4-[methyl-[7-(tosyl)pyrrolo[2,3-d]pyrimidin-4-yl]amino]-1,4-diazepan-1-carboxylic acid tert-butyl ester (400.00 mg, 799.03 umol) was dissolved in tetrahydrofuran (10 mL) and methanol (10 mL), and a water solution (5 mL) of sodium hydroxide (191.77 mg, 4.79 mmol) was added at 25° C. The mixture was stirred for 2 h at 70° C. TLC showed that the reaction was completed. The mixture was cooled to 25° C., and concentrated to be dry under reduced pressure. Residues were extracted using dichloromethane:methanol (10:1, 100 mL×3), merged organic phases were washed by saturated saline water (20 mL×2), dried by anhydrous sodium sulfate, filtered and concentrated under reduced Step 1: 1,4-diazepan-1-carboxylic acid tert-butyl ester (10.00 g, 49.93 mmol) was dissolved in acetic acid (25 mL) and water (15 mL), and cooled to 0° C., then a water solution (10 mL) of sodium nitrite (6.89 g, 99.86 mmol) was dropwise added in 30 min, and the temperature was kept to be lower than 0° C. at the same time. The mixture was warmed up to room temperature naturally and stirred for 1.5 h till TLC showed that the raw materials were completely consumed (petroleum ether:ethyl acetate=3:1, $R_f$=0.45). Ethyl pressure to obtain 4-[methyl(7H-pyrrolo[2,3-d]pyrimidin-4-yl)amino]-1,4-diazepan-1-carboxylic acid tert-butyl ester (270.00 mg, crude product) which was yellow solid and directly used in next reaction without further purification. The value of $C_{17}H_{26}N_6O_2[M+H]^+$ 347 was calculated using MS ESI, and was 347.

Step 6: trifluoroacetic acid (10 mL) was added inin batches to a dichloromethane solution (10 mL) of 4-[methyl (7H-pyrrolo[2,3-d]pyrimidin-4-yl)amino]-1,4-diazepan-1-carboxylic acid tert-butyl ester (270.00 mg, 779.38 umol) at 0° C. The mixture was stirred for 30 min at 25° C. TLC showed that the reaction was completed. The mixture was concentrated under reduced pressure to obtain N-(1,4-azacycloheptan-1-yl)-N-methyl-7H-pyrrolo[2,3-d]pyrimidine-4-amine (180.00 mg, crude product) which was yellow solid and directly used in next reaction without further purification. The value of $C_{12}H_{18}N_6[M+H]^+$ 247 was calculated using MS ESI, was 247.

Step 7: a DMF (3 mL) solution of 2-cyanoacetic acid (43.94 mg, 516.62 umol), HOBt (93.07 mg, 688.82 umol) and EDCI (132.05 mg, 688.82 umol) was stirred for 30 min at 25° C., then a DMF (3 mL) solution of N-(1,4-azacycloheptane-1-yl)-7H-pyrrolo[2,3-d]pyrimidine-4-amine (80.00 mg, 344.41 umol), and triethylamine (174.25 mg, 1.72 mmol) were added. The mixture was stirred for 12 h at 25° C. LC-MS showed the reaction was completed. The mixture was concentrated under reduced pressure, and residues were purified by alkalic preparation type HPLC to obtain WX34 (10.00 mg, yield was 9.70%). $^1$H NMR (400 MHz, METHANOL-d$_4$) δ=8.14 (br. s., 1H), 7.18 (br. s., 1H), 6.83 (br. s., 1H), 3.78-3.70 (m, 2H), 3.69-3.61 (m, 2H), 3.28-3.04 (m, 4H), 2.18 (s, 1H), 2.07 (br. s., 1H), 1.34-1.29 (m, 2H). The value of $C_{15}H_{19}N_7O[M+H]^+$ 314 was calculated using MS ESI, and was 314.

Embodiment 32

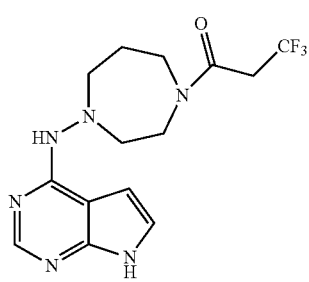

WX35

L-(4-((7H-pyrrolo[2,3-d]pyrimidin-4-yl)amino)-diazepan-1-yl)-3,3,3-trifluorotrifluoropropan-1-one WX35 was prepared using a preparation method similar to that in Embodiment 31, and a crude product was purified through a preparation type HPLC to obtain WX35. $^1$H NMR (400 MHz, METHANOL-d$_4$) δ=8.39-8.35 (m, 1H), 7.29-7.25 (m, 1H), 6.70-6.65 (m, 1H), 5.13 (dd, J=6.7, 13.4 Hz, 1H), 4.78-4.71 (m, 1H), 4.34 (dd, J=4.8, 15.3 Hz, 1H), 4.06-4.01 (m, 1H), 3.90 (s, 3H), 3.88 (s, 1H), 3.84 (d, J=3.8 Hz, 1H), 3.81-3.75 (m, 1H), 3.72-3.66 (m, 1H), 3.60-3.49 (m, 2H), 2.60-2.44 (m, 1H), 2.26-2.15 (m, 1H). The value of $C_{14}H_{17}F_3N_6O[M+H]^+$ 343 was calculated using MS ESI, and was 343.

Embodiment 33

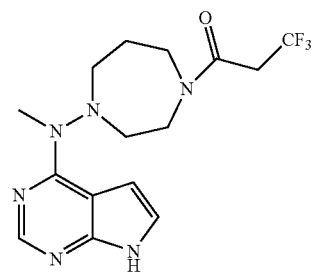

WX36

3,3,3-trifluoro-1-(4-methyl(7H-pyrrolo[2,3-d]pyrimidin-4-yl)amino)-diazepan-1-yl)propan-1-one WX36 was prepared using a preparation method similar to that in Embodiment 31, and a crude product was purified through preparation type HPLC to obtain WX36. $^1$H NMR (400 MHz, METHANOL-d$_4$) δ=8.33-8.29 (m, 1H), 7.44-7.40 (m, 1H), 6.85-6.82 (m, 1H), 4.32-4.14 (m, 1H), 3.85-3.70 (m, 3H), 3.58 (d, J=7.0 Hz, 3H), 3.31-3.25 (m, 1H), 3.16-2.97 (m, 2H), 2.34-2.08 (m, 2H). The value of $C_{15}H_{19}F_3N_6O[M+H]^+$ 357 was calculated using MS ESI, and was 357.

Embodiment 34

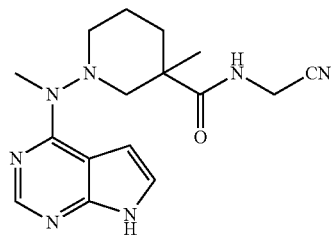

WX37

N-(cyanomethyl)-3-methyl-1-(methyl(7H-pyrrolo[2,3-d]pyrimidin-4-yl)piperidyl-3-formamide

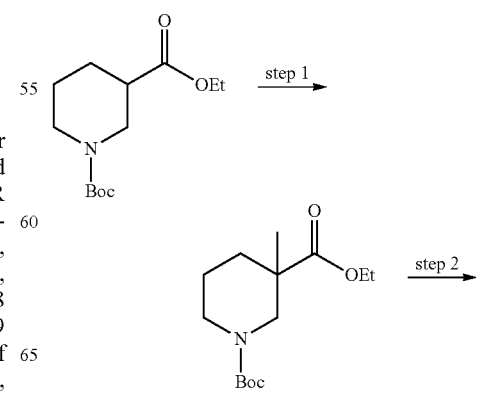

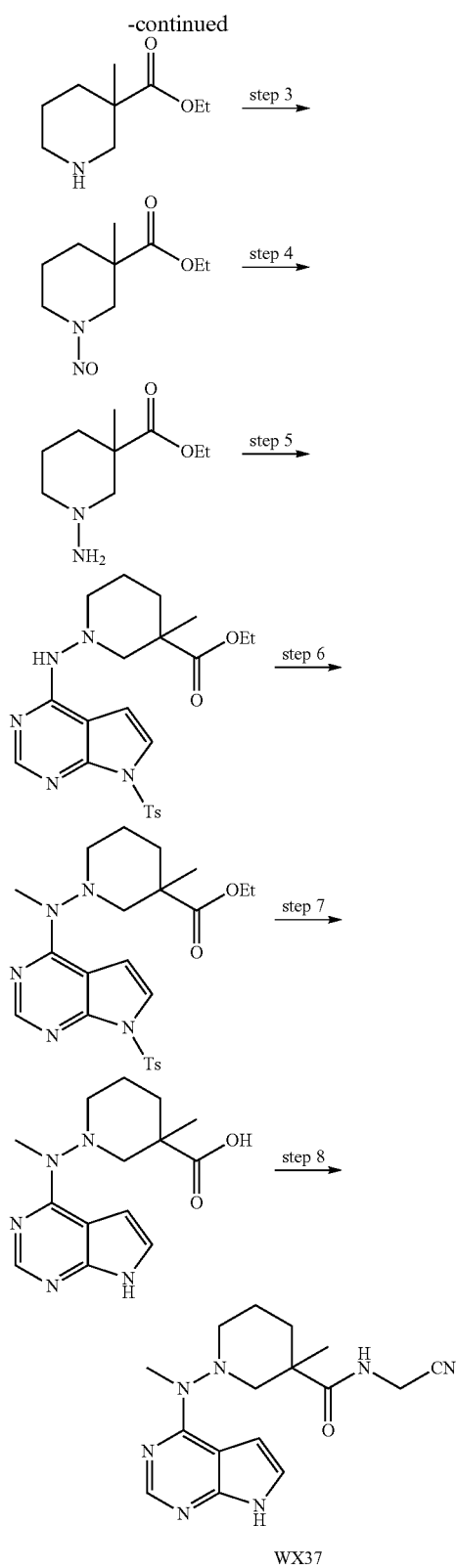

was stirred for 0.5 h at 0° C. A tetrahydrofuran solution (150 mL) oft-butyloxycarbonyl-3-piperidyl carboxylic acid ethyl ester (13.00 g, 50.52 mmol, 1.00 Eq) was dropwise added in the foregoing solution at −78° C. within 30 min; the reactant was stirred for 1.5 h at −78° C. then, and then methyl iodide (31.94 g, 224.81 mmol, 4.45 Eq) was dropwise added. The reaction mixture was stirred for 1 h at the same temperature, and then slowly was warmed up to the room temperature and stirred for 12 h. TLC showed that the reaction was completed. The reaction mixture was quenched by a saturated ammonium chloride (50 mL), and extracted using ethyl acetate (200 mL×2). Merged organic extraction liquid was washed by a saturated ammonium chloride solution (50 mL) and saline water (50 mL), dried and concentrated by sodium sulfate to obtain a crude compound 1-t-butyloxycarbonyl-3-methyl-3-piperidyl carboxylic acid ethyl ester (15 g, crude product) which was directly used in next reaction without further purification. The value of $C_{14}H_{25}NO_4[M+H]^+$ 272, was calculated using MS ESI, and was 272.

Step 2: trifluoroacetic acid (25 mL) was added in batches to a dichloromethane solution of 1-t-butyloxycarbonyl-3-methyl-3-piperidyl carboxylic acid ethyl ester ((13.70 g, 50.49 mmol, 1.00 Eq) at 0° C. The mixture was stirred for 30 min at 25° C. TLC showed that the reaction was completed. The mixture was concentrated under reduced pressure to obtain ethyl-3-methylpiperidyl-3-carboxylate (9 g, crude product) which was yellow oily matter and was directly used in next reaction without further purification. The value of $C_9H_{17}NO_2[M+H]^+$ 172 was calculated using MS ESI, and was 172.

Step 3: ethyl 3-methylpiperidyl-3-carboxylate (8.60 g, 50.22 mmol, 1.00 Eq) was dissolved in acetic acid (30 mL) and water (30 mL), and an aqueous solution (30 mL) of sodium nitrite (6.93 g, 100.44 mmol, 2.00 Eq) was dropwise added at 0° C. The aqueous solution was dropwise added in 10 min. During this period, the temperature was maintained to be lower than 0° C. The reaction mixture was warmed up to the room temperature (25° C.) and stirred for 3 h at 25° C. TLC (petroleum ether:ethyl acetate=1:1) showed that the raw materials were completely consumed. Ice was slowly added in the reaction solution to quench, and then ethyl acetate (100 mL×3) was used for extraction. Merged organic phases were diluted by water (100 mL), neutralized by sodium carbonate, washed by water (100 mL×2) and saturated saline solution (20 mL×2), dried by anhydrous sodium sulfate, filtered and concentrated in vacuum. Residues were purified by a silica gel column chromatography (100-200 mesh silica gel, petroleum ether:ethyl acetate=5:1-3:1) to obtain ethyl 3-methyl-1-nitroso-piperidyl-3-carboxylate (3.10 g, 15.48 mmol, yield was 30.83%) which was yellow oily matter. The value of $C_9H_{16}N_2O_3[M+H]^+$ 201 was calculated using MS ESI, and was 201.

Step 4: zinc (5.06 g, 77.41 mmol, 5.00 Eq) was added into a methanol solution (50 mL) of ethyl 3-methyl-1-nitroso-piperidyl-3-carboxylate (3.10 g, 15.48 mmol, 1.00 Eq) at 0° C. The mixture was stirred for 5 min at 0° C. Then acetic acid (15 mL) was dropwise added, and the temperature was kept to be lower than 0° C. at the same time. After the acetic acid was added, the mixture was stirred for 3 h at 25° C. TLC showed that the reaction was completed. The mixture was filtered, and the filtrate was diluted by water (100 mL) and dichloromethane (100 mL), cooled to 0° C., and alkalized by solid sodium carbonate to pH=8-9; then organic phases were separated and the aqueous phase was extracted by dichloromethane:methanol (10:1, 100 mL×3); merged organic phases were washed by saturated saline solution (100 mL), dried by anhydrous sodium sulfate, filtered and concentrated Step 1: tetrahydrofuran (150 mL) was added in a flame-drying round flask under argon atmosphere, and was cooled to −78C then, and added with diisopropylamine (6.13 g, 60.62 mmol, 1.20 Eq), and then n-butyllithium (2.5 M, 24.25 mL, 1.20 Eq) was dropwise added in 30 min. The mixture in vacuum to obtain obtain ethyl 1-amino-3-methyl-piperidyl-3-carboxylate (2.80 g, yield was 97.12%) which was buff oily matter. The value of $C_9H_{18}N_2O_2[M+H]^+$ 187 was calculated using MS ESI, and was 187.

Step 5: ethyl 1-amino-3-methylpiperidyl-3-carboxylate (2.80 g, 15.03 mmol, 1.00 Eq) and 4-chloro-7-(tosyl)pyrrolo[2,3-d]pyrimidine (4.86 g, 15.79 mmol, 1.05 Eq) were dissolved in dioxane (30 mL) and added with triethylamine (2.28 g, 22.55 mmol, 1.50 Eq). The mixture was stirred for 5 h at 110° C. TLC showed that the reaction was completed. The mixture was cooled to 25° C. The mixture was diluted by water (20 mL), the aqueous phase was extracted using ethyl acetate (100 mL×2), organic phases were merged and were successively washed by water (30 mL×2) and saturated saline water (20 mL), dried by anhydrous sodium sulfate, filtered and concentrated in vacuum. The residues were purified by a silica gel chromatography (petroleum ether: ethyl acetate=5:1 to 1:1) to obtain ethyl 3-methyl-1-[[7-(tosyl)pyrrolo[2,3-d]pyrimidin-4-yl)amino]piperidyl-3-carboxylate (1.10 g, 2.40 mmol, yield was 15.96%) which was yellow solid. The value of $C_{22}H_{27}N_5O_4S[M+H]^+$ 458 was calculated using MS ESI, and was 458.

Step 6: sodium hydride (124.80 mg, 3.12 mmol, 1.30 Eq) was added in batches to tetrahydrofuran solution (30 mL) of 3-methyl-1-[[7-(tosyl)pyrrolo[2,3-d]pyrimidin-4-yl)amino] piperidyl-3-carboxylate (1.10 g, 2.40 mmol, 1.00 Eq) under nitrogen portion at 0° C. The mixture was stirred for 30 min at 25° C., then cooled to 0° C. again, and methyl iodide (511.87 mg, 3.61 mmol, 1.50 Eq) was added. The mixture was stirred for 2.5 h at 25° C. TLC showed that the reaction was completed. Water (10 mL) was added to quench the reaction solution. The aqueous phase was extracted using ethyl acetate (50 mL×2), merged organic phases were washed by saturated saline solution (20 mL), dried by anhydrous sodium sulfate, filtered, and concentrated under reduced pressure. The residues were purified by a silica gel chromatography (100-200 mesh silica gel, petroleum ether: ethyl acetate=3:1 to 1:1) to obtain 3-methyl-1-[methyl-[7-(tosyl)pyrrolo[2,3-d]pyrimidine-4-yl)amino]piperidyl-3-carboxylic acid methyl ester (1.00 g, 2.12 mmol, wherein the yield was 88.36%) which was yellow solid. The value of $C_{23}H_{29}N_5O_4S[M+H]^+$ 472 was calculated using MS ESI, and was 472.

Step 7: 3-methyl-1-[methyl-[7-(tosyl)pyrrolo[2,3-d]pyrimidin-4-yl]amino]piperidyl-3-carboxylic acid ethyl ester (1.00 g, 2.12 mmol, 1.00 Eq) was dissolved in tetrahydrofuran (10 mL) and methanol (10 mL) at 25° C., and a water solution (5 mL) of sodium hydroxide (848.00 mg, 21.20 mmol, 10.00 Eq) was added. Then the mixture was heated to 100° C. and stirred for 5 h. TLC showed that the reaction was completed. The mixture was cooled to 25° C., and concentrated under reduced pressure. Residues were acidized by diluted HCl (aqueous solution) to pH=5-6, and then concentrated under reduced pressure to obtain 3-methyl-1-[methyl(7H-pyrrolo[2,3-d]pyrimidin-4-yl)yl-amino]piperidyl-3-carboxylic acid (600.00 mg, crude product) which was yellow solid and directly used in next reaction without further purification. The value of $C_{14}H_{19}N_5O_2[M+H]^+$ 290 was calculated using MS ESI, and was 290.

Step 8: 3-methyl-1-[methyl(7H-pyrrolo[2,3-d]pyrimidin-4-yl)yl-amino]piperidyl-3-carboxylic acid (300.00 mg, 1.04 mmol, 1.00 Eq), HOBt (281.05 mg, 2.08 mmol, 2.00 Eq) and EDCI (398.74 mg, 2.08 mmol, 2.00 Eq) were dissolved in DMF (4 mL), and stirred for 30 min at 25° C., then 2-aminoacetonitrile (192.46 mg, 2.08 mmol, 2.00 Eq) and triethylamine (420.95 mg, 4.16 mmol, 4.00 Eq) were added in sequence. The mixture was stirred for 12 h at 25° C. LC-MS showed the reaction was completed. The mixture was diluted by water (5 mL) and extracted by ethyl acetate (100 mL×3). Merged organic phases were washed by saturated saline water (20 mL×2), dried by anhydrous sodium sulfate, and filtered, and the solvent was concentrated under reduced pressure. Residues were purified using an alkalic preparation type HPLC to obtain WX37: N-(cyanomethyl)-3-methyl-1-[methyl(7H-pyrrolo[2,3-d]pyrimidie-yl)amino] piperidyl-3-formamide (130.00 mg, 397.09 umol, yield was 38.18%). The value of $C_{16}H_{21}N_7O[M+H]^+$ 328 was calculated using MS ESI, and was measured to be 328. $^1$H NMR (400 MHz, METHANOL-d$_4$) δ=8.18 (br. s., 1H), 7.11 (d, J=3.3 Hz, 1H), 6.71 (d, J=2.8 Hz, 1H), 4.25 (d, J=17.3 Hz, 1H), 3.93 (br. s., 1H), 3.29 (br. s., 3H), 2.99-2.80 (m, 4H), 2.24 (d, J=11.5 Hz, 1H), 2.03 (s, 1H), 1.75 (d, J=12.3 Hz, 1H), 1.19 (s, 4H). The value of $C_{16}H_{21}N_7O[M+H]^+$ 328 was calculated using MS ESI, and was 328.

Embodiment 35

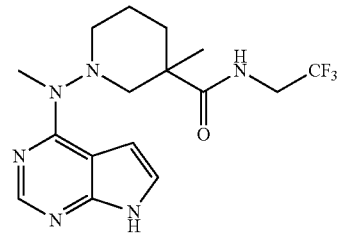

WX38

3-methyl-11-(methyl(7H-pyrrolo[2,3-d]pyrimidine-4-yl)amino)-N-(2,2,2-trifluoroethyl)piperidyl-3-formamide WX38 was prepared using a preparation method similar to that in Embodiment 34 and a crude product was purified through a preparation type HPLC to obtain WX38. $^1$H NMR (400 MHz, METHANOL-d$_4$) δ=8.15 (s, 1H), 7.08 (d, J=3.3 Hz, 1H), 6.73 (br. s., 1H), 4.25-4.12 (m, 1H), 3.50 (br. s., 1H), 3.30 (s, 3H), 2.97-2.80 (m, 4H), 2.23 (d, J=12.5 Hz, 1H), 2.12-1.98 (m, 1H), 1.74 (d, J=13.1 Hz, 1H), 1.19 (br. s., 4H). The value of $C_{16}H_{21}F_3N_6O[M+H]^+$ 371 was calculated using MS ESI, and was 371.

Embodiment 36

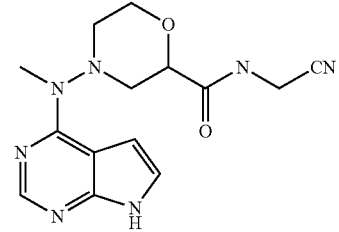

WX39

N-(cyanoethyl)-4-(methyl(7H-pyrrolo[2,3-d]pyrimidin-4-yl)amino)morpholine-2-formamide

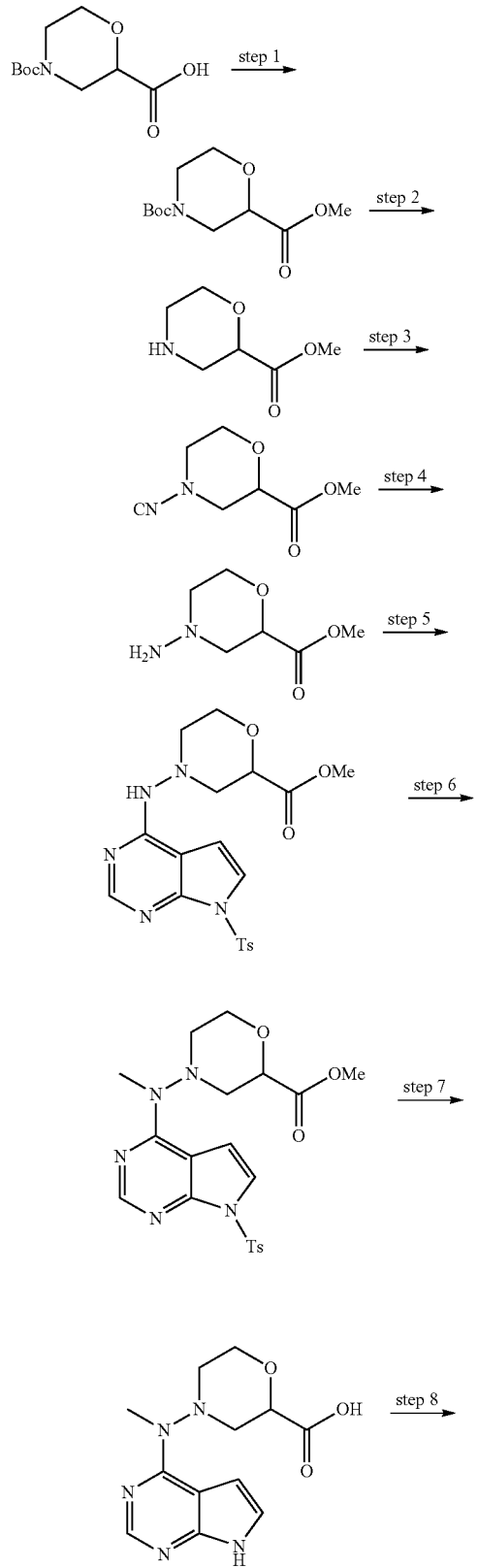

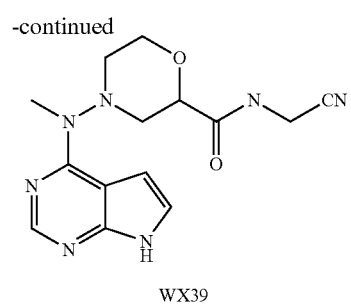

WX39

Step 1: 4-(t-butyloxycarboryl)morpholine-2-carboxylic acid (7.30 g, 31.57 mmol) was dissolved in a mixed solvent of dichloromethane (150.00 mL) and methanol (10.00 mL), and then a hexane solution of $TMSCHN_2$ (2 M, 23.68 hydrochloric acid) was dropwise added under nitrogen protection at 0° C. The reaction mixture was stirred for 0.5 h at 25° C. TLC (petroleum ether:ethyl acetate=1:1) showed that the raw materials were completely reacted. A saturated ammonium chloride solution (20 mL) was added for quenching, then dichloromethane was used for extraction (100 mL×2), merged organic phases were washed by saturated saline water (20 mL), dried by anhydrous sodium sulfate, filtered and concentrated under reduced pressure to obtain 4-(t-butyloxycarboryl)morpholine-2-carboxylic acid methyl ester (8.00 g, crude product) which was buff solid and directly used in next reaction without further purification. dichloromethane. The value of $C_{11}H_{19}NO_5[M+H]^+$ 246 was calculated using MS ESI, and was 246.

Step 2: a dioxane solution (4 M, 32.62 mL) of hydrochloric acid was dropwise added to a dichloromethane solution (100.00 mL) of 4-(t-butyloxycarboryl)morpholine-2-carboxylic acid methyl ester (8.00 g, 32.62 mmol) at 0° C. The reaction mixture was stirred for 0.5 h at 25° C. TLC (petroleum ether:ethyl acetate=3:1) showed that the raw materials were completely consumed. The reaction solution was concentrated under reduced pressure to obtain morpholine-2-carboxylic acid methyl ester (6.00, crude product) which was white solid and directly used in next reaction without further purification. The value of $C_6H_{11}NO_3[M+H]^+$ 146 was calculated using MS ESI, and was 146.

Step 3: morpholine-2-carboxylic acid methyl ester (5.70 g, 31.38 mmol) was dissolved in acetic acid (50.00 mL) and water (50.00 mL), and an aqueous solution (50.00 mL) of sodium nitrite (4.33 62.77 mmol) was dropwise added in the foregoing solution at 0° C. The mixture was stirred for 30 min at 0° C. and then stirred for 2 h at 25° C. TLC showed that the reaction was completed. Water (30 mL) was added to quench the reaction. The aqueous phase was extracted using ethyl acetate (100 mL×2). Merged organic phases were washed by saturated saline water (20 mL×2), dried by anhydrous sodium sulfate, filtered, and concentrated in vacuum at 70° C. so as to remove partial acetic acid. Residues were dissolved in a mixed solution of ethyl acetate (100 mL) and water (50 mL), and alkalized by solid sodium hydrogen carbonate to pH=8-9. The mixture was extracted using ethyl acetate (100 mL×2), merged organic phases were washed by saturated saline water (20 mL×2), dried by anhydrous sodium sulfate, filtered and concentrated under reduced pressure to obtain 4-nitroso-morpholine-2-carboxylic acid methyl ester (5.40 g, yield was 97.83%) which was buff solid. The value of $C_6H_{10}N_2O_4[M+H]^+$ 175 was calculated using MS ESI, and was 175.

Step 4: 4-nitroso-morpholine-2-carboxylic acid methyl ester (4.40 g, 25.27 mmol) was dissolved in methanol (50.00 mL) and cooled to −10° C., then zinc (8.26 g, 126.33 mmol) was added in the solution under nitrogen protection, and acetic acid (15.17 g, 252.66 mmol) was dropwise added at −10° C. to 0° C. The mixture was stirred for 60 min at 0° C. and then stirred for 4 h at 25° C. TLC showed that the reaction was completed. The mixture was filtered and washed by methanol (1000 mL). The filtrate was concentrated under reduced pressure at 70° C. Residues were resolved in dichloromethane:methanol (10:1, 400 mL) and alkalized to pH=8-9. The mixture was filtered by diatomite and washed by dichloromethane:methanol (10:1). The filtrate was concentrated under reduced pressure to obtain 4-aminomorpholine-2-carboxylic acid methyl ester (5.30 g, crude product) which was yellow oily matter and was directly used in next reaction without further purification. The value of $C_6H_{12}N_2O_3[M+H]^+$ 161 was calculated using MS ESI, and was 161.

Step 5: 4-aminomorpholine-2-carboxylic acid methyl ester (4.30 g, 26.85 mmol) and 4-chloro-7-(tosyl)pyrrolo[2,3-d]pyrimidine (8.26 g, 26.85 mmol) were dissolved in dioxane (100.00 mL), and triethylamine (8.15 g, 80.55 mmol) was added under nitrogen protection. The foregoing mixture was stirred for 24 h at 110° C. TLC show there was no much more progress in the reaction. The mixture was cooled to 25° C., and then concentrated under reduced pressure at 50° C. Residues were diluted by water (50 mL), the aqueous phase was extracted by ethyl acetate (100 mL×3), merged organic phases were washed by saturated saline water (20 mL×2), dried by anhydrous sodium sulfate, filtered and concentrated under reduced pressure. The residues were purified by a silica gel column chromatography (100-200 mesh silica gel, petroleum ether:ethyl acetate:dichloromethane=5:1:0.5 to 1:1:1) to obtain 4-[[7-(tosyl)pyrrolo[2,3-d]pyrimidin-4-yl]amino]morpholine-2-carboxylic acid methyl ester (3.80 g, 7.93 mmol, yield was 29.52%) which was yellow solid. The value of $C_{19}H_{21}N_5O_5S[M+H]^+$ 432, was calculated using MS ESI, and was 432.

Step 6: 4-[[7-(tosyl)pyrrolo[2,3-d]pyrimidin-4-yl]amino]morpholine-2-carboxylic acid methyl ester (3.80 g, 8.81 mmol) was dissolved in tetrahydrofuran (100.00 mL), and sodium hydride (422.80 mg, 10.57 mmol, 1.20 eq) was added in batches under nitrogen protection at 0° C. The reaction solution was stirred for 60 min at 0° C., then dropwise added with methyl iodide (7.17 g, 50.48 mmol) at 0° C., and continuously stirred for 4 h at 25° C. TLC showed that the reaction was completed. The mixture was cooled to 0° C., and water (20 mL) was added to quench. The aqueous phase was extracted using ethyl acetate (100 mL×2), merged organic phases were washed by saturated saline solution (20 mL), dried by anhydrous sodium sulfate, filtered, and concentrated under reduced pressure. The residues were purified by a silica gel column chromatography (100-200 mesh silica gel, petroleum ether:ethyl acetate=3:1 to 1:1) to obtain 4-[methyl-[7-(tosyl)pyrrolo[2,3-d]pyrimidin-4-yl]amino]morpholine-2-carboxylic acid methyl ester (140.00 mg, yield was 3.39%) which was yellow solid. The value of $C_{20}H_{23}N_5O_5S[M+H]^+$ 446 was calculated using MS ESI, and was 446.

Step 7: an aqueous solution (2.50 mL) of sodium hydroxide (50.28 mg, 1.26 mmol) was added in a mixed solution of tetrahydrofuran (5.00 mL) and methanol (5.00 mL) of 4-[methyl-[7-(tosyl)pyrrolo[2,3-d]pyrimidin-4-yl]amino]morpholine-2-carboxylic acid methyl ester (140.00 mg, 314.26 umol). The mixture was stirred for 2 h at 100° C. LC-MS showed the reaction was completed. The mixture was cooled to 25° C., and then concentrated under reduced pressure at 50° C. Residues were neutralized by an aqueous solution of diluted hydrochloric acid and concentrated under reduced pressure to obtain 4-[methyl(7H-pyrrolo[2,3-d]pyrimidin-4-yl)amino]morpholine-2-formic acid (120 mg, crude product) which was yellow solid and directly used in next reaction without further purification. The value of $C_{12}H_{15}N_5O_3[M+H]^+$ 278 was calculated using MS ESI, and was 278.

Step 8: 4-[methyl(7H-pyrrolo[2,3-d]pyrimidin-4-yl)amino]morpholine-2-formic acid (45.00 mg, 162.29 umol), HOBt (43.86 mg, 324.58 umol) and EDCI (62.22 mg, 324.58 umol) were dissolved in DMF (4.00 mL). The mixture was stirred for 30 min at 25° C., then added with 2-aminoacetonitrile (30.03 mg, 324.58 umol) and triethylamine (65.69 mg, 649.16 umol), and then the mixture was stirred for 12 h at 25° C. LC-MS showed the reaction was completed. The mixture was diluted by water (5 mL). The aqueous phase was extracted by dichloromethane:methanol (5:1, 20 mL×3), merged organic phases were washed by saturated saline solution (20 mL), dried by anhydrous sodium sulfate, filtered and concentrated under reduced pressure. Residues were purified by a alkalic type HPLC to obtain WX39 (20.00 mg, yield was 39.08%). $^1$H NMR (400 MHz, METHANOL-$d_4$) δ=8.16 (s, 1H), 7.15-7.06 (m, 2H), 4.63 (br. s., 1H), 4.47 (dd, J=2.8, 10.0 Hz, 1H), 4.24-4.13 (m, 3H), 4.05 (t, J=10.5 Hz, 1H), 3.29-3.18 (m, 5H), 3.00-2.84 (m, 2H). The value of $C_{14}H_{17}N_7O_2[M+H]^+$ 316 was calculated using MS ESI, and was 316.

Embodiment 37

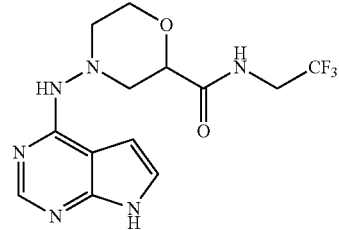

WX40

4-((7H-pyrrolo[2,3-d]pyrimidin-4-yl)amino)-N-(2,2,2-trifluoroethyl)morpholine-2-form amide WX40 was prepared using a preparation method similar to that in Embodiment 36, and a crude product was purified through a preparation type HPLC to obtain WX40. $^1$H NMR (400 MHz, METHANOL-$d_4$) δ=8.13 (s, 1H), 7.14 (d, J=3.3 Hz, 1H), 6.86 (br. s., 1H), 4.63 (s, 1H), 4.39 (dd, J=2.4, 10.4 Hz, 1H), 4.12 (d, J=11.5 Hz, 1H), 4.02-3.88 (m, 3H), 3.41 (d, J=7.8 Hz, 1H), 3.07 (d, J=10.8 Hz, 1H), 2.92-2.82 (m, 1H), 2.66 (d, J=16.1 Hz, 1H). The value of $C_{13}H_{15}F_3N_6O_2[M+H]^+$ 345 was calculated using MS ESI, and was 345.

Embodiment 38

WX41

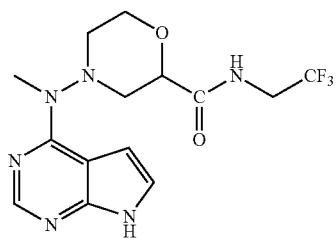

4-(methyl(7H-pyrrolo[2,3-d]pyrimidin-4-yl)amino)-
N-(2,2,2-trifluoroethyl)morpholine-2-formamide WX41 was prepared using a preparation method similar to that in Embodiment 36, and a crude product was purified through a preparation type HPLC to obtain WX41. $^1$H NMR (400 MHz, METHANOL-$d_4$) δ=8.16 (s, 1H), 7.11 (br. s., 2H), 4.63 (br. s., 1H), 4.47 (dd, J=2.8, 10.0 Hz, 1H), 4.21-4.14 (m, 1H), 4.05 (t, J=10.4 Hz, 1H), 3.94 (d, J=9.3 Hz, 2H), 3.26-3.15 (m, 5H), 2.99-2.84 (m, 2H). The value of $C_{14}H_{17}F_3N_6O_2[M+H]^+$ 359 was calculated using MS ESI, and was 359.

Embodiment 39

WX42

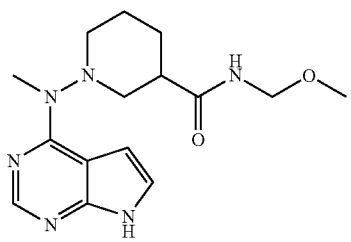

N-(methoxymethyl)-1-[methyl-(7H-pyrrole[2,3-d]pyrimidin-4-]amino] piperidyl-3-formamide

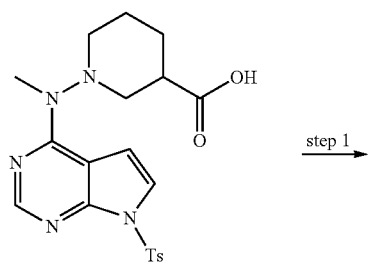

Intermediate 3

→ step 1

-continued

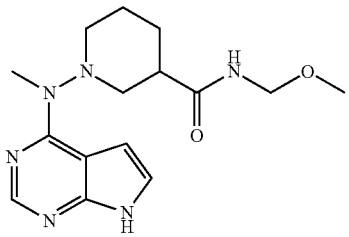

2

→ step 2

3

→ step 3

5

→ step 4

WX42

Step 1: 1-[methyl-[7-(tosyl)pyrrole[2,3-d]pyrimidine-4-]amino]piperidyl-3-formic acid (672.75 mg, 1.57 mmol) was dissolved in tetrahydrofuran (30.00 mL), and added with triethylamine (474.98 mg, 4.69 mmol) and isopropyl chloroformate (191.75 mg, 1.56 mmol) under nitrogen protection, then the mixture was stirred to react for 2 h. TLC showed that the raw materials were completely reacted and an intermediate was obtained. $NH_3 \cdot H_2O$ (548.41 mg, 15.65 mmol) was added and continuously stirred to react for 12 h. TLC showed that the raw materials were completely reacted. Water (10 ml) and ethyl acetate (10 mL×3) were added for extraction. Organic layers were merged, washed by saturated saline solution (10 mL×1), dried by anhydrous sodium sulfate, filtered and reduced pressure distillation to remove solvent, obtain grey solid, further purified by prepare TLC (DCM:MeOH=20:1) to obtain 1-[methyl-[7-(tosyl)pyrrole [2,3-d]pyrimidine-4-]amino]piperidyl)-3-formamide (590.00 mg, 76.92%). The value of $C_{20}H_{24}N_6O_3S[M+H]^+$ 429.16 was calculated using MS ESI, and was 429.

Step 2: 1-[methyl-[7-(tosyl)pyrrole[2,3-d]pyrimidine-4-]amino]piperidyl)-3-formamide (195.00 mg, 456.12 umol) was dissolved in DMF (2 mL), added with $K_2CO_3$ (157.60 mg, 1.14 mmol), KI (37.86 mg, 228.06 umol), and chloromethyl methyl sulfide (65 mg, 684 umol) in sequence, heated to 80° C. and stirred for 12 h. TLC showed that the raw materials were completely reacted. Water (15 ml) and ethyl acetate (10 mL×3) were added for extraction. Organic layers were merged, washed by saturated saline solution (10 mL×1), dried by anhydrous sodium sulfate, filtered and reduced pressure distillation to remove solvent, to obtain grey solid and separate the solid by preparation TLC (petroleum ether:ethyl acetate=1:1) to obtain 1-[methyl-[7-(tosyl)pyrrole[2,3-d]pyrimidine-4-]amino]-N-[(methylmercapto)methyl]piperidyl-3-formamide (75.00 mg, 33.72%). The value of $C_{22}H_{28}N_6O_3S_2[M+H]^+$ 489.17 was calculated using MS ESI, and was 489.

Step 3: 1-[methyl-[7-(tosyl)pyrrole[2,3-d]pyrimidine-4-]amino]-N-[(methylmercapto)methyl]piperidyl-3-formamide (121.00 mg, 248.13 umol) was resolved in dichloromethane DCM (10.00 mL), and added with m-CPBA (100.75 mg, 496.27 umol, 2.00 eq) in batches, and then stirred to react for 12 h at 25° C. TLC showed that the raw materials were completely reacted, and LC-MS showed that product was generated. Saturated sodium thiosulfate (5 mL×3) was added to quench residual m-CPBA, and dichloromethane (10 mL×3) was used for extraction, then organic layers were merged, washed by saturated saline solution (10 mL×1), dried by anhydrous sodium sulfate, filtered and reduced pressure distillation to remove solvent, obtain grey solid and separate through a preparation TLC (DCM:MeOH=10:1) to obtain faint yellow viscous material 1-[methyl-[7-(tosyl)pyrrole[2,3-d]pyrimidine-4-]amino]-N-[(methylsulphonyl)methyl]piperidyl-3-formamide (88.00 mg, 68.25%). The viscous material was dissolved in methanol and heated to obtain N-(methoxymethyl)₁-[methyl-[7-(tosyl)pyrrole[2,3-d]pyrimidine-4-]amino]piperidyl)-3-formamide. The solvent was removed and the product was directly used in next reaction without further purification. The value of $C_{22}H_{28}N_6O_4S$ $[M+H]^+$ 473.19 was calculated using MS ESI, and was 473.

Step 4: N-(methoxymethyl) 1-[methyl-[7-(tosyl)pyrrole[2,3-d]pyrimidine-4-]amino]piperidyl)-3-formamide (80.00 mg, 169.29 umol) was dissolved in methanol (2.00 mL), added with NaOH (1 M, 508 uL), and stirred to react for 24 h at 25° C. TLC showed that the raw materials completely reacted, and LC-MS showed that there was a product generated. Water (10 ml) was added, the mixture was filtered and the product was washed by a mixed solvent (DCM:MeOH=5:1), and concentrated to obtain white solid, and a preparation HPLC (alkalic method) was used to obtain WX42: N-(methoxymethyl) 1-[methyl-(7H-pyrrole[2,3-d]pyrimidine-4-]amino]piperidyl)-3-formamide (13.40 mg, 24.86%). The value of $C_{15}H_{22}N_6O_2[M+H]^+$ 319.18 was calculated using MS ESI, and was 319. $^1$H NMR (400 MHz, METHANOL-$d_4$) δ=8.13 (s, 1H), 7.08 (s, 2H), 4.53-4.61 (m, 2H), 3.28 (s, 3H), 3.23 (s, 3H), 2.99-3.09 (m, 2H), 2.74-2.98 (m, 3H), 1.83-2.06 (m, 3H), 1.40-1.61 (m, 1H).

Embodiment 40

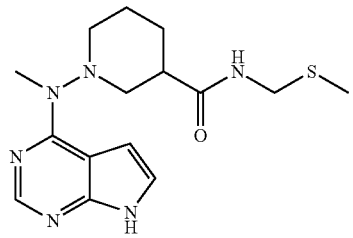

WX43

1-[methyl-[7H-pyrrole[2,3-d]pyrimidine-4-]amino]-N-(methylthiomethyl)piperidyl-3-formamide Step 1: 1-[methyl-[7-(tosyl)pyrrole[2,3-d]pyrimidine-4-]amino]-N-[(methylmercapto)methyl]piperidyl-3-formamide was dissolved in a mixed solvent of (MeOH (5.00 mL) and H2O (2.00 mL), added with NaOH (16.95 mg, 423.63 umol), and were stirred to react for 12 h at 25° C. TLC showed that the raw materials were completely reacted. LC-MS showed that there was a product generated. HCl (1 M*10 ml) was added to adjust to pH=7-8, then the mixture was concentrated to 5 mL, and separated by a preparation HPLC (alkalic method) to obtain WX43: 1-[methyl-[7H-pyrrole[2,3-d]pyrimidine-4-amino]-N-(methylthiomethyl)piperidyl-3-formamide (9.30 mg, 9.85%). The value of $C_{18}H_{22}N_6OS[M+H]^+$ 334.16 was calculated using MS ESI, and was 335. $^1$HNMR (400 MHz, METHANOL-$d_4$)=8.12 (s, 1H), 7.08 (s, 2H), 4.33-4.17 (m, 2H), 3.23 (s, 3H), 3.08-2.79 (m, 5H), 2.12 (s, 3H), 2.01-1.86 (m, 3H), 1.50 (d, J=10.0 Hz, 1H).

Embodiment 41

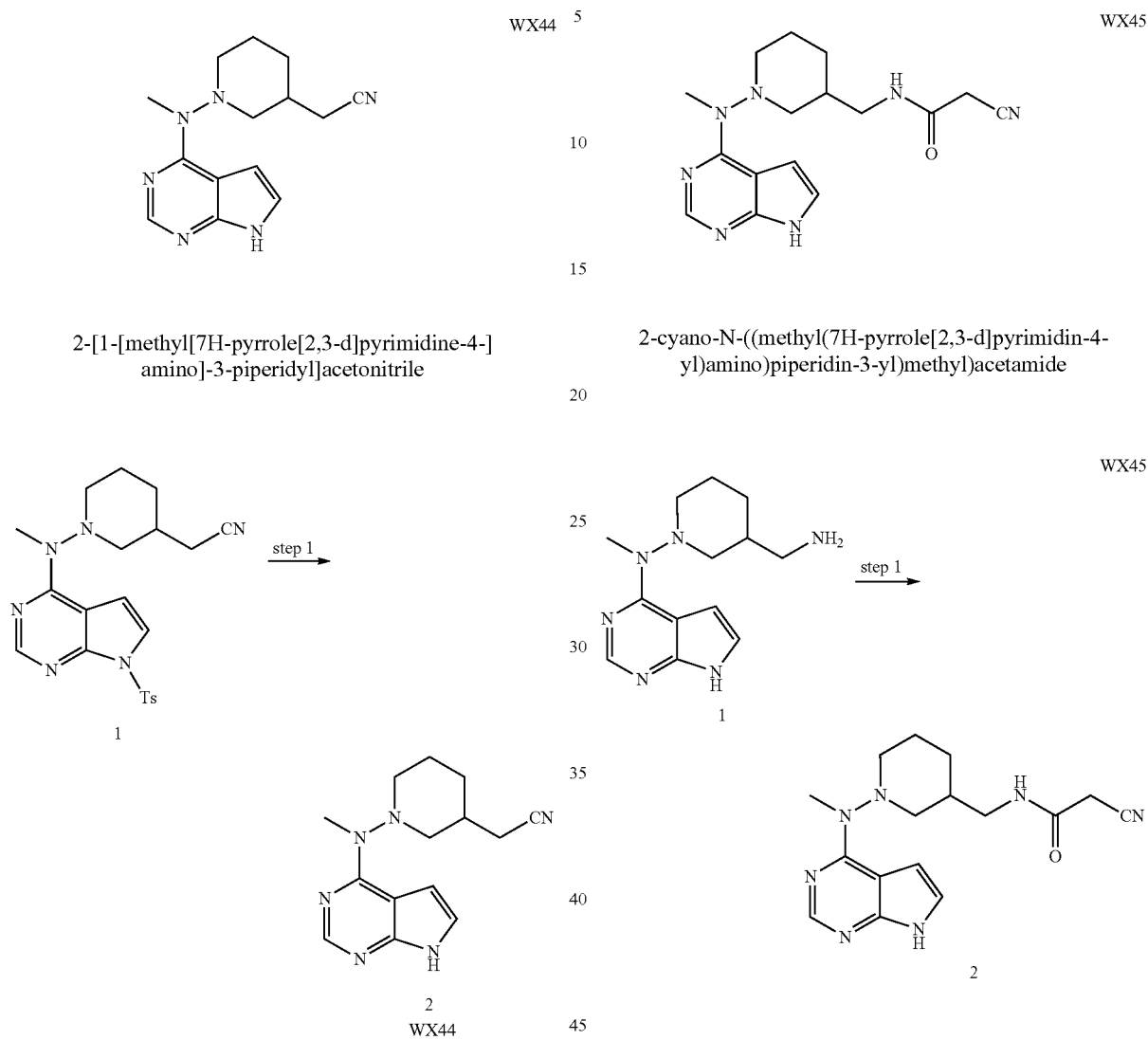

2-[1-[methyl[7H-pyrrole[2,3-d]pyrimidine-4-]amino]-3-piperidyl]acetonitrile

Embodiment 42

2-cyano-N-((methyl(7H-pyrrole[2,3-d]pyrimidin-4-yl)amino)piperidin-3-yl)methyl)acetamide Step 1: 2-[1-[methyl[7-(tosyl)pyrrole[2,3-d]pyrimidine-4-]amino]-3-piperidyl]acetonitrile was dissolved in a mixed solvent of THF (90.00 uL)/H$_2$O (180.00 uL)/MeOH (180.00 uL), added with NaOH (26.91 mg, 672.75 umol), and stirred to react for 12 h at 25° C. LC-MS showed that the reaction was completed. Stirring was stopped, and the mixture was concentrated under reduced pressure to remove organic solvent, adjusted by HCl (1 M×5 mL) to pH=7-8, and separated by a preparation HPLC (alkalic method) to obtain WX44: 2-[1-[methyl[7H-pyrrole[2,3-d]pyrimidine-4-]amino]-3-piperidyl]acetonitrile (30.00 mg, 48.55%). The value of C14H18N6[M+H]$^+$ 271.16 was calculated using MS ESI, and was 271. $^1$H NMR (400 MHz, METHANOL-d$_4$) δ=8.16-8.10 (m, 1H), 7.08 (d, J=3.3 Hz, 1H), 7.03 (d, J=3.3 Hz, 1H), 3.21 (s, 3H), 3.03 (d, J=7.3 Hz, 1H), 2.97-2.79 (m, 2H), 2.67 (t, J=10.5 Hz, 1H), 2.53-2.41 (m, 2H), 2.33-2.19 (m, 1H), 2.04-1.81 (m, 3H), 1.21-1.00 (m, 1H).

Step 1: 2-cyanoacetic acid (158.14 mg, 1.86 mmol) was dissolved in DMF (4 mL), added with HOBt (502.41 mg, 3.72 mmol) and EDCI (712.78 mg, 3.72 mmol), and stirred to react for 30 min at 25° C. N-[3-(aminomethyl)piperidin-1-yl]-N-methyl-7H-pyrrole[2,3-d]pyrimidine-4-amine (134.68 mg, 903.53 umol) was added, then Et$_3$N (752.49 mg, 7.44 mmol) was added, and the mixture was stirred to react for 12 h at 25° C. TLC showed that the raw materials were completely reacted, and LC-MS showed that there was a product generated. Stirring was stopped, and the mixture was concentrated under reduced pressure to remove DMF, and separated by a preparation HPLC (alkalic method) to obtain WX45: 2-cyano-N-((methyl(7H-pyrrole[2,3-d]pyrimidin-4-yl)amino)piperidin-3-yl)methyl)acetamide (7.70 mg, 6.27%). The value of C$_{16}$H$_{21}$N$_7$O[M+H]$^+$ 328.18 was calculated using MS ESI, and was 328. $^1$H NMR (400 MHz, METHANOL-d$_4$) δ=8.11 (s, 1H), 7.05 (s, 2H), 3.21 (s, 3H), 3.20-3.09 (m, 2H), 3.03-2.82 (m, 3H), 2.65-2.48 (m, 2H), 2.22-2.04 (m, 1H), 1.97-1.79 (m, 3H), 1.31-1.18 (m, 1H), 1.08-0.88 (m, 1H).

Embodiment 43

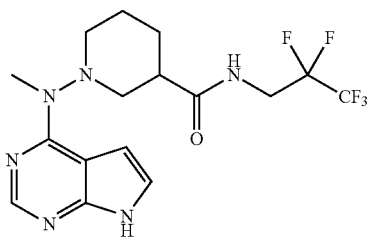

1-[methyl(7H-pyrrole[2,3-d] pyrimidine-4-)amino]-N-(2,2,3,3,3-pentafluoropropenyl)piperidyl-3-formamide

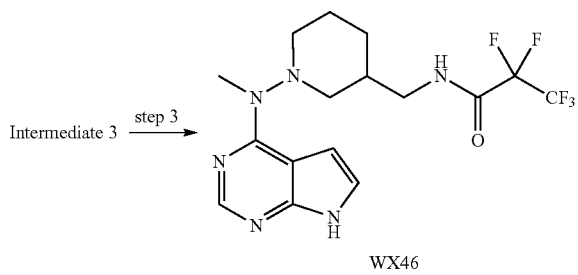

Step 1: the intermediate 3 (99.50 mg, 361.41 umol) was dissolved in DMF (5.00 mL), added with HOBt (146.50 mg, 1.08 mmol) and EDCI (207.85 mg, 1.08 mmol), and stirred for 30 min at 25° C. 2,2,3,3,3-pentafluoro propylamine (134.68 mg, 903.53 umol) and triethylamine (219.43 mg, 2.17 mmol) were added, and the mixture was stirred to react for 18 h at 25° C. LC-MS showed that the raw materials completely reacted, and there was a product generated. Stirring was stopped, the mixture was filtered, and the filtrate was concentrated to 5 mL, and separated by a preparation HPLC (alkalic method) to obtain WX46: 1-[methyl(7H-pyrrole[2,3-d]pyrimidine-4-)amino]-N-(2,2,3,3,3-pentafluoropropyl)piperidyl-3-formamide (49.70 mg, 33.84%). The value of $C_{16}H_{19}F_5N_6O[M+H]^+$ 407.15 was calculated using MS ESI, and was 407. $^1$H NMR (400 MHz, METHANOL-$d_4$) δ=8.13 (s, 1H), 7.08 (t, J=3.4 Hz, 2H), 4.09-3.80 (m, 2H), 3.22 (s, 3H), 3.08-2.83 (m, 5H), 2.01-1.85 (m, 3H), 1.58-1.40 (m, 1H).

Embodiment 44

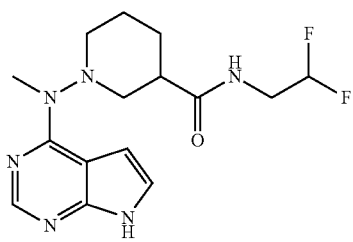

1-[methyl(7H-pyrrole[2,3-d]pyrimidine-4-)amino]-N-(2,2-difluoroethyl)piperidyl-3-formamide

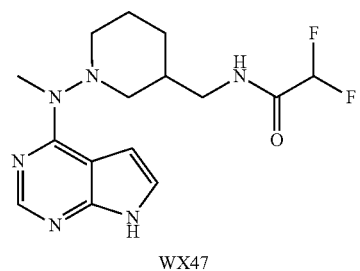

Step 1: the intermediate 3 (76.00 mg, 276.05 umol) was dissolved in DMF (4.00 mL), added with HOBt (111.90 mg, 828.15 umol) and EDCI (158.76 mg, 828.15 umol), and stirred for 30 min at 25° C. 2,2-difluoroethylamine (55.94 mg, 690.13 umol) and triethylamine (223.47 mg, 2.21 mmol) were added, and the mixture was stirred to react for 18 h at 25° C. LC-MS showed that the raw materials completely reacted, and there was a product generated. Stirring was stopped, the mixture was filtered, and the filtrate was concentrated, and separated by a preparation HPLC (alkalic method) to obtain WX47:

1-[methyl(7H-pyrrole[2,3-d]pyrimidine-4-)amino]-N-(2,2-difluoroethyl)piperidyl-3-formamide (42.82 mg, 45.85%). The value of $C_{15}H_{20}F_2N_6O[M+H]^+$ 339.17 was calculated using MS ESI, and was 339. $^1$H NMR (400 MHz, METHANOL-$d_4$) δ=8.12 (s, 1H), 7.11-7.02 (m, 2H), 6.06-5.67 (m, 1H), 3.66-3.45 (m, 2H), 3.22 (s, 3H), 3.09-2.98 (m, 2H), 2.96-2.84 (m, 3H), 2.05-1.83 (m, 3H), 1.58-1.39 (m, 1H).

Embodiment 45

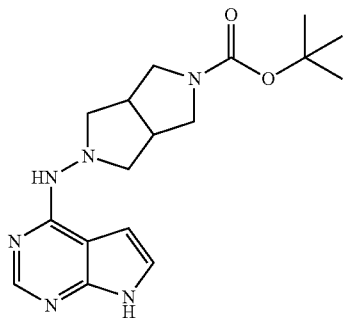

5-[[7H-pyrrole[2,3-d]pyrimidine-4-]amino]-hexahydropyrrolo[3,4-c]pyrrole-2(1H)-tert-butyl formate

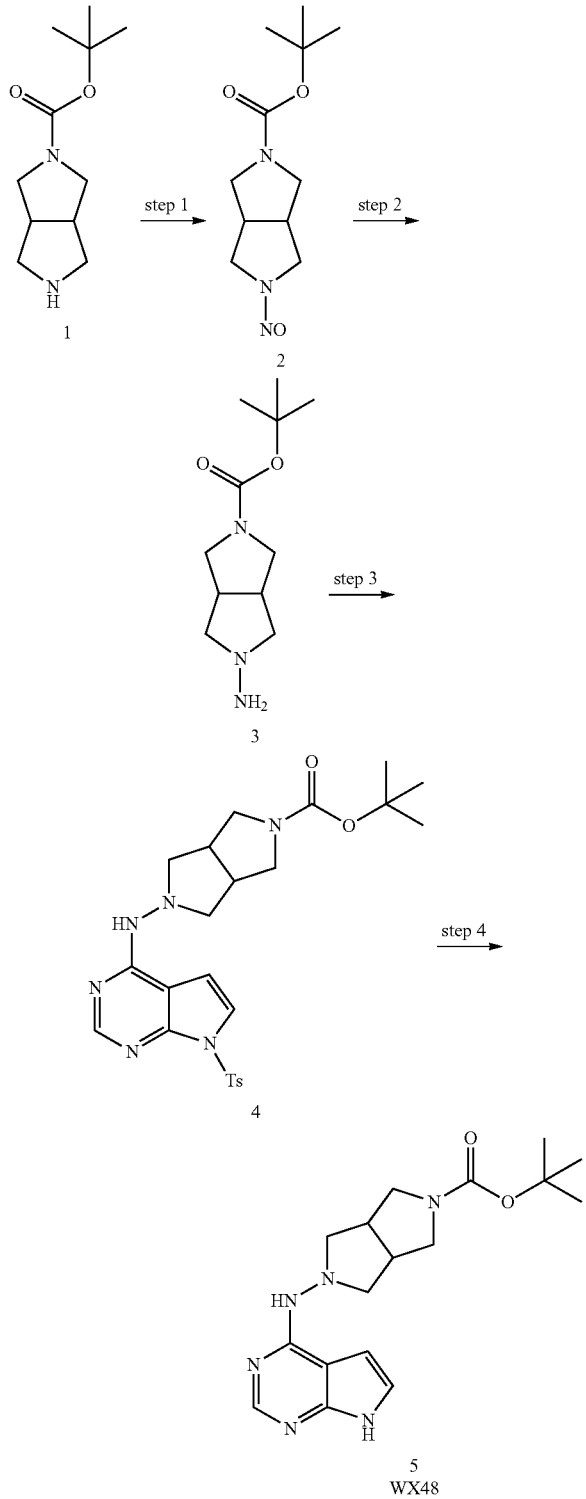

Step 1: hexahydropyrrolo[3,4-c]pyrrole-2(1H)-tert-butyl formate (1.50 g, 7.07 mmol) was dissolved in acetic acid (10.00 mL) and water (10.00 mL), cooled to 0° C., a $H_2O$ solution (10.00 mL) of $NaNO_2$ (1.22 g, 17.68 mmol) was dropwise added in 30 min at 0° C., and the mixture was continuously stirred for 2 h at 0° C. TLC (DCM:MeOH=10:1) showed that the raw materials were completely reacted. Stirring was stopped, and the mixture was adjusted by solid sodium carbonate to pH=8-9, and then extracted by mixed solvent (DCM:MeOH=10:1, 15 mL×3); organic layers were merged, washed by saturated saline solution (25 mL×1), dried by anhydrous sodium sulfate, filtered, and concentrated to obtain gray white solid 5-nitroso-hexahydropyrrolo[3,4-c]pyrrole-2(1H)-tert-butyl formate (1.27 g, crude product). $^1$H NMR (400 MHz, METHANOL-$d_4$) δ=4.57-4.43 (m, 1H), 4.25 (dd, J=4.9, 12.7 Hz, 1H), 3.85 (dd, J=7.8, 15.3 Hz, 1H), 3.65 (dd, J=5.3, 11.8 Hz, 2H), 3.49 (dd, J=4.9, 15.4 Hz, 1H), 3.31-3.21 (m, 2H), 3.18-2.99 (m, 2H), 1.48 (s, 9H).

Step 2: 5-nitroso-hexahydropyrrolo[3,4-c]pyrrole-2(1H)-tert-butyl formate (150.00 mg, 621.66 umol) was dissolved in methanol (5.00 mL), and added with zinc dust (609.76 mg, 9.32 mmol). The temperature was controlled to be between −10° C. and 5° C. under nitrogen protection, and AcOH (3.99 g, 66.44 mmol) was dropwise added, then the mixture was continuously stirred to react for 1 h. TLC (DCM:MeOH=10:1) showed that the raw materials were completely reacted. Stirring was stopped, the mixture was filtered, and the filtrate was concentrated, the solid obtained was dissolved in mixed solvent (DCM:MeOH=10:1, 10 ml) to remove solid matter, and then the filtrate was concentrated to obtain 5-amino-hexahydropyrrolo[3,4-c]pyrrole-2(1H)-tert-butyl formate (150.00 mg, crude product) which was directly used in next reaction without further purification. The value of $C_{18}H_{27}N_3O_4S[M+23]^+$404.17 was calculated using MS ESI, and was 404.

Step 3: 4-chloro-7-(tosyl)pyrrole[2,3-d]pyrimidine (169.00 mg, 549.13 umol) and 5-amino-hexahydropyrrolo[3,4-c]pyrrole-2(1H)-tert-butyl formate (149.78 mg, 658.96 umol) were dissolved in DCM (6.40 mL), added with triethylamine (278.13 mg, 2.75 mmol), and stirred to react for 16 h at 25° C. LC-MS showed the reaction was completed. Stirring was stopped and water (10 ml) was added, then the mixture was extracted by DCM (5 mL×3), and organic layers were merged, washed by saturated saline solution (25 mL×1), dried by anhydrous sodium sulfate, filtered and concentrated under reduced pressure, and separated by a preparation type TLC ($SiO_2$, PE:EA=1:1) to obtain faint yellow solid 5-[[7-(tosyl)pyrrole[2,3-d]pyrimidine-4-]amino]-hexahydropyrrolo[3,4-c]pyrrole-2(1H)-tert-butyl formate (161.80 mg, 59.10%). The value of $C_{24}H_{30}N_6O_4S[M+H]^+$ 499.20 was calculated using MS ESI, and was 499.

Step 4: 5-[[7-(tosyl)pyrrole[2,3-d]pyrimidine-4-]amino]-hexahydropyrrolo[3,4-c]pyrrole-2(1H)-tert-butyl formate (161.80 mg, 324.51 umol) was dissolved in $H_2O$:MeOH (10 mL, 1:1), added with NaOH (38.94 mg, 973.53 umol), and stirred to react for 12 h at 15° C. LC-MS showed the reaction was completed. Stirring was stopped, and the mixture was concentrated under reduced pressure, then methanol was removed, and the pH was adjusted to 8-9 by hydrochloric acid (1 M). Then the mixture was separated by a preparation HPLC (HCOOH) to obtain WX48: 5-[[7H-pyrrole[2,3-d]pyrimidine-4-]amino]-hexahydropyrrolo[3,4-c]pyrrole-2(1H)-tert-butyl formate (2.20 mg, 1.97%). The value of $C_{17}H_{24}N_6O_2[M+H]^+$ 345.20 was calculated using MS ESI, and was 345. $^1$H NMR (400 MHz, METHANOL-$d_4$) δ=8.16 (br. s., 1H), 7.26 (br. s., 1H), 6.80 (br. s., 1H), 3.62 (br. s., 2H), 3.46 (d, J=11.3 Hz, 2H), 3.02 (br. s., 4H), 2.17 (s, 2H), 1.52 (s, 9H).

Embodiment 46

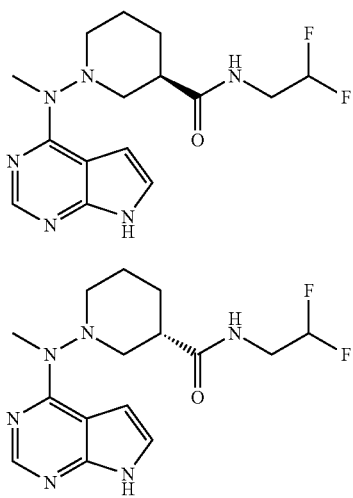

(3S or 3R)-1-[methyl(7H-pyrrole[2,3-d]pyrimidine-4-)amino]-N-(2,2-difluoroethyl)piperidyl-3-formamide

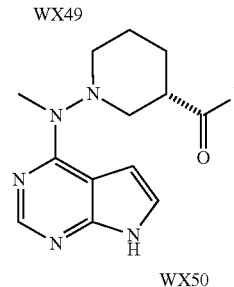

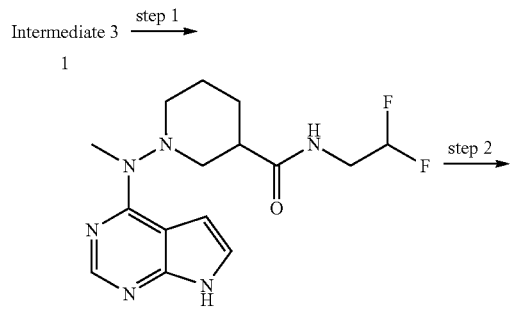

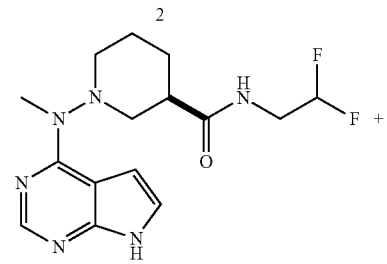

Step 1: the intermediate 3(600.00 mg, 2.18 mmol) was dissolved in DMF (30.00 mL), added with HOBt (441.71 3.27 mmol) and EDCI (626.68 mg, 3.27 mmol), and stirred for 30 min at 25° C. 2,2-difluoroethylamine (176.66 mg, 2.18 umol) and triethylamine (661.59 mg, 6.54 mmol) were added, and the mixture was stirred to react for 12 h at 25° C. LC-MS showed the reaction was completed. Stirring was stopped, then the mixture was concentrated under reduced pressure to remove DMF, and separated by an HPLC (alkalic method) to obtain 1-[methyl(7H-pyrrole[2,3-d]pyrimidine-4-)amino]-N-(2,2-difluoroethyl)piperidyl-3-formamide (210.00 mg, 28.13%). The value of $C_{15}H_{20}F_2N_6O$ [M+H]$^+$ 339.17 was calculated using MS ESI, and was 339.

Step 2: 1-[methyl(7H-pyrrole[2,3-d]pyrimidine-4-)amino]-N-(2,2-difluoroethyl)piperidyl-3-formamide (compound 2) (210.00 mg) was separated using supercritical-chromatography.

SFC separation conditions:
column: AD (250 mm*30 mm, 5 um) chiral column
mobile phase: A: supercritical CO2, B: 30% MeOH (0.1% NH$_3$H$_2$O), A:B=70:30 flow rate: 80 mL/min
column temperature: 38° C.
wavelength: 220 nm
jet pressure: 100 Bar
nozzle temperature: 60° C.
evaporating temperature: 20° C.
conditioning temperature: 25° C.

WX49 (3R or 3S)-1-[methyl(7H-pyrrole[2,3-d]pyrimidine-4-)amino]-N-(2,2-difluoroethyl)piperidyl-3-formamide (156.80 mg, 69.64%), retention time: 5.77 min. The value of $C_{18}H_{20}F_2N_6O$ [M+H]$^+$ 339.17 was calculated using MS ESI, and was 339. $^1$H NMR (400 MHz, METHANOL-d$_4$) δ=8.17-8.06 (m, 1H), 7.14-7.01 (m, 2H), 6.06-5.67 (m, 1H), 3.60-3.47 (m, 2H), 3.22 (s, 3H), 3.10-2.98 (m, 2H), 2.97-2.85 (m, 3H), 2.02-1.84 (m, 3H), 1.57-1.40 (m, 1H).

WX50 (3S or 3R)-1-[methyl(7H-pyrrole[2,3-d]pyrimidine-4-)amino]-N-(2,2-difluoroethyl)piperidyl-3-formamide (71.30 mg, 31.75%), retention time: 6.55 min. The value of $C_{15}H_{20}F_2N_6O$ [M+H]$^+$ 339.17 was calculated using MS ESI, and was 339. $^1$H NMR (400 MHz, METHANOL-d$_4$) δ=8.13 (s, 1H), 7.15-6.97 (m, 2H), 6.12-5.64 (m, 1H), 3.61-3.47 (m, 2H), 3.22 (s, 3H), 3.07-2.97 (m, 2H), 2.97-2.81 (m, 3H), 2.02-1.84 (m, 3H), 1.57-1.39 (m, 1H).

Embodiment 47

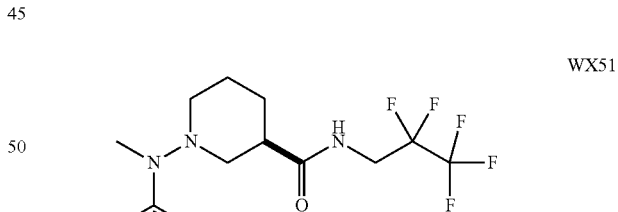

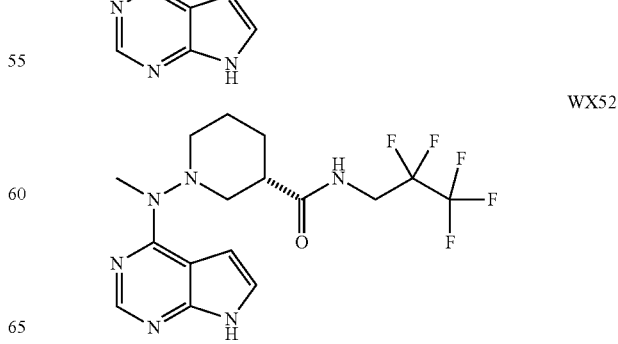

(3S or 3R)-1-[methyl(7H-pyrrole[2,3-d]pyrimidine-4-)amino]-N-(2,2,3,3,3-pentafluoropropyl)piperidyl-3-formamide

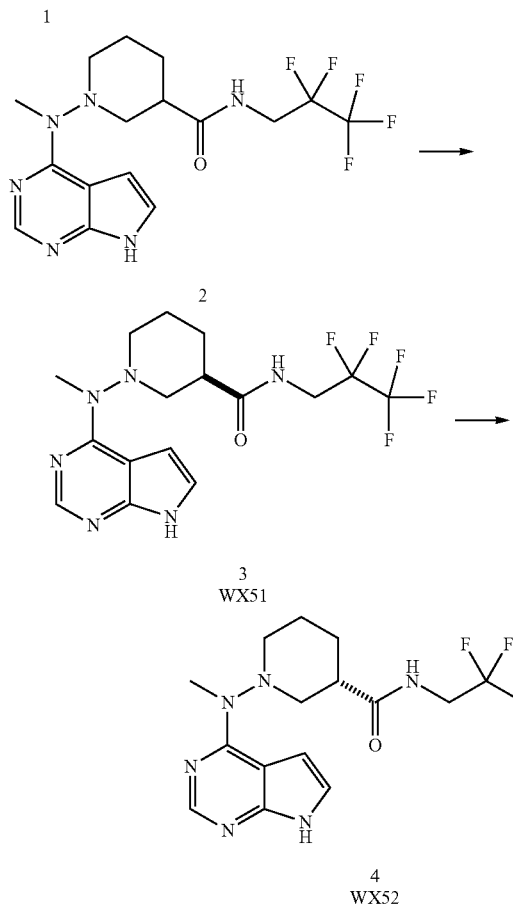

Step 1: the intermediate 3 (1.20 g, 4.36 mmol) was dissolved in DMF (20.00 mL), added with HOBt (1.77 g, 13.08 mmol) and EDCI (2.51 g, 13.08 mmol), and stirred for 30 min at 25° C. 2,2,3,3,3-pentafluoropropylamide (1.62 g, 10.90 mmol) and Et$_3$N (2.65 g, 26.15 mmol) were added, and the mixture was stirred to react for 12 h at 25° C. LC-MS showed that the raw materials completely reacted, and there was a product generated. Stirring was stopped, then the mixture was filtered, and the filtrate was concentrated to 5 mL, and separated by a preparation HPLC (alkalic) to obtain 1-[methyl(7H-pyrrole[2,3-d] pyrimidine-4-)amino]-N-(2,2,3,3,3-pentafluoropropyl)piper idyl-3-formamide (800.00 mg, 43.77%). The value of $C_{16}H_{19}F_5N_6O[M+H]^+$ 407.15 was calculated using MS ESI, and was 407.

Step 2: (1-[methyl(7H-pyrrole[2,3-d]pyrimidine-4-)amino]-N-(2,2,3,3,3-pentafluoropropyl)piperidyl-3-formamide (800.00 mg) was separated by supercriticalchromatography.

SFC separation conditions:
column: AD (250 mm*30 mm, 10 um) chiral column
Mobile phase: A: supercritical CO2, B: 40% MeOH (0.1% NH$_3$H$_2$O), A:B=60:40
flow rate: 70 mL/min
column temperature: 38° C.
wavelength: 220 nm
jet pressure: 100 Bar
nozzle temperature: 60° C.
evaporating temperature: 20° C.
conditioning temperature: 25° C.

WX51 (3R or 3S)-1-[methyl(7H-pyrrole[2,3-d]pyrimidine-4-)amino]-N-(2,2,3,3,3-pentafluoropropyl)piperidyl-3-formamide (401.50 mg, 46.90%), retention time: 5.77 min. The value of $C_{16}H_{19}F_5N_6O$ [M+H]$^+$ 407.15 was calculated using MS ESI, and was 407. $^1$H NMR (400 MHz, METHANOL-d$_4$) δ=8.13 (s, 1H), 7.13-7.02 (m, 2H), 4.11-3.80 (m, 2H), 3.23 (s, 3H), 3.08-2.84 (m, 5H), 2.06-1.83 (m, 3H), 1.49 (d, J=11.5 Hz, 1H).

WX52 (3S or 3R)-1-[methyl(7H-pyrrole[2,3-d]pyrimidine-4-)amino]-N-(2,2,3,3,3-pentafluoropropyl)piperidyl-3-formamide (395.60 mg, 46.06%), retention time: 6.89 min. The value of $C_{16}H_{19}F_5N_6O[M+H]^+$ 407.15 was calculated using MS ESI, and was 407. $^1$H NMR (400 MHz, METHANOL-d$_4$) δ=8.13 (s, 1H), 7.08 (s, 2H), 4.14-3.81 (m, 2H), 3.23 (s, 3H), 3.11-2.76 (m, 5H), 2.07-1.84 (m, 3H), 1.63-1.41 (m, 1H).

Embodiment 48

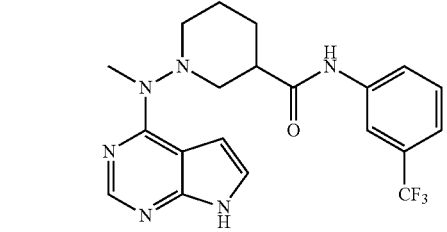

1-[methyl(7H-pyrrolo[2,3-d]pyrimidin-4-yl)amino]-N-[3-(trifluoromethyl)phenyl]piperidyl-3-formamide

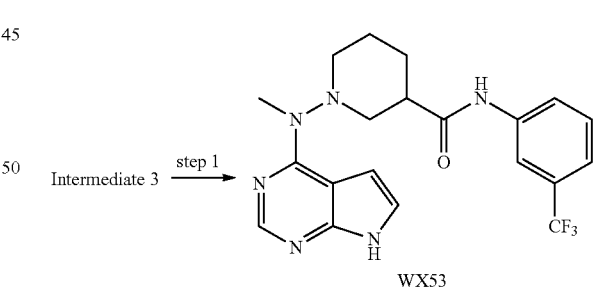

Step 1: EDCI (174.08 mg, 908.08 umol) was added into a pyridine solution (5.00 mL) of the intermediate 3 (100.00 mg, 363.23 umol), and then 3-(trifluoromethyl)phenylamine (64.38 mg, 399.55 umol) was added at 0° C. The mixture was warmed up to 25° C., and stirred for 10 h at 25° C. LC-MS showed the reaction was completed. The solvent was removed under reduced pressure. Residues were diluted by water (10 mL) and extracted by dichloromethane:methanol (15 mL×2, 5/1). Merged organic layers were concentrated under reduced pressure to obtain residues.

The residues were purified by a preparation type HPLC (alkalic condition) to obtain WX53: 1-[methyl(7H-pyrrolo

[2,3-d]pyrimidin-4-yl)amino]-N-[3-(trifluoromethyl)phenyl]piperidyl-3-formamide (50.00 mg, yield was 32.90%). ¹H NMR (400 MHz, MeOD-d₄) δ=8.11 (s, 1H), 8.02 (br. s., 1H), 7.73 (d, J=8.0 Hz, 1H), 7.46 (t, J=7.9 Hz, 1H), 7.35 (d, J=7.5 Hz, 1H), 7.09 (d, J=5.3 Hz, 2H), 3.22 (s, 3H), 2.88-3.16 (m, 5H), 1.88-2.09 (m, 3H), 1.40-1.66 (m, 1H). The value of $C_{20}H_{21}F_3N_6O[M+H]^+$ 419 was calculated using MS ESI, and was 419.

Embodiment 49

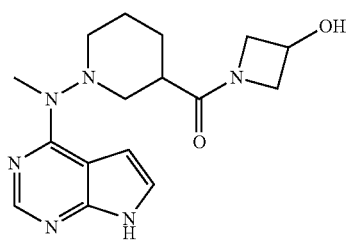

WX54

(3-hydroxyazetidin-1-yl)-[1-[methyl(7H-pyrrolo[2,3-d]pyrimidin-4-yl)amino)-3-piperidinyl]ketone

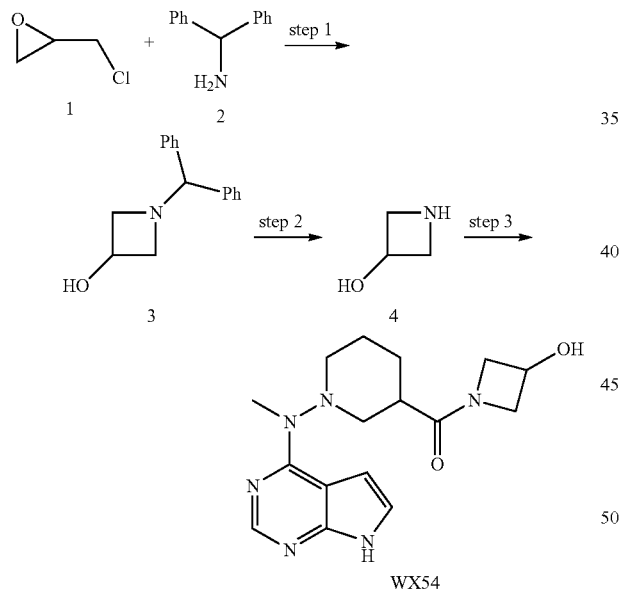

Step 1: 2-(chloromethyl)ethylene oxide (5.05 g, 54.58 mmol) was dropwise added to a methanol solution (55 mL) of benzhydryl amine (10.00 g, 54.58 mmol) under nitrogen protection at 0° C., then the reaction solution was warmed up to 28° C. and stirred for 10 h. LCMS showed that the reaction was completed. The mixture was concentrated under reduced pressure to obtain 1-(benzylaminopyridine)-3-chloropropyl-2-ol (15.00 g, crude product) which was yellow liquid and directly used in next step. Then, DIEA (7.03 g, 54.39 mmol) was added to an ethanol solution (100 mL) of 1-(benzylaminopyridine)-3-chloropropyl-2-ol (15.00 g, 54.39 mmol); the reaction solution was heated to 90° C. and stirred for 10 h. LCMS showed that the reaction was completed. The mixture was cooled to 25° C. and was concentrated under reduced pressure. The concentrate was recrystallized by acetone and petroleum ether to obtain 1-benzhydrylazetan-3-ol (7.10 g, yield was 51.82%) which was white solid. The value of $C_{16}H_{17}NO[M+H]^+$ 240 was calculated using MS ESI, and was 240.

Step 2: Pd—C(10%, 500 mg) was added in a methanol solution (15 mL) of 1-benzhydrylazetan-3-ol (1.00 g, 4.18 mmol) under nitrogen protection. The reaction solution was replaced by hydrogen for multiple times, and then stirred for 10 h under hydrogen (15 psi) protection at 30° C. TLC showed that the reaction was completed. The reaction mixture was filtered and concentrated to obtain azetidine-3-ol which was colorless oily matter (600.00 mg, crude product). The value of $C_3H_7NO[M+H]^+$ 74 was calculated using MS ESI, and was 74.

Step 3: HOBt (122.70 mg, 908.08 umol), EDCI (174.08 mg, 908.08 umol) and TEA (220.53 mg, 2.18 umol) were added into intermediate 3 (100.00 mg, 363.23 umol) and a DMF solution (10 mL) of azetidine-3-ol (26.5 mg, 365 umol). The mixture was stirred for 10 h at normal temperature. LCMS showed that the reaction was completed. The mixture was poured into water (20 mL). The aqueous phase was extracted using ethyl acetate (15 mL×3). Merged organic phases were washed by saturated saline solution (10 mL), dried by anhydrous sodium sulfate, filtered and concentrated, and residues were purified through a preparation type HPLC (alkalic condition) to obtain WX54: (3-hydroxyazetidine-1-yl)-[[1-[methyl(7H-pyrrolo[2,3-d]pyrimidin-4-yl)amino)-3-piperidinyl]ketone (5.00 mg, yield was 3.75%). ¹H NMR (400 MHz, MeOD-d₄) δ=8.14 (s, 1H), 7.00-7.22 (m, 2H), 4.35-4.61 (m, 2H), 3.91-4.21 (m, 2H), 3.51-3.78 (m, 2H), 3.21-3.27 (m, 2H), 2.84-3.01 (m, 5H), 1.84-2.03 (m, 3H), 1.36-1.51 (m, 1H). The value of $C_{16}H_{22}N_6O_2[M+H]^+$ 331 was calculated using MS ESI, and was 331.

Embodiment 50

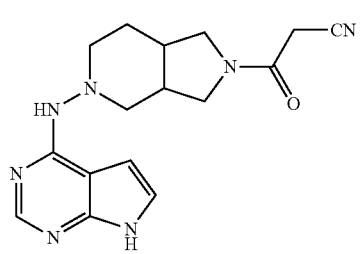

WX55

3-[5-(7H-pyrrolo[2,3-d]pyrimidin-4-ylamino)-hexahydro-1H-pyrrolo[3,4-c]pyridine-2-yl]3-oxopropanenitrile

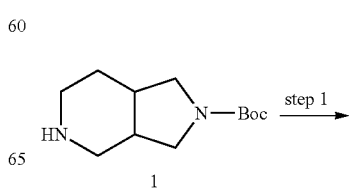

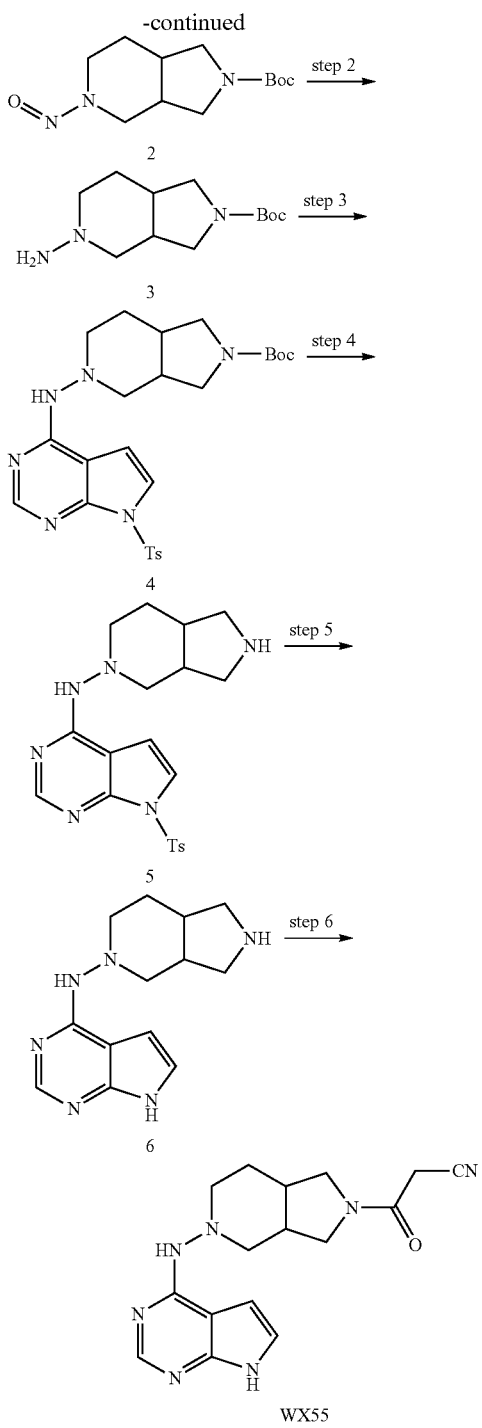

Step 1: a water solution (10.00 mL) of sodium nitrite (420.00 mg, 6.09 umol) was dropwise added to a mixed solution of acetic acid (10.00 mL) and water (10.00 mL) of tert-butylhexahydro-1H-pyrrolo[3,4-c]pyridine-2(3H)-carboxylic ester (800.00 mg, 3.04 umol) at 0° C. After the sodium nitrite solution was added, the mixture was warmed up to 25° C. and stirred for 2 h. TLC showed that the raw materials were consumed. The reaction solution was diluted by water (20 mL) and extracted by ethyl acetate (30 mL×2). Merged organic layers were adjusted by saturated sodium dicarbonate to pH=8-9, washed by saline solution (10 mL×2), dried by anhydrous sodium sulfate, filtered and concentrated under reduced pressure to obtain tert-butyl-5-nitrosohexahydro-1H-pyrrolo[3,4-c]pyridine-2(3H)-carboxylic ester (650.00 mg, crude product) which was yellow oily matter. The product was directly used in next step without needing further purification. The value of $C_{12}H_{21}N_3O_3[M+H]^+$ 256 was calculated using MS ESI, and was 256.

Step 2: acetic acid (5.00 mL) was dropwise added to a methanol solution (10.00 mL) of tert-butyl-5-nitrosohexahydro-1H-pyrrolo[3,4-c]pyridine-2(3H)-carboxylic ester (650.00 mg, 2.55 umol) and zinc dust (833.72 mg, 12.75 umol) at −5° C. to −10°. After the acetic acid was added, the mixture was slowly warmed up to 25° C. and stirred for 2 h. TLC showed that the initial materials were completely consumed. The solid was filtered out, then the mixture was filtered and concentrated under reduced pressure to obtain tert-butyl-5-aminohexahydro-1H-pyrrolo[3,4-c]pyridine-2(3H)-carboxylic ester (620.00 mg, crude product) which was white solid. The product was directly used in next step without purification. The value of $C_{12}H_{23}N_3O_2[M+H]^+$ 242 was calculated using MS ESI, and was 242.

Step 3: a dichloromethane solution (15.00 mL) of tert-butyl-5-aminohexahydro-1H-pyrrolo[3,4-c]pyridine-2(3H)-carboxylic ester (620.00 mg, 2.06 umol), 4-chloro-7-(tosyl)pyrrolo[2,3-d]pyrimidine (633.12 mg, 2.06 umol) and triethylamine (1.25 g, 12.36 mmol) was heated to 50° C. and stirred for 10 h at 50° C. LC-MS showed the reaction was completed. The reaction mixture was concentrated under reduced pressure to obtain residues. The residues were purified through column chromatography (petroleum ether: ethyl acetate=5/1 to 2/1) to obtain tert-butyl 5-(7-(tosyl)pyrrolo[2,3-d]pyrimidin-4-yl]aminohexahydro-1H-pyrrolo[3,4-c]pyridine-2(3H)-carboxylic ester (270.00 mg, yield was 20.97%) which was white solid. The value of $C_{25}H_{32}N_6O_4S[M+H]^+$ 513 was calculated using MS ESI, and was 513.

Step 4: Dioxane hydrochloride (4 M, 5.00 mL) was added to a DCM solution (3.00 mL) of tert-butyl 5-(7-(tosyl)pyrrolo[2,3-d]pyrimidin-4-yl]aminohexahydro-1H-pyrrolo[3,4-c]pyridine-2(3H)-carboxylic ester (270.00 mg, 526.71 umol), and the mixture was stirred for 2 h at normal temperature. LC-MS showed that the original raw materials were completely consumed. The reaction mixture was concentrated under reduced pressure to obtain N-hexahydro-1H-pyrrolo[3,4-c]pyridin-5(6H)-yl-7-(tosyl)₇H-pyrrolo[2,3-d]pyrimidine-4-amine (340.00 mg, crude product) which was buff solid and directly used in next step without purification. The value of $C_2OH_{24}N_6O_2S[M+H]^+$ 413 was calculated using MS ESI, and was 413.

Step 5: potassium carbonate (284.79 mg, 2.06 umol) was added into a solution of methanol (5.00 mL) and water (1.00 mL) of N-hexahydro-1H-pyrrolo[3,4-c]pyridin-5(6H)-yl-7-(tosyl)₇H-pyrrolo[2,3-d]pyrimidine-4-amine (170.00 mg, 412.11 umol). The mixture was heated to 70° C. and stirred for 2 h. TLC showed that the raw materials were consumed. The reaction mixture was concentrated under reduced pressure to obtain N-hexahydro-1H-pyrrolo[3,4-c]pyridin-5(6H)-yl-7-(tosyl)7H-pyrrolo[2,3-d]pyrimidine-4-amine (50.00 mg, crude product) which was buff solid and directly used in next step without purification. The value of $C_{13}H_{18}N_6[M+H]^+$ 259 was calculated using MS ESI, and was 259.

Step 6: HOBt (65.38 mg, 483.90 umol) and EDCI (92.76 mg, 483.90 umol) were added in a DMF solution (5.00 mL) of N-hexahydro-1H-pyrrolo[3,4-c]pyridin-5(6H)-yl-7H-pyrrolo[2,3-d]pyrimidine-4-amine at 0° C. After that, the mixture was stirred for 10 min at 0° C., and then 2-cyanoacetic acid (18.11 mg, 212.92 umol) and triethylamine (117.52 mg, 1.16 mmol) were added. The mixture was stirred for 10 h at 25° C. LC-MS showed the reaction was completed. The reaction mixture was poured into ice water (5 mL), and then extracted using dichloromethane:methanol (20 mL×3). Merged organic layers were concentrated under reduced pressure to obtain residues. The residues were purified through a preparation type HPLC (alkalic method) to obtain WX55:

3-[5-(7H-pyrrolo[2,3-d]pyrimidin-4-ylamino)-hexahydro-1H-pyrrolo[3,4-c]pyridin-2-yl]3-oxopropanenitrile (5.00 mg, yield was 7.52%). $^1$H NMR (400 MHz, MeOD-d$_4$) δ=8.07 (d, J=6.0 Hz, 1H), 7.10 (t, J=3.0 Hz, 1H), 6.82 (br. s., 1H), 3.40-4.13 (m, 5H), 1.67-3.24 (m, 9H). The value of $C_{16}H_{19}N_7O[M+H]^+$ 326 was calculated using MS ESI, and was 326.

Embodiment 51

WX56

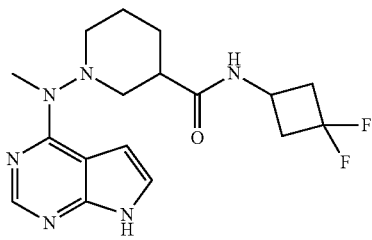

N-(3,3-difluoro-cyclobutyl)-1-[methyl(7H-pyrrolo[2,3-d]pyrimidin-4-yl)amino]piperidyl)-3-formamide

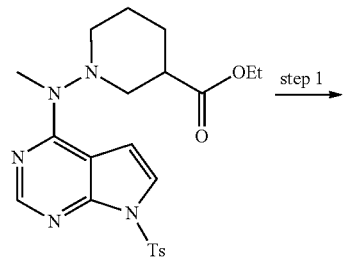

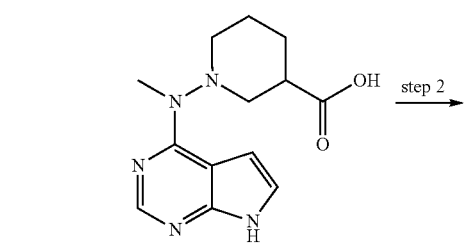

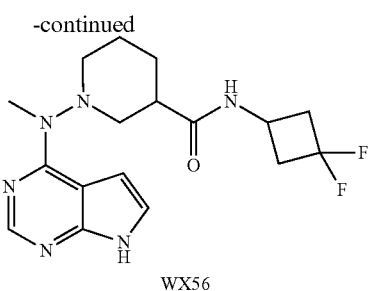

WX56

Step 1: ethyl 1-[methyl-[7-(tosyl)pyrrole[2,3-d]pyrimidin-4-yl]amino]piperidyl-3-carboxylic ester (130.00 mg, 284.13 umol) was dissolved in tetrahydrofuran (5 mL) and methanol (5 mL), and a solution (2.5 mL) of sodium hydroxide (22.73 mg, 568.26 umol) was added. Then the mixture was heated to 100° C. and stirred for 2 h. LC-MS showed the reaction was completed. The mixture was cooled to 25° C., and then concentrated under reduced pressure at 50° C. Residues were neutralized by diluted HCl (aqueous solution), and concentrated under reduced pressure to obtain 1-[methyl(7H-pyrrolo[2,3-d]pyrimidin-4-yl)ylamino]piperidyl-3-carboxylic acid (crude product) which was yellow solid and directly used in next step. The value of $C_{13}H_{17}N_5O_2[M+H]^+$ 276, was calculated using MS ESI, and was 276.

Step 2: 1-[methyl(7H-pyrrolo[2,3-d]pyrimidin-4-yl)amino]piperidyl-3-carboxylic acid (78.00 mg, 283.32 umol), HOBt (76.56 mg, 566.64 umol) and EDCI (108.62 mg, 566.64 umol) were dissolved in DMF (3.5 mL), stirred for 35 min at 25° C., and then added with 3,3-difluorocyclobutanamine (81.35 mg, 566.63 umol) and triethylamine (114.68 mg, 1.13 mmol). The mixture was stirred for 12 h at 25° C. LC-MS showed the reaction was completed. The mixture was diluted by water (5 mL), and extracted by dichloromethane:methanol (5:1, 50 mL×3). Merged organic phases were washed by saturated saline water (20 mL), dried by anhydrous sodium sulfate, filtered and concentrated to be dry under reduced pressure. Residues were purified using a preparation HPLC (alkalic method) to obtain WX56: N-(3,3-difluoro-cyclobutyl)-1-[(7H-pyrrolo[2,3-d]pyrimidin-4-yl)amino]piperidyl)-3-formamide (50.00 mg, yield was 48.43%). The value of $C_{17}H_{22}F_2N_6O[M+H]^+$ 365 was calculated using MS ESI, and was 365. $^1$H NMR (400 MHz, METHANOL-d$_4$) δ=8.12 (s, 1H), 7.07 (s, 2H), 4.16-4.06 (m, 1H), 3.22 (s, 3H), 3.05-2.82 (m, 6H), 2.61-2.44 (m, 2H), 1.92 (br. s., 2H), 1.56-1.41 (m, 1H). The value of $C_{17}H_{22}F_2N_6O[M+H]^+$ 365 was calculated using MS ESI, and was 365.

Embodiment 52

WX57

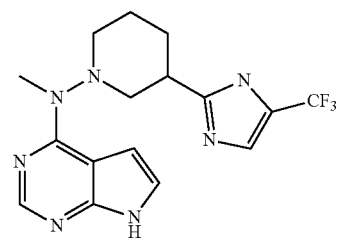

103

N-methyl-N-[3-[5-trifluoromethyl-1H-imidazole-2-yl]-1-piperidinyl]-7H-pyrrolo[2,3-d]pyrimidine-4-amine

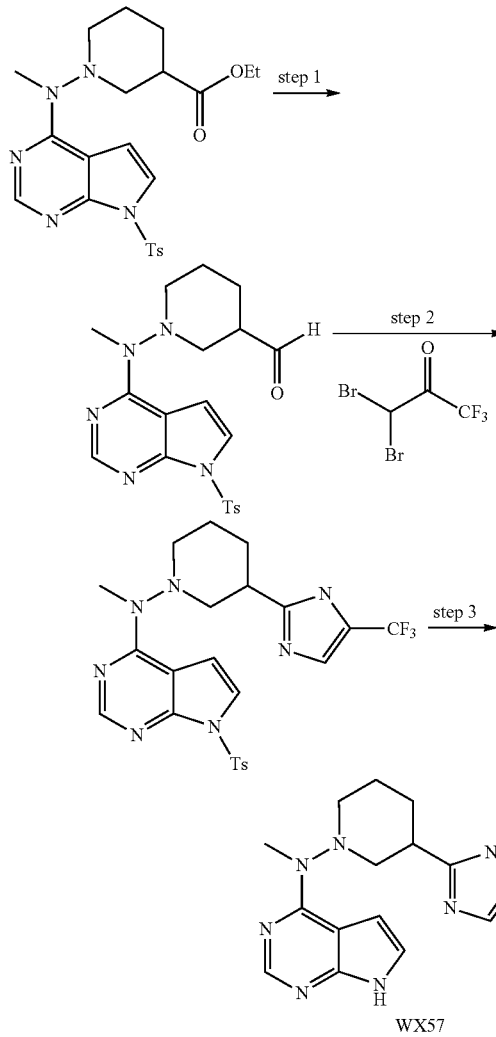

Step 1: 1-[methyl-[7-(tosyl)pyrrolo[2,3-d]pyrimidin-4-yl]amine]piperidyl-3-carboxylate (800.00 mg, 1.75 mmol) was dissolved in dry dichloromethane (20.00 mL), and a toluol solution of DIBAL-H (1 M, 1.93 mL) was dropwise added at −78° C., and the mixture was stirred for 30 min under −78° C. When TLC showed that the raw materials were consumed, a saturated ammonium chloride solution (2.0 mL) was added to quench, then jelly matters were filtered and removed by diatomite, and the mixture was washed by dichloromethane. After organic phases were separated, the aqueous phase was extracted by dichloromethane (50 mL). Merged organic phases were washed by saturated saline water, dried by sodium sulfate and concentrated to obtain solid, residues were purified by silica gel chromatography (100-200 mesh silica gel, petroleum ether:ethyl acetate=4:1 to 2:1), to obtain 1-[methyl-[7-(tosyl)pyrrole[2,3-d]pyrimidin-4-yl]amino]piperidyl-3-formaldehyde (530.00 mg, yield was 69.58%) which was faint yellow solid. The value of $C_{20}H_{23}N_5O_3S[M+H]^+$ 414 was calculated using MS ESI, and was 414.

Step 2: 3,3-dibromo-1,1,1-trifluoro-propan-2-one (215.36 mg, 798.08 umol) was added to a methanol solution of 1-[methyl-[7-(tosyl)pyrrole[2,3-d]pyrimidin-4-yl]amino]piperidyl-3-formaldehyde (300.00 mg, 725.53 umol); the mixture was stirred for 24 h at 25° C., added with water (20 mL) for dilution, and extracted by ethyl acetate (50 mL×3). Merged organic phases were washed by saturated saline water (20 mL×2), dried by anhydrous sodium sulfate, filtered and concentrated to be dry under reduced pressure. Residues were purified by a TLC (petroleum ether:ethyl acetate=1:1) to obtain N-methyl-7-p(tosyl)-N-[3-[5-trifluoromethyl-1H-imidazol-2-yl]-1-piperidinyl]-7H-pyrrolo[2,3-d]pyrimidine-4-amine (230.00 mg, yield was 58.58%). The value of $C_{23}H_{24}F_3N_7O_2S[M+H]^+$ 520 was calculated using MS ESI, and was 520.

Step 3: N-methyl-7-p(tosyl)-N-[3-[5-trifluoromethyl-1H-imidazol-2-yl]-1-piperidinyl]-7H-pyrrolo[2,3-d]pyrimidine-4-amine (115.00 mg, 221.35 umol) was dissolved in tetrahydrofuran (5 mL) and methanol (5 mL), and added with a water solution (2.5 mL) of sodium hydroxide (88.54 mg, 2.21 mmol). Then the mixture was heated to 40° C. and stirred for 2 h. TLC showed that the reaction was completed. The mixture is cooled to be lower than 30° C. and concentrated under reduced pressure to remove tetrahydrofuran. Residues were diluted by water (10 mL) and extracted by dichloromethane/methanol (10:1, 50 mL×2). Merged organic phases were washed by saturated saline water (20 mL×2), dried by anhydrous sodium sulfate, filtered and concentrated to be dry under reduced pressure. The residues were purified by alkalic preparation HPLC to obtain WX57: N-methyl-N-[3-[5-trifluoromethyl-1H-imidazol-2-yl]-1-piperidinyl]-7H-pyrrolo[2,3-d]pyrimidine-4-amine (40.00 mg, yield was 49.46%). The value of $C_{16}H_{18}F_3N_7[M+H]^+$ 366 was calculated using MS ESI, and was 366. $^1$H NMR (400 MHz, METHANOL-$d_4$) δ=8.13 (s, 1H), 7.48 (br. s., 1H), 7.12 (d, J=15.6 Hz, 2H), 3.40 (d, J=11.5 Hz, 2H), 3.26 (br. s., 3H), 3.19 (br. s., 1H), 3.14-3.07 (m, 1H), 3.02 (br. s., 2H), 2.13 (d, J=12.5 Hz, 1H), 2.07-1.94 (m, 2H), 1.68-1.56 (m, 1H). The value of $C_{16}H_{18}F_3N_7[M+H]^+$ 366 was calculated using MS ESI, and was 366.

Embodiment 53

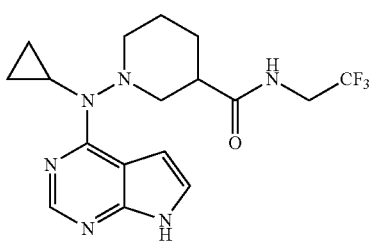

WX58

1-[cyclopropyl(7H-pyrrolo[2,3-d]pyrimidin-4-yl)amino]-N-(2,2,2-trifluoroethyl)piperidyl-3-formamide

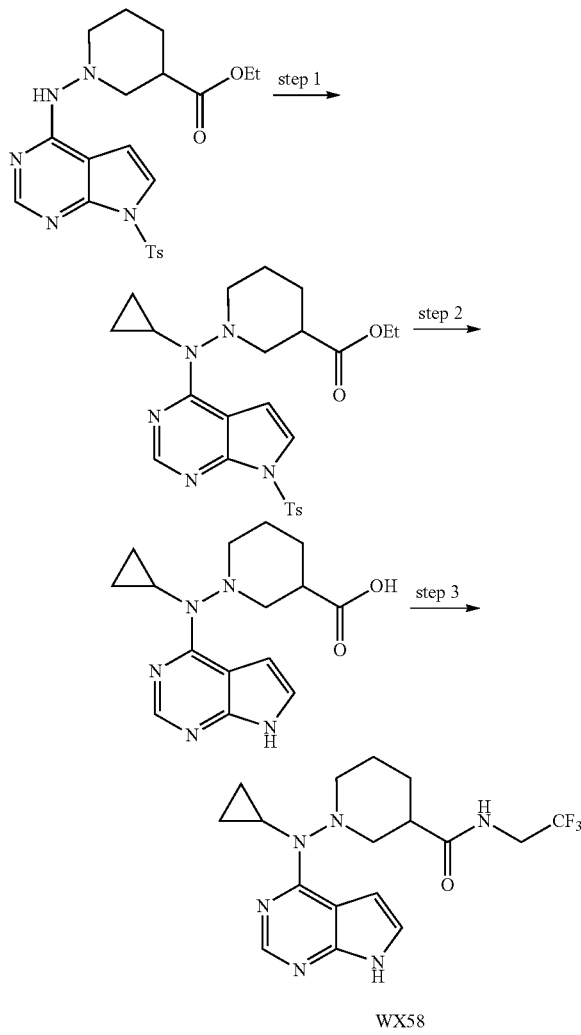

WX58

Step 1: ethyl 1-[[7-(tosyl)pyrrolo[2,3-d]pyrimidin-4-yl]amino]piperidyl-3-carboxylate (501.18 mg, 1.13 mmol) and bromocyclopropane (1.00 g, 8.26 mmol) were dissolved in DMF (10.00 mL), and added with potassium carbonate (780.89 mg, 5.65 mmol) and potassium iodide (18.76 mg, 113.00 umol). The mixture was stirred for 48 h at 50° C. LC-MS showed that 9% raw materials were remained and 6% target products were detected. Another portion of bromocyclopropane (5.00 g, 41.33 mmol) was added, and the mixture was heated to 100° C. and stirred for 2 h. LC-MS showed that 12% raw materials were remained and 40% target products were detected. The reaction solution was added with water (10 mL) to quench at 25° C. and extracted using ethyl acetate (100 mL×2). Merged organic phases were washed by saturated saline solution (20 mL×2), dried by anhydrous sodium sulfate, filtered and concentrated under reduced pressure. Residues were purified by a preparation TLC (silicon dioxide, petroleum ether:ethyl acetate=3:1) to obtain ethyl 1-[cyclohexyl-[7-(tosyl)pyrrolo[2,3-d]pyrimidin-4-yl]amino]piperidyl-3-carboxylate (50.00 mg, yield was 6.86%) which was faint yellow oil. The value of $C_{24}H_{29}N_5O_4S[M+H]^+$ 484 was calculated using MS ESI, and was 484.

Step 2: ethyl 1-[cyclopropyl-[7-(tosyl)pyrrole[2,3-d]pyrimidin-4-yl]amino]piperidyl-3-carboxylate (50.00 mg, 103.40 umol) was dissolved in tetrahydrofuran (5 mL) and methanol (5 mL), and a solution (2.5 mL) of sodium hydroxide (8.27 mg, 206.80 umol) was added. Then the mixture was heated to 100° C. and stirred for 1 h. LC-MS showed the reaction was completed. The mixture was concentrated under reduced pressure. Residues were neutralized by diluted HCl (2 M, 20 drops) to obtain 1-[cyclopropyl-[7H-pyrrolo[2,3-d]pyrimidin-4-yl]amino]piperidyl-3-carboxylic acid (80.00 mg, crude product) which was directly used in next step without further purification. The value of $C_{15}H_{19}N_5O_2[M+H]^+$ 302 was calculated using MS ESI, and was 302.

Step 3: 1-[cyclopropyl-[7H-pyrrolo[2,3-d]pyrimidin-4-yl]amino]piperidyl-3-carboxylic acid (50.00 mg, 165.93 umol), HOBt (44.84 mg, 331.86 umol) and EDCI (63.62 mg, 331.86 umol) were dissolved in DMF (4 mL), stirred for 30 min at 25° C., and then added with 2,2,2-trifluoroethylamine (24.65 mg, 248.89 umol) and triethylamine (50.37 mg, 497.79 umol) in sequence. The mixture was stirred for 16 h at 25° C. LC-MS showed the reaction was completed. The mixture was added with water (10 mL) to quench and extracted by ethyl acetate (50 mL×2). Merged organic phases were washed by saturated saline water (20 mL×2), dried by anhydrous sodium sulfate, filtered, concentrated and dried under reduced pressure. Residues were purified by an alkalic preparation HPLC to obtain WX58: 1-[cyclopropyl(7H-pyrrolo[2,3-d]pyrimidin-4-yl)amino]-N-(2,2,2-trifluoroethyl)piperidyl-3-formamide (20.00 mg, yield was 31.52%). The value of $C_{17}H_{21}F_3N_6O[M+H]^+$ 383 was calculated using MS ESI, and was 383.

Embodiment 54

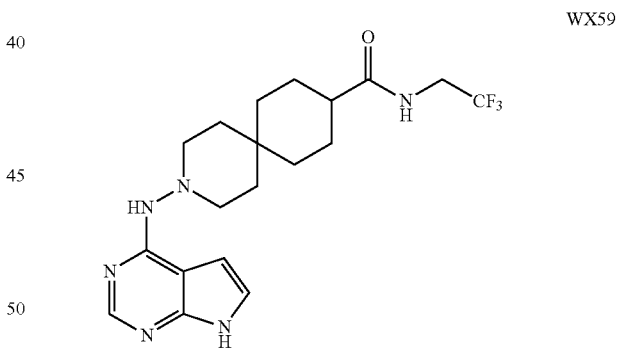

WX59

3-(7H-pyrrolo[2,3-d]pyrimidin-4-yl)amino)-N-(2,2,2-trifluoroethyl)-3-azaspiro[5.5]undecane-9-formamide

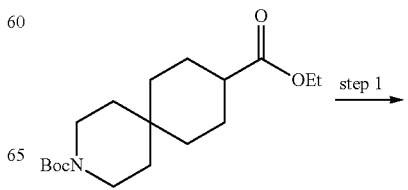

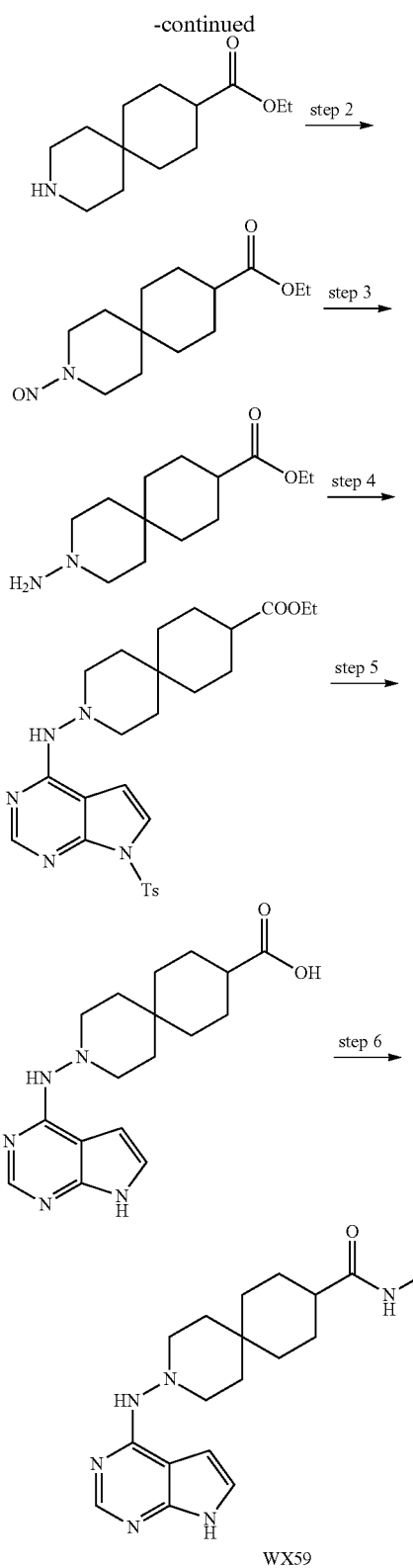

WX59

Step 1: hydrochloric acid/dioxane solution (4 M, 2.30 mL) was added to a dichloromethane solution (10 mL) of 3-t-butyloxycarboryl-3-azaspiro[5.5]undecane-9-carboxylic acid ethyl ester (300.00 mg, 921.83 umol). The mixture was stirred for 0.5 h at 25° C. TLC showed that the reaction was completed. The reaction solution was concentrated under reduced pressure to obtain 3-azaspiro[5.5]undecane-9-carboxylic acid ethyl ester (300.00 mg, crude product) which was faint yellow solid and directly used in next reaction without further purification. The value of $C_{13}H_{23}NO_2[M+H]^+$ 226 was calculated using MS ESI, and was 226.

Step 2: 3-azaspiro[5.5]undecane-9-carboxylic acid ethyl ester (300.00 mg, 1.15 mmol) was dissolved in acetic acid (10.00 mL) and water (5.00 mL), and an aqueous solution (5.00 mL) of sodium nitrite (158.14 mg, 2.29 mmol) was dropwise added in the foregoing solution at 0° C. The mixture was stirred for 2 h at 25° C. TLC showed that the reaction was completed. The mixture was added with water (5 mL) to quench. An aqueous phase was extracted using ethyl acetate (50 mL×2), and merged organic phases were washed by saturated saline water (20 mL), dried by anhydrous sodium sulfate, filtered, and concentrated under reduced pressure. Residues were dissolved in water (10 mL) and alkalized by solid sodium hydrogen carbonate to pH=9, and then extracted using ethyl acetate (50 mL×2); merged organic phases were washed by saturated saline water (20 mL), dried by anhydrous sodium sulfate, filtered and concentrated under reduced pressure to obtain 3-nitroso-3-azaspiro[5.5]undecane-9-ethyl formate (200.00 mg, crude product) which was pale yellow oil. The value of $C_{13}H_{22}N_2O_3[M+H]^+$ 225 was calculated using MS ESI, and was 255.

Step 3: 3-nitroso-3-azaspiro[5.5]undecane-9-ethyl formate (200.00 mg, 786.41 was dissolved in methanol (5.00 mL) and cooled to −10° C., zinc (257.12 mg, 3.93 mmol) was added in the solution under nitrogen protection, and acetic acid (472.24 mg, 7.86 mmol) was dropwise added under −10-0° C. The mixture was stirred for 30 min at 0° C., and then stirred for 1.5 h at 25° C. TLC showed that the reaction was completed. The mixture was filtered and washed by methanol (30 mL). The filtrate was concentrated under reduced pressure and under 70° C. Residues were dissolved in dichloromethane:methanol (10:1 20 mL), and alkalized by solid sodium hydrogen carbonate to pH=8-9. The mixture was filtered by diatomite and washed by dichloromethane:methanol (10:1 50 mL). The filtrate was concentrated under reduced pressure to obtain 3-amino-3-azaspiro[5.5]undecane-9-ethyl formate (200.00 mg, crude product) which was yellow oily matter and directly used in next step. The value of $C_{13}H_{24}N_2O_2[M+H]^+$ 241 was calculated using MS ESI, and was 241.

Step 4: 3-amino-3-azaspiro[5.5]undecane-9-ethyl formate (200.00 mg, 832.15 umol) was dissolved in dioxane (10.00 mL), and added with triethylamine (421.03 mg, 4.16 mmol) and 4-chloro-7-(tosyl)pyrrolo[2,3-d]pyrimidine (256.10 mg, 832.15 umol); then the foregoing mixture was stirred for 16 h under nitrogen protection at 110° C. LC-MS showed that 60% 4-chloro-7-(tosyl)pyrrolo[2,3-d]pyrimidine was remained and didn't convert anymore. The mixture was added with water (10.00 mL) to quench at 25° C., and extracted using ethyl acetate (50 mL×2). Merged organic phases were washed by saturated saline water (20 mL), dried by anhydrous sodium sulfate, filtered and concentrated under reduced pressure. Residues were purified by a preparation TLC (silica gel, petroleum ether:ethyl acetate=1:1) to obtain 3-[[7-(tosyl)pyrrolo[2,3-d]pyrimidin-4-yl]amino]-3-azaspiro[5.5]undecane-9-ethyl formate (35.00 mg, yield was 6.58%) which was faint yellow solid. The value of $C_{26}H_{33}N_5O_4S[M+H]^+$ 512 was calculated using MS ESI, and was 512.

Step 5: an aqueous solution (1 mL) of sodium hydroxide (5.47 mg, 136.82 umol) was added in a mixed solution of tetrahydrofuran (2.00 mL) and methanol (2.00 mL) of 3-[[7-(tosyl)pyrrolo[2,3-d]pyrimidin-4-yl]amino]-3- azaspiro[5.5]undecane-9-ethyl formate (35.00 mg, 68.41 umol). The mixture was stirred for 1 h at 100° C. LC-MS showed the reaction was completed. The mixture was concentrated under reduced pressure. Residues were neutralized by diluted hydrochloric acid (2 M, 20 drops) and concentrated under reduced pressure to obtain 3-((7H-pyrrolo[2,3-d]pyrimidin-4-yl]amino]-3-azaspiro[5.5]undecane-9-formic acid (30.00 mg, crude product) which was faint yellow solid and directly used in next reaction without further purification. The value of $C_{17}H_{23}N_5O_2[M+H]^+$ 330 was calculated using MS ESI, and was 330.

Step 6: 3-((7H-pyrrolo[2,3-d]pyrimidin-4-yl]amino]-3-azaspiro[5.5]undecane-9-formic acid (30.00 mg, 91.07 umol), HOBt (36.92 mg, 273.22 umol) and EDCI (52.38 mg, 273.22 umol) were dissolved in DMF (2.00 mL); after the mixture was stirred for 30 min at 20° C., 2,2,2-trifluoroethylamine (18.04 mg, 182.15 umol) and triethylamine (36.86 mg, 364.30 umol) were added; and the mixture obtained was continuously stirred for 16 h at 20° C. LC-MS showed the reaction was completed. The mixture was diluted by water (5 mL) and extracted by a mixed solution of dichloromethane and methanol (10:1, 30 mL×2), and merged organic phases were washed by saturated saline solution (10 mL), dried by anhydrous sodium sulfate, filtered and concentrated under reduced pressure. Residues were purified by a alkalic type HPLC to obtain WX59: 3-(7H-pyrroolo[2,3-d]pyrimidin-4-yl)amino)-N-(2,2,2-trifluoroethyl)-3-azaspiro[5.5]undecane-9-formamide(10.00 mg, yield was 26.75%). The value of $C_{19}H_{25}F_3N_6O[M+H]^+$ 411 was calculated using MS ESI, and was 411. $^1$H NMR (400 MHz, METHANOL-$d_4$) δ=8.06 (s, 1H), 7.09 (d, J=3.5 Hz, 1H), 6.90 (br. S., 1H), 3.90 (q, J=9.5 Hz, 2H), 2.90 (br. S., 4H), 2.33-2.18 (m, 2H), 1.85-1.04 (m, 12H).

In Vitro Activity Test of Jak1, Jak 2 and Jak 3 Kinase

Test Material

Recombinant humanized JAK1, JAK2 and JAK3 protease were all purchased from Life technology. LANCE Ultra ULight™-JAK-1(Tyr1023) peptide and LANCE Eu-W1024 Anti-phosphotyrosine (PT66) were both purchased from PerkinElmer. Envision (PerkinElmer) was used to read a plate.

Test Method

Three dilution of a test compound was prepared, and 11 final concentrations were obtained: 10 uM to 0.17 nM. Each concentration had two repeat wells. The content of DMSO in a detection reaction was 1%.

JAK1 Enzyme Reaction:

2 nM JAK1 protein kinase, 50 nM LANCE Ultra ULight™-JAK-1(Tyr1023) peptide, 38 uM ATP, 50 mM HEPES (pH7.5), 10 mM MgCl2, 1 mM EGTA, 2 mM DTT, and 0.01% BRIJ-35. Detection plate was White Proxiplate 384-Plus plate (PerkinElmer), the reaction was conducted for 90 min at room temperature, and reaction system was 10 ul.

JAK2 Enzyme Reaction:

0.02 nM JAK2 protein kinase, 50 nM LANCE Ultra ULight™-JAK-1(Tyr1023) peptide, 12 uM ATP, 50 mM HEPES (pH7.5), 10 mM MgCl2, 1 mM EGTA, 2 mM DTT, and 0.01% BRIJ-35.Detection plate was White Proxiplate 384-Plus plate (PerkinElmer), the reaction was conducted for 60 min at room temperature, and a reaction system was 10 ul.

JAK3 Enzyme Reaction:

0.05 nM protein kinase, 50 nM LANCE Ultra ULight™-JAK-1(Tyr1023) peptide, 4 uM ATP, 50 mM HEPES (pH7.5), 10 mM MgCl2, 1 mM EGTA, 2 mM DTT, and 0.01% BRIJ-35. Detection plate was White Proxiplate 384-Plus plate (PerkinElmer), the reaction was conducted for 90 min at room temperature, and reaction system was 10 ul.

REACTION DETECTION:

10 ul detection reagent was added into the reaction plate, wherein the final concentration of LANCE Eu-W1024 Anti-phosphotyrosine (PT66) was 2 nM, the final concentration of EDTA was 10 mM, incubation was conducted for 60 min at room temperature, and the plate was read by the Envision.

Data Analysis

The reading was converted into a suppression ratio as follow equation: (%)=(Min−Ratio)/(Max−Min)*100%. IC50 data was detected by 4 parametric curve fitting (Model 205 in XLFIT5, iDBS), see Table 1.

| Embodiment | Compound ID | JAK1 | JAK2 | JAK3 |
|---|---|---|---|---|
| 1 | WX01 | A | B | B |
| 2 | WX02 | B | C | B |
| 3 | WX03 | A | B | B |
| 4 | WX04 | A | B | B |
| 5 | WX05 | A | B | A |
| 5 | WX06 | C | D | D |
| 6 | WX07 | A | B | A |
| 7 | WX08 | A | A | A |
| 7 | WX09 | C | D | D |
| 8 | WX10 | B | C | B |
| 9 | WX11 | C | C | C |
| 10 | WX12 | C | D | C |
| 11 | WX13 | C | D | C |
| 12 | WX14 | B | C | C |
| 13 | WX15 | B | C | C |
| 14 | WX16 | B | C | C |
| 15 | WX17 | C | D | C |
| 16 | WX18 | C | D | C |
| 17 | WX19 | C | D | C |
| 18 | WX20 | B | C | B |
| 19 | WX21 | B | D | C |
| 20 | WX22 | C | D | C |
| 21 | WX23 | B | C | B |
| 22 | WX24 | B | C | C |
| 23 | WX25 | B | C | C |
| 24 | WX26 | C | D | C |
| 25 | WX27 | C | D | C |
| 26 | WX28 | D | D | D |
| 27 | WX29 | D | D | C |
| 28 | WX30 | A | B | B |
| 29 | WX31 | A | B | B |
| 30 | WX32 | A | A | B |
| 30 | WX33 | B | C | B |
| 31 | WX34 | C | C | C |
| 32 | WX35 | D | D | D |
| 33 | WX36 | C | D | D |
| 34 | WX37 | D | D | D |
| 35 | WX38 | D | D | D |
| 36 | WX39 | B | C | C |
| 37 | WX40 | B | D | D |
| 38 | WX41 | B | C | C |
| 39 | WX42 | B | C | B |
| 40 | WX43 | A | B | B |
| 41 | WX44 | B | C | C |
| 42 | WX45 | B | C | C |
| 43 | WX46 | A | B | B |
| 44 | WX47 | A | B | A |
| 45 | WX48 | D | D | D |
| 46 | WX49 | A | A | A |
| 46 | WX50 | C | D | C |
| 47 | WX51 | D | D | D |
| 47 | WX52 | A | B | B |
| 48 | WX53 | B | C | C |
| 49 | WX54 | C | C | C |
| 50 | WX55 | C | D | D |
| 51 | WX56 | A | D | B |
| 52 | WX57 | B | B | B |
| 53 | WX58 | B | C | C |
| 54 | WX59 | C | D | D |

A ≤10 nM;
10 < B ≤ 10 nM;
100 < C ≤ 1000 nM;
D >1000 nM;

Pharmacokinetics (PK) Test

A test compound was dissolved and a clear solution was obtained which was administrated to male DBA/1 mice respectively via caudal vein injection and gavage (fasting overnight, 7-8 weeks old). After the tested compound was administrated, blood was respectively collected from mandibular vein from the intravenous injection group at 0.083, 0.25, 0.5, 1, 2, 4, 8 and 24 h, and from the gavage group at 0.25, 0.5, 1, 2, 4, 8 and 24 h, and the blood was centrifuged to obtain plasma. LC-MS/MS method was adopted to determine plasma drug concentration, and WinNonlin™ Version 6.3 pharmacokinetics software was used to calculate related pharmacokinetics parameters using a non-compartment model linear logarithmic trapezoidal method.

TABLE 2-1

PK test result of WX07 in mice

| PK Parameters | Mean |
|---|---|
| $T_{1/2}$ (h) | 1.35 |
| $Vd_{ss}$ (L/kg) | 0.846 |
| Cl (mL/min/kg) | 21.3 |
| $C_{max}$ (nM) | 2287 |
| $T_{max}$ (h) | 0.5 |
| $AUC_{0-last}$ (nM · h) | 2329 |
| $AUC_{0-inf}$ (nM · h) | 2480 |
| Bioavailability (%)$^a$ | 32.9 |

TABLE 2-2

PK test result of WX07 in rats

| PK Parameters | Mean |
|---|---|
| $T_{1/2}$ (hr) | 1.18 |
| $Vd_{ss}$ (L/kg) | 1.76 |
| Cl (mL/min/kg) | 31.8 |
| $C_{max}$ (nM) | 3253 |
| $T_{max}$ (hr) | 0.333 |
| $AUC_{0-last}$ (nM · hr) | 5678 |
| $AUC_{0-inf}$ (nM · hr) | 5749 |
| Bioavailability (%)$^a$ | 68.6 |

TABLE 3-1

PK test result of WX05 in mice

| PK Parameters | Mean IV |
|---|---|
| $T_{1/2}$ (h) | 0.515 |
| $Vd_{ss}$ (L/kg) | 0.959 |
| Cl (mL/min/kg) | 57.2 |
| $C_{max}$ (nM) | 1227 |
| $T_{max}$ (h) | 0.250 |
| $AUC_{0-last}$ (nM · h) | 664 |
| $AUC_{0-inf}$ (nM · h) | 667 |
| Bioavailability (%)$^a$ | 27.0 |

TABLE 3-2

PK test result of WX05 in rats

| PK Parameters | Mean |
|---|---|
| $T_{1/2}$ (hr) | 1.53 |
| $Vd_{ss}$ (L/kg) | 1.49 |
| Cl (mL/min/kg) | 13.1 |
| $C_{max}$ (nM) | 3687 |
| $T_{max}$ (hr) | 1.00 |
| $AUC_{0-last}$ (nM · hr) | 11243 |
| $AUC_{0-inf}$ (nM · hr) | 11513 |
| Bioavailability (%)$^a$ | 64.4 |

TABLE 4-1

PK test result of WX08 in mice

| PK Parameters | Mean IV |
|---|---|
| $T_{1/2}$ (h) | 0.623 |
| $Vd_{ss}$ (L/kg) | 0.619 |
| Cl (mL/min/kg) | 26.7 |
| $C_{max}$ (nM) | 2443 |
| $T_{max}$ (h) | 0.25 |
| $AUC_{0-last}$ (nM · h) | 3002 |
| $AUC_{0-inf}$ (nM · h) | 3030 |
| Bioavailability (%)$^a$ | 50.7 |

TABLE 4-2

PK test result of WX08 in rats

| PK Parameters | Mean |
|---|---|
| $T_{1/2}$ (hr) | 0.949 |
| $Vd_{ss}$ (L/kg) | 1.51 |
| Cl (mL/min/kg) | 27.1 |
| $C_{max}$ (nM) | 2460 |
| $T_{max}$ (hr) | 0.5 |
| $AUC_{0-last}$ (nM · hr) | 6356 |
| $AUC_{0-inf}$ (nM · hr) | 6498 |
| Bioavailability (%)$^a$ | 61 |

The compounds WX07, WX05 and WX08 of the present invention have excellent good oral bioavailability and higher exposed quantity in both mice and rats, which are beneficial for generating in-vivo efficacy.

Pharmacodynamic Test of an Arthritis Model Induced by Adjuvant on Rats

The therapeutic effect of the compound of the present invention for treatment of arthritis is verified by the arthritis model induced by adjuvant of rats.

After a female Lewis rat, 160 to 180 g, was narcotized by isoflurane, subcutaneous injection of 0. ml *Mycobacterium tuberculosis* suspension liquid was conducted to the left rear foot. The rats were classified 13 days after molding and corresponding tested compound were administrated, for example, 1 mpk, 3 mpk and 10 mpk tested compound WX07 and reference compound Tofacitinib were respectively administrated to the rats Tofacitinib and the compound of the present invention WX07 were dissolved in a mixed solvent of DMSO/PEG400/H2O, which was orally taken by a female Lewis rats (there were 10 tested animals in each dosage group). Additionally, 1 mpk, 3 mpk and 10 mpk tested compounds WX08 and reference compound Filgotinib were respectively given to the rats, Filgotinib and compound WX08 of the present invention were dissolved in the mixed solvent of DMSO/PEG400/H2O, which was orally taken by the Lewis female rat (there were 10 tested animals in each dosage group), and the weight of the rats was 160 to 170 g. The rats were medicated for two consecutive weeks, the condition of the rats were observed, and the swell condition of the foot volume was recorded and the grading was conducted. The test showed that the compound WX07 of the present invention showed good dose-effect relationship and arthritis inhibitory activity equivalent to Tofacitinib, and WX08 showed good dose-effect relationship and generated arthritis inhibitory activity that was more effective than Filgotinib.

TABLE 5-1

| Compound | Dosage (mg/kg) | AUC (%) |
|---|---|---|
| Tofacitinib | 1 | 19.8 |
| | 3 | 41.6 |
| | 10 | 49.2 |
| Compound WX07 | 1 | 1.5 |
| | 3 | 20.4 |
| | 10 | 44.7 |
| Compound WX08 | 1 | 13.6 |
| | 3 | 33.4 |
| | 10 | 49.2 |
| Filgotinib | 3 | 7.9 |

Pharmacodynamic Test of an Arthritis Model Induced by Collagen on Mice:

The effect of the compound of the present invention on treatment of arthritis was verified by the arthritis model induced by collagen on mice.

DBA/1 male mice were selected, the subcutaneous injection of the emulsion of collagen and freund's complete adjuvant were conducted at base of tail on $0^{th}$ day and $21^{st}$ day, the mice were classified on about $29^{th}$ day, tofacitinib (15 mpk), filgotinib (15 mpk) and the compounds of the present invention WX04 (15 mpk, 30 mpk), WX05 (15 mpk), WX07 (15 mpk), and WX (15 mpk) were dissolved in DMSO/PEG400/H2O[5/20/75 (v/v/v)], which were orally administrated to CIA mice (for Shanghai Slac Laboratory Animal Co., Ltd., there were 10 tested animals in each dosage group), the mice were medicated for two consecutive weeks, the weight of the mice were recorded during this period, the clinical score of joint inflammation of the mice was conducted, and the result showed that the compounds of the present invention WX04, WX05, WX07 and WX08 had obvious therapeutic effect on rheumatoid arthritis of the mice.

TABLE 5-2

| Compound | Dosage (mg/kg) | AUC (%) |
|---|---|---|
| Solvent control group | 0 | 0% |
| Tofacitinib | 15 | 34 |
| Filgotinib | 15 | 39.9 |
| Compound WX04 | 15 | 29 |
| | 30 | 27 |
| Compound WX05 | 15 | 31 |
| Compound WX06 | 15 | 30.3 |
| Compound WX07 | 15 | 52.2 |

The invention claimed is:
1. A compound of formula (I),

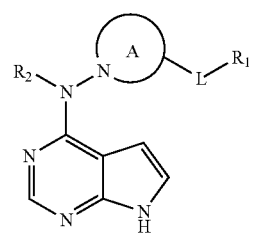

or a pharmaceutically acceptable salt thereof,
wherein:
  ring A is selected from optionally substituted: 5-12 membered heterocycloalkyl having from 1 to 4 ring heteroatoms selected from the group consisting of N, O and S;
  $R_1$ is selected from H or optionally substituted $C_{1-6}$ alkyl, $C_{1-6}$ heteroalkyl, $C_{3-6}$ cycloalkyl, 3~6 membered heterocycloalkyl, 5~6 membered aryl, or 5~6 membered heteroaryl;
  L is selected from single bond, —C(=O)O—, acyl or optionally substituted: amino, aminoacyl, acyl amino methylene and aminoacyl methylene; and when L contains a nitrogen atom, $R_1$ and optionally form an optionally substituted 3~6 membered ring with the nitrogen atom of L; and
  $R_2$ is selected from H, or optionally substituted $C_{1-3}$ alkyl and 3~6 membered cycloalkyl;
optionally, the structural unit

can be replaced by

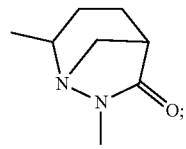

2. The compound of formula (I) or the pharmaceutically acceptable salt thereof according to claim 1, wherein substituents of the said 5-12 membered heterocycloalkyl, 5~6 membered heteroaryl, $C_{1-6}$ alkyl, $C_{1-6}$ heteroalkyl, $C_{3-6}$ cycloalkyl, 3~6 membered heterocycloalkyl, 5~6 membered aryl, 5~6 membered heteroaryl, amino, aminoacyl, acylamino methyl, aminoacyl methylene, $C_{1-3}$ alkyl, and 3~6 membered ring are selected from halogen, cyano, hydroxy, amino or selected from optional halogenated, hydroxylated and/or ammoniated $C_{1-3}$ alkyl and $C_{1-3}$ heteroalkyl;
  the number of the substituents is selected from 0, 1, 2, 3, 4 or 5; and
  the substituent is selected from F, Cl, Br, I, OH, $NH_2$, CN, Me, ethyl, n-propyl, isopropyl, cyclopropyl and trifluoromethyl.
3. The compound of formula (I) or the pharmaceutically acceptable salt thereof according to claim 1, wherein ring A is selected from optionally substituted piperidyl, piperazinyl, morpholinyl, pyrrolidinyl, oxazolinyl and 5-12 membered heterocyclyl group with 1~2 heteroatoms.

4. The compound of formula (I) or the pharmaceutically acceptable salt thereof according to claim 3, wherein ring A is selected from

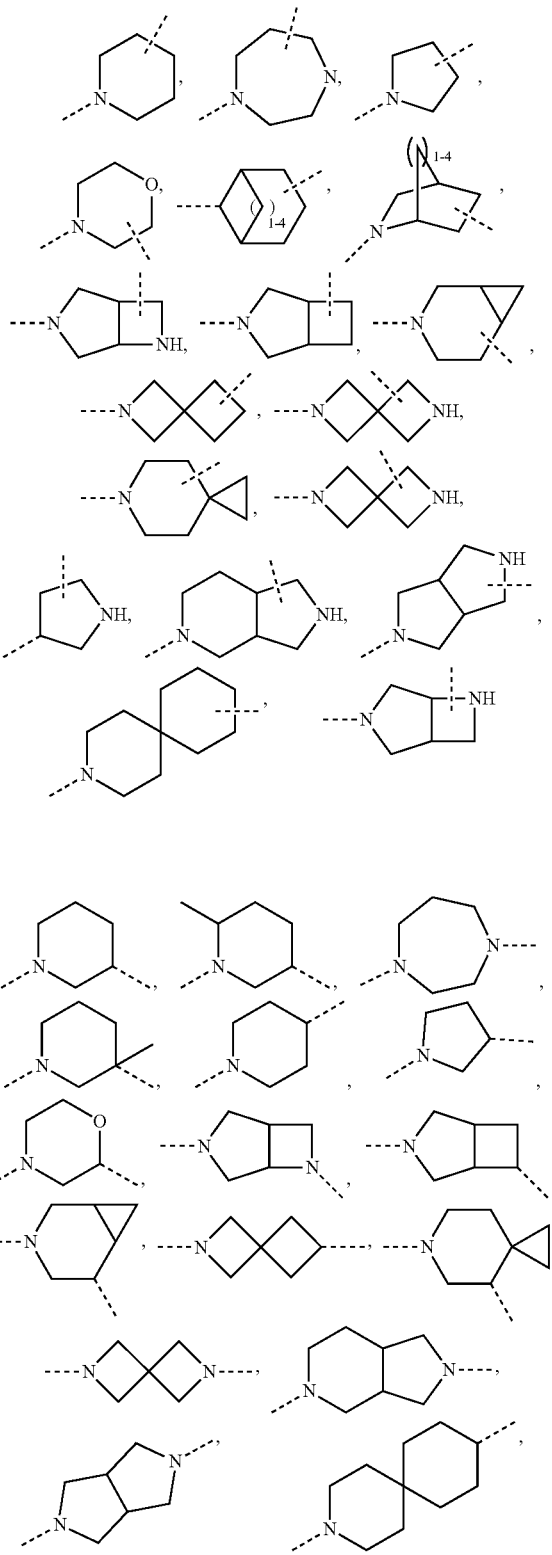

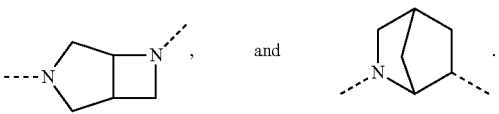

5. The compound of formula (I) or the pharmaceutically acceptable salt thereof according to claim 1, wherein $R_1$ is selected from H, or optionally substituted: $C_{1-4}$ alkyl, $C_{1-2}$ alkyl-O—$C_{1-2}$ alkyl-, $C_{1-2}$ alkyl-S—$C_{1-2}$ alkyl, $C_{4-5}$ cycloalkyl, 6 membered aryl, or 5 membered heteroaryl;

or optionally substituted: Me,

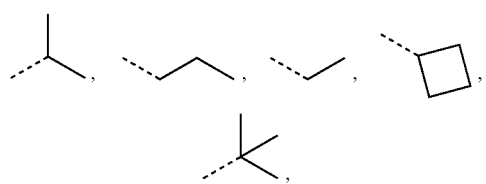

$C_{1-2}$ alkyl-O—$C_{1-2}$ alkyl-, $C_{1-2}$ alkyl-S—$C_{1-2}$ alkyl, imidazolyl and phenyl; or R1 is selected from

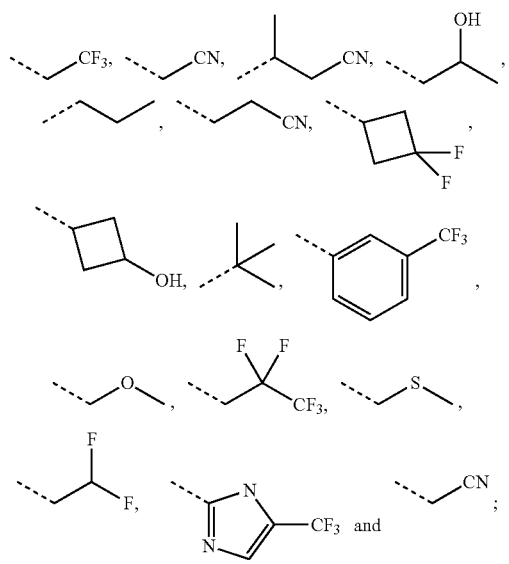

6. The compound of formula (I) or the pharmaceutically acceptable salt thereof according to claim 1, wherein $R_1$ and L together form an optionally substituted 4-5 membered ring;

form an optionally substituted

or form an optionally substituted

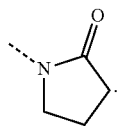

7. The compound of formula (I) or the pharmaceutically acceptable salt thereof according to claim 1, wherein R₁-L- is selected from optionally substituted: Me,

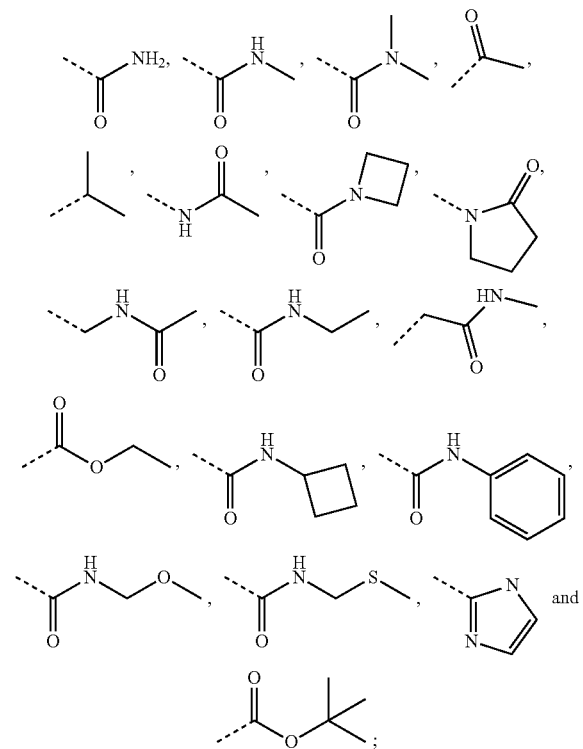

or R₁-L- is selected from

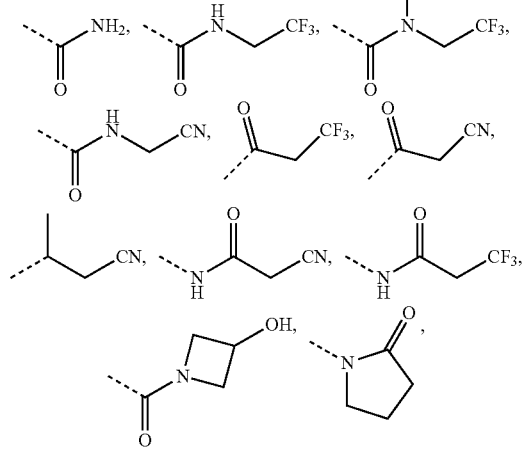

-continued

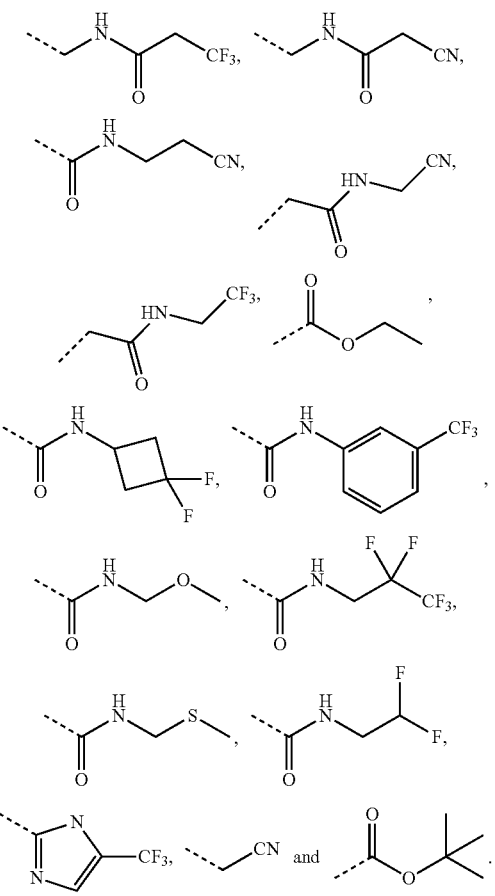

8. The compound of formula (I) or the pharmaceutically acceptable salt thereof according to claim 1, wherein R₂ is selected from H, methyl, ethyl or cyclopropyl.

9. The compound according to claim 1, wherein the compound is selected from:

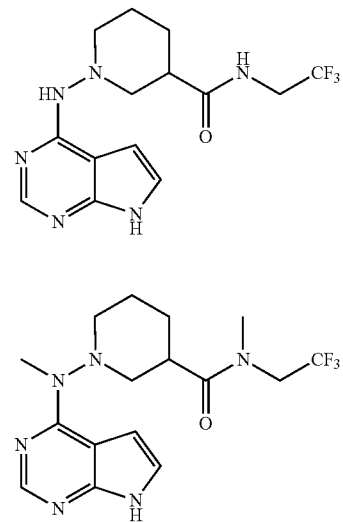

119
-continued
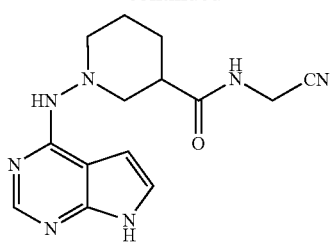
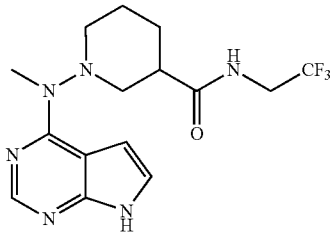
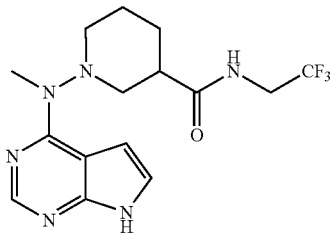
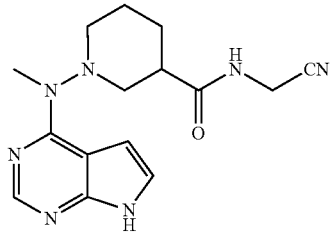
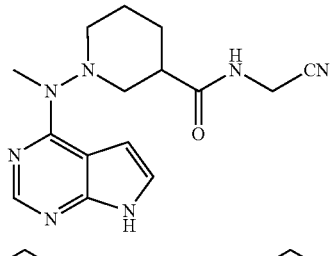
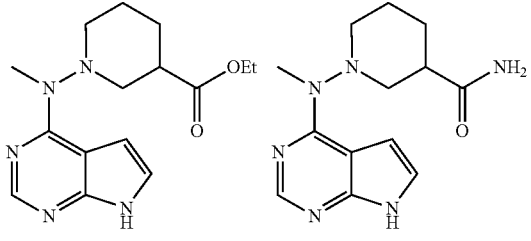
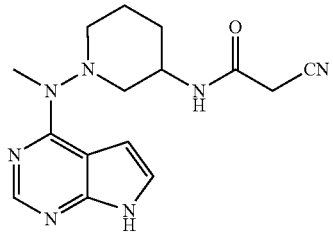
120
-continued
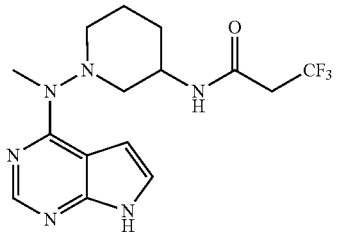
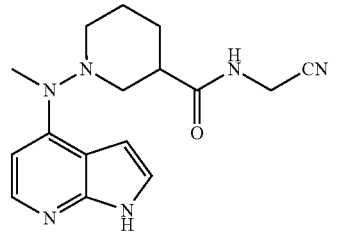
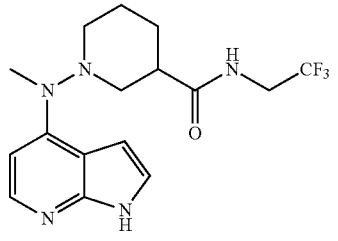
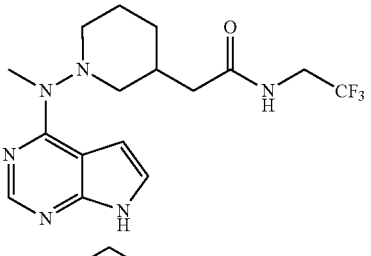
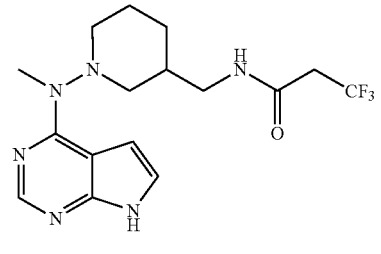

-continued
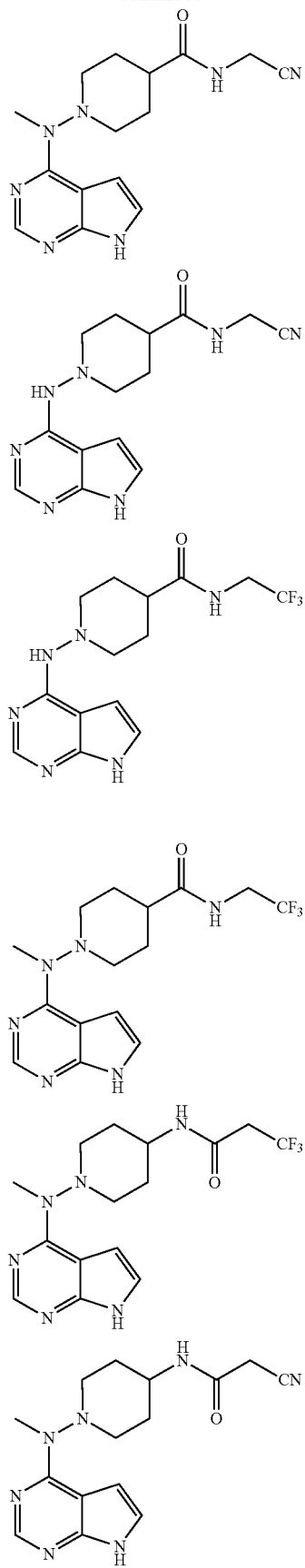
-continued
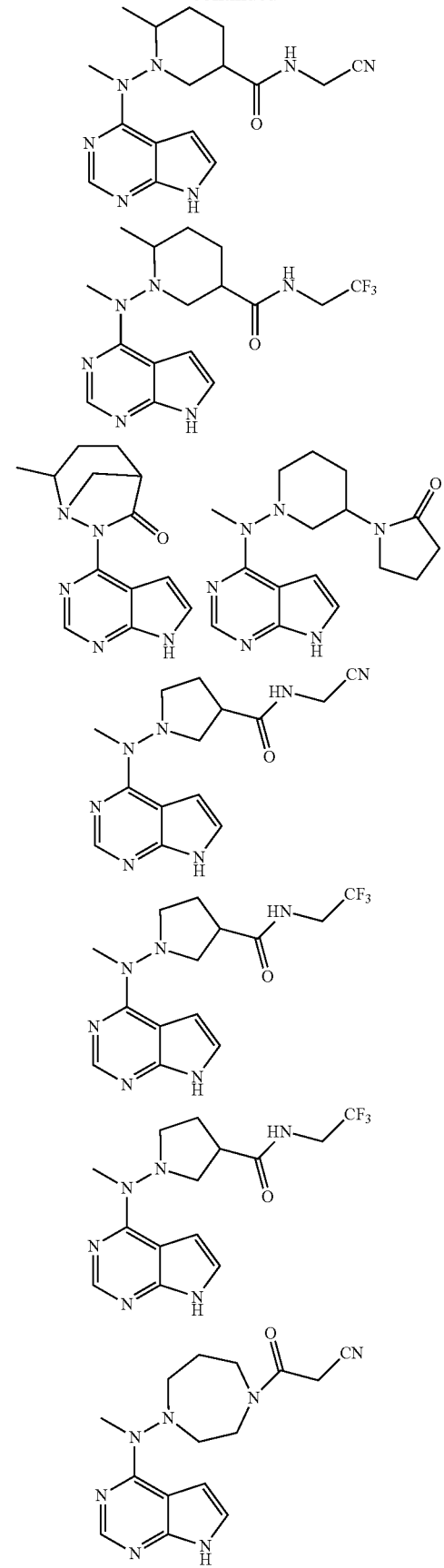

123
-continued
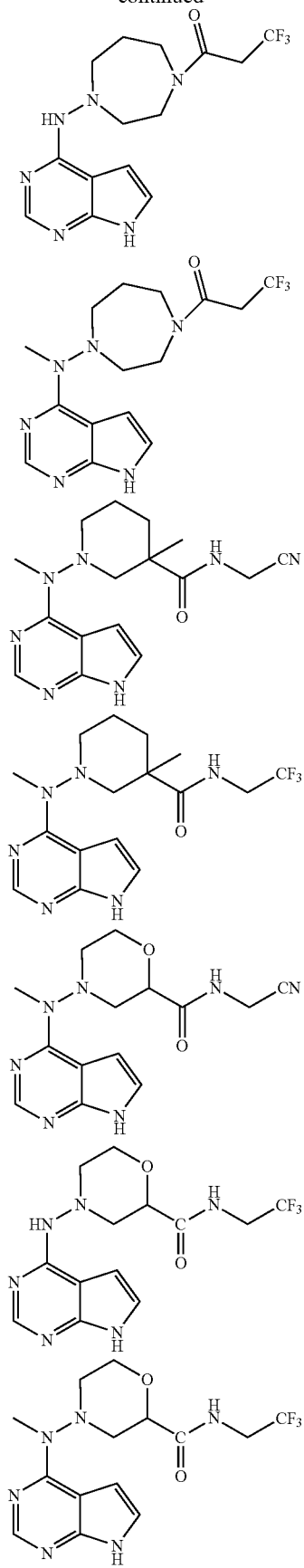
124
-continued
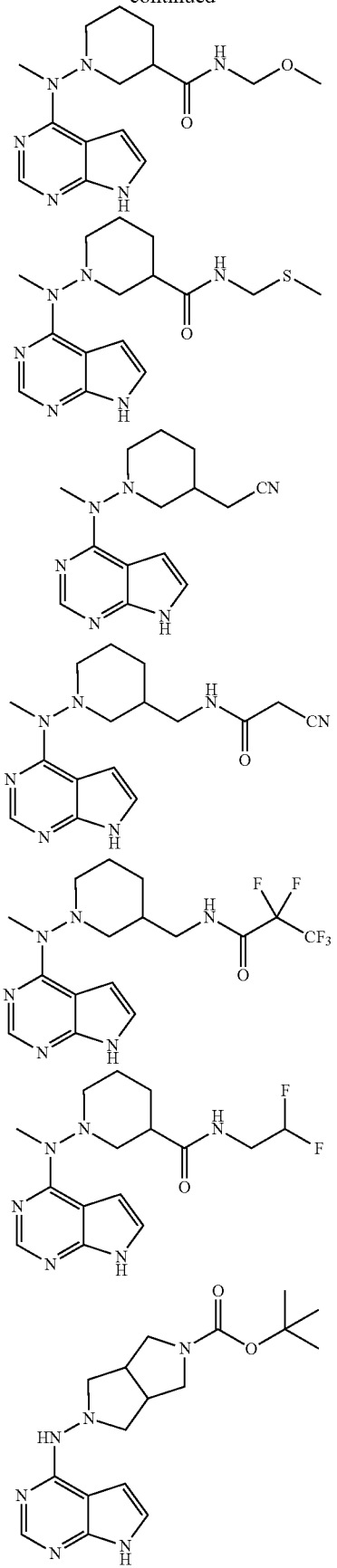

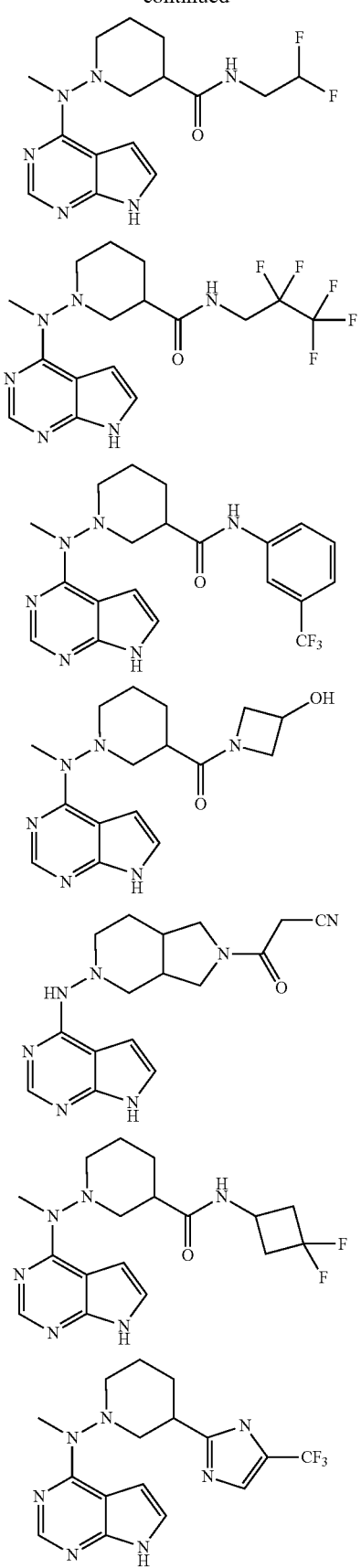

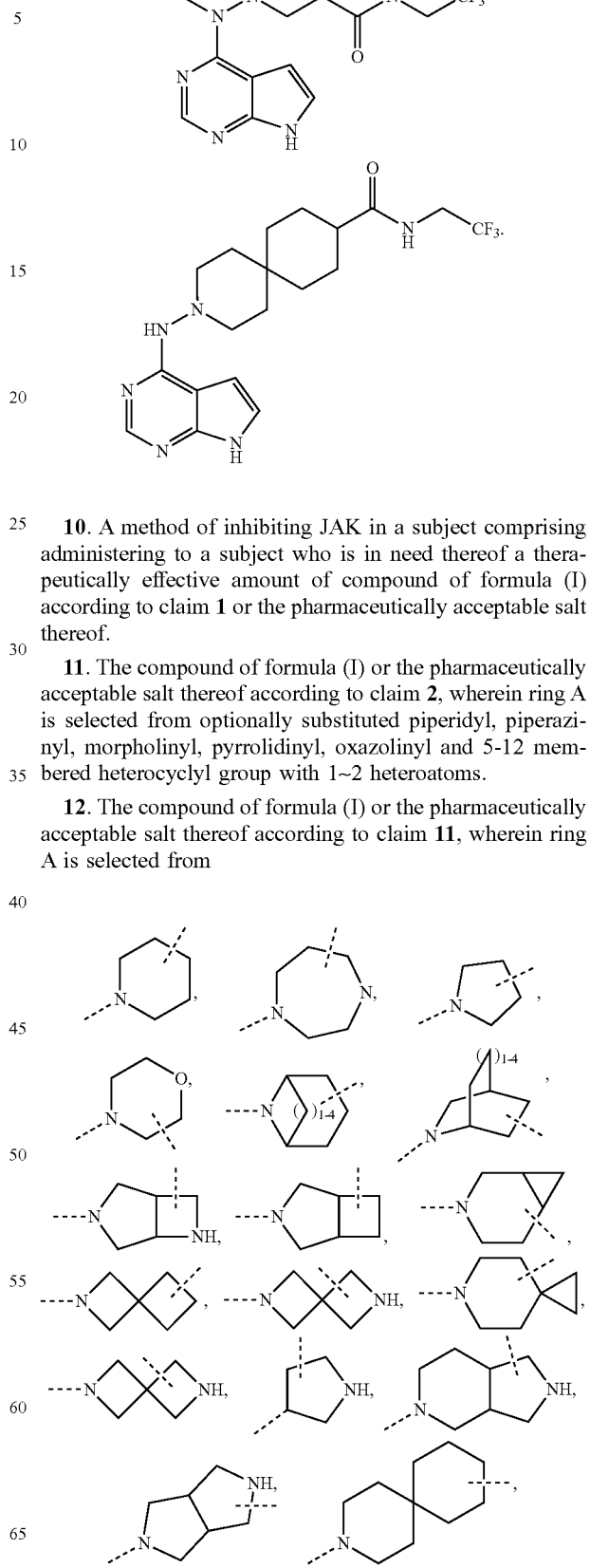

10. A method of inhibiting JAK in a subject comprising administering to a subject who is in need thereof a therapeutically effective amount of compound of formula (I) according to claim 1 or the pharmaceutically acceptable salt thereof.

11. The compound of formula (I) or the pharmaceutically acceptable salt thereof according to claim 2, wherein ring A is selected from optionally substituted piperidyl, piperazinyl, morpholinyl, pyrrolidinyl, oxazolinyl and 5-12 membered heterocyclyl group with 1~2 heteroatoms.

12. The compound of formula (I) or the pharmaceutically acceptable salt thereof according to claim 11, wherein ring A is selected from

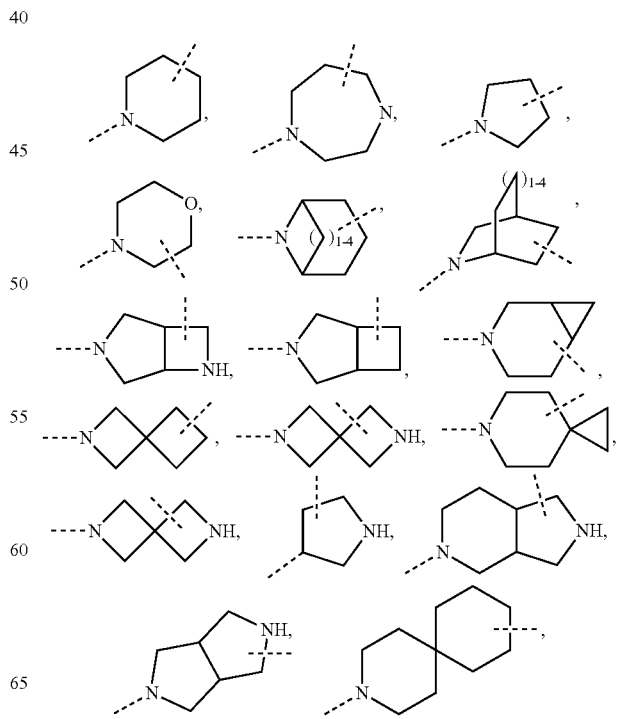

-continued

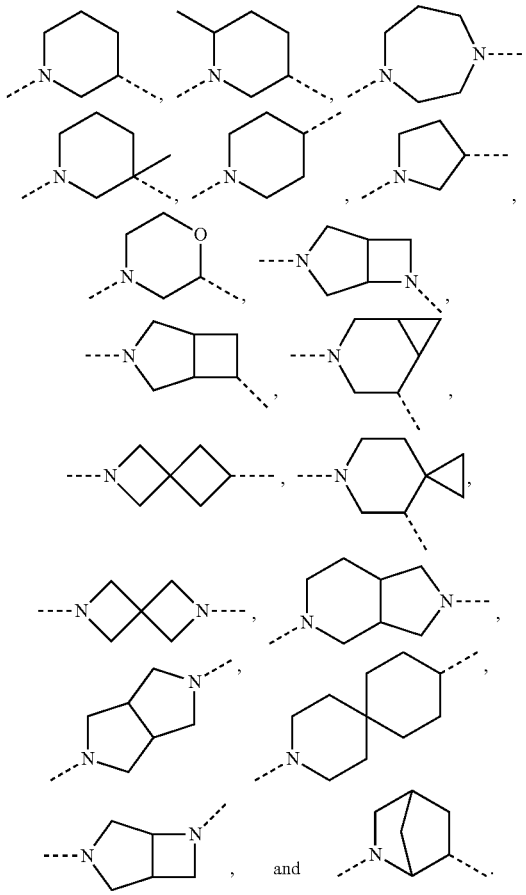

13. The compound of formula (I) or the pharmaceutically acceptable salt thereof according to claim 2, wherein $R_1$ is selected from H, or optionally substituted: $C_{1-4}$ alkyl, $C_{1-2}$ alkyl-O—$C_{1-2}$ alkyl-, $C_{1-2}$ alkyl-S—$C_{1-2}$ alkyl, $C_{4-5}$ cycloalkyl, 6 membered aryl, or 5 membered heteroaryl; or $R_1$ is selected from optionally substituted: Me,

$C_{1-2}$ alkyl-O—$C_{1-2}$ alkyl-, $C_{1-2}$ alkyl-S—$C_{1-2}$ alkyl, imidazolyl and phenyl;

or R1 is selected from

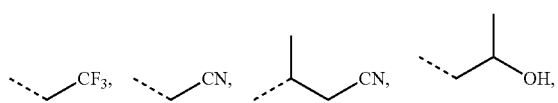

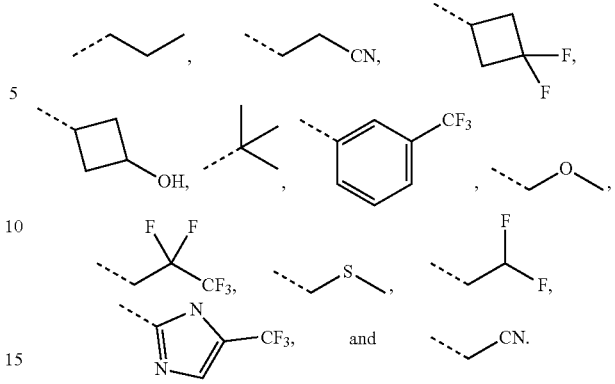

14. The compound of formula (I) or the pharmaceutically acceptable salt thereof according to claim 2, wherein $R_2$ is selected from H, methyl, ethyl or cyclopropyl.

15. A method of inhibiting JAK in a subject comprising administering to a subject who is in need thereof a therapeutically effective amount of compound of formula (I) according to claim 2 or the pharmaceutically acceptable salt thereof.

16. A method of inhibiting JAK in a subject comprising administering to a subject who is in need thereof a therapeutically effective amount of compound of formula (I) according to claim 3 or the pharmaceutically acceptable salt thereof.

17. A method of inhibiting JAK in a subject comprising administering to a subject who is in need thereof a therapeutically effective amount of compound of formula (I) according to claim 4 or the pharmaceutically acceptable salt thereof.

18. A method of inhibiting JAK in a subject comprising administering to a subject who is in need thereof a therapeutically effective amount of compound of formula (I) according to claim 5 or the pharmaceutically acceptable salt thereof.

19. A method of inhibiting JAK in a subject comprising administering to a subject who is in need thereof a therapeutically effective amount of compound of formula (I) according to claim 6 or the pharmaceutically acceptable salt thereof.

20. A method of inhibiting JAK in a subject comprising administering to a subject who is in need thereof a therapeutically effective amount of compound of formula (I) according to claim 7 or the pharmaceutically acceptable salt thereof.

21. A method of inhibiting JAK in a subject comprising administering to a subject who is in need thereof a therapeutically effective amount of compound of formula (I) according to claim 8 or the pharmaceutically acceptable salt thereof.

22. A method of inhibiting JAK in a subject comprising administering to a subject who is in need thereof a therapeutically effective amount of compound of formula (I) according to claim 9 or the pharmaceutically acceptable salt thereof.

23. A method of inhibiting JAK in a subject comprising administering to a subject who is in need thereof a therapeutically effective amount of compound of formula (I) according to claim 11 or the pharmaceutically acceptable salt thereof.

24. A method of inhibiting JAK in a subject comprising administering to a subject who is in need thereof a therapeutically effective amount of compound of formula (I) according to claim 12 or the pharmaceutically acceptable salt thereof.

25. A method of inhibiting JAK in a subject comprising administering to a subject who is in need thereof a therapeutically effective amount of compound of formula (I) according to claim 13 or the pharmaceutically acceptable salt thereof.

26. A method of inhibiting JAK in a subject comprising administering to a subject who is in need thereof a therapeutically effective amount of compound of formula (I) according to claim 14 or the pharmaceutically acceptable salt thereof.

27. A method of treating one of rheumatoid arthritis, organ transplant rejection, psoriasis, Crohn's disease, systemic lupus erythematosus, ulcerative colitis and atopic dermatitis in a subject comprising administering to a subject who is in need thereof a therapeutically effective amount of compound of formula (I) according to claim 1 or the pharmaceutically acceptable salt thereof.

* * * * *